(12) United States Patent
Xu et al.

(10) Patent No.: US 6,613,872 B1
(45) Date of Patent: Sep. 2, 2003

(54) COMPOUNDS FOR IMMUNOTHERAPY OF PROSTATE CANCER AND METHODS FOR THEIR USE

(75) Inventors: Jiangchun Xu, Bellevue, WA (US); Davin C. Dillon, Redmond, WA (US)

(73) Assignee: Corixa Corporation, Seattle, WA (US)

(*) Notice: Subject to any disclaimer, the term of this patent is extended or adjusted under 35 U.S.C. 154(b) by 0 days.

(21) Appl. No.: 09/159,812

(22) Filed: Sep. 23, 1998

Related U.S. Application Data

(63) Continuation-in-part of application No. 09/115,453, filed on Jul. 14, 1998, which is a continuation-in-part of application No. 09/030,607, filed on Feb. 25, 1998, now Pat. No. 6,262,245, which is a continuation-in-part of application No. 09/020,956, filed on Feb. 9, 1998, now Pat. No. 6,261,562, which is a continuation-in-part of application No. 08/904,804, filed on Aug. 1, 1997, now abandoned, which is a continuation-in-part of application No. 08/806,099, filed on Feb. 25, 1997, now abandoned.

(51) Int. Cl.$^7$ .......................... C07K 5/00; C07K 14/00; A61K 39/395; C07H 21/04
(52) U.S. Cl. ................. 530/300; 424/181.1; 530/350; 536/23.1
(58) Field of Search .................. 536/23.1; 530/300, 530/350; 424/181.1

(56) References Cited

U.S. PATENT DOCUMENTS 5,786,148 A  7/1998  Bandman et al.

FOREIGN PATENT DOCUMENTS

| EP | 317 141 A2 | 5/1989 |
|---|---|---|
| EP | 652 014 A1 | 5/1995 |
| WO | WO 93/14755 | 8/1993 |
| WO | WO 93/25224 | 12/1993 |
| WO | WO 94/09820 | 5/1994 |
| WO | WO 95/04548 | 2/1995 |
| WO | WO 95/14772 | 6/1995 |
| WO | WO 95/30758 | 11/1995 |
| WO | WO 96/21671 | 7/1996 |
| WO | WO 97/33909 | 9/1997 |
| WO | WO 98/12302 | 3/1998 |
| WO | WO 98/17687 | 4/1998 |
| WO | WO 98/20117 | 5/1998 |
| WO | WO 98/31799 | 7/1998 |
| WO | WO 98/37039 | 8/1998 |
| WO | WO 98/37093 | 8/1998 |
| WO | WO 98/37418 | 8/1998 |
| WO | WO 98/38310 | 9/1998 |
| WO | WO 98/39446 | 9/1998 |
| WO | WO 98/45435 | 10/1998 |
| WO | WO 98/50567 | 11/1998 |
| WO | WO 99/06548 | 2/1999 |
| WO | WO 99/06550 | 2/1999 |
| WO | WO 99/06552 | 2/1999 |
| WO | WO 99/25825 | 5/1999 |
| WO | WO 99/31236 | 6/1999 |
| WO | WO 01/51633 | 7/2001 |

OTHER PUBLICATIONS

Berlyn et al. "Developing dentritic cell polynucleotide vaccination for prostate cancer immunotherapy" Journal of Biotechnology vol. 73, pp. 155–179, 1999.*

El–Shirbiny, Prostatic Specific Antigen, *Advances In Clinical Chemistry 31*: 99–133, 1994.

Robson et al., "Identification of prostatic androgen regulated genes using the differential display technique," *Proceedings Of The American Association For Cancer Research Meeting 86, 36*: p. 266, Abstract No. 1589, 1995.

Short et al., "γZAP: a bacteriphage γ expression vector with in vivo excision properties," *Nucleic Acids Research 16*(15): 7583–7600, 1988.

Alexeyev et al., "Improved antibiotic–resistance gene cassettes and omega elements for *Escherichia coli* vector construction and in vitro deletion/insertion mutagenesis," *Gene 160*: 63–67, 1995.

Blok et al., "Isolation of cDNAs That Are Differentially Expressed Between Androgen–Dependent and Androgen–Independent Prostate Carcinoma Cells Using Differential Display PCR," *The Prostate 26*:213–224, 1995.

Database EMBL Accession No. AA453562, Jun. 11, 1997, Hillier et al., "Homo Sapiens cDNA Clone 788180."

Ahn and Kunkel, "The structural and functional diversity of dystrophin," *Nature Genetics 3*:283–291, Apr., 1993.

Chu et al., "CpG oligodeoxynucleotides act as adjuvants that switch on T helper 1 (Th 1) immunity," *J. Exp. Med. 186*(10): 1623–1631, Nov. 17, 1997.

Coleman et al., *Fundamental Immunology*, Wm. C. Brown Publishers, Dubuque, Iowa, 1989, pp. 465–466.

Derwent Geneseq Database, Accession No. V58522, Dec. 8, 1998.

Derwent Geneseq Database, Accession No. V61287, Jan. 6, 1999.

Duerst and Nees, "Nucleic acid characteristic of late or early passage cells immortalized by papilloma virus–and related polypeptide(s) and antibodies, used for diagnosis and treatment of cervical cancer and assessing potential for progression of cervical lesions," Derwent World Patent Index, Accession No. 1998–121623, 1998. See also German Patent DE 19649207 C1.

(List continued on next page.)

Primary Examiner—Kenneth R. Horlick
Assistant Examiner—Young Kim
(74) Attorney, Agent, or Firm—Seed Intellectual Property Law Group PLLC

(57) ABSTRACT

Compounds and methods for treating prostate cancer are provided. The inventive compounds include polypeptides containing at least a portion of a prostate tumor protein. Vaccines and pharmaceutical compositions for immunotherapy of prostate cancer comprising such polypeptides, or DNA molecules encoding such polypeptides, are also provided, together with DNA molecules for preparing the inventive polypeptides.

7 Claims, 3 Drawing Sheets

OTHER PUBLICATIONS

Ezzell, C., "Cancer vaccines: an idea whose time has come?" *The Journal of NIH Research* 7:46–49, Jan., 1995.

Harris et al., "Polycystic Kidney Disease 1: identification and analysis of the primary defect," *J. Am. Soc. of Nephrol.* 6:1125–1133, 1995.

Hillier et al., Genback Accession No. AA100799, Dec. 23, 1997.

Hillier et al., Genbank Accession No. R20590, Apr. 18, 1995.

Hudson, T., Genbank Accession No. G22461, May 31, 1996.

Kroger, B. "New serine protease form human prostate, useful for identifying specific inhibitors, antibodies and probes," Derwent World Patent Index, Accession No. 99-432218, 1999. See also European Patent EP 936 270 A2.

National Cancer Institute, Cancer Genome Anatomy Project (NCI–CGAP), Genbank Accession No. AA551449, Sep. 5, 1997.

National Cancer Institute, Cancer Genome Anatomy Project (NCI–CGAP), Genbank Accession No. AA551759, Aug. 11, 1997.

National Cancer Institute, Cancer Genome Anatomy Project (NCI–CGAP), Genbank Accession No. AA631143, Oct. 31, 1997.

National Cancer Institute, Cancer Genome Anatomy Project (NCI–CGAP), Genbank Accession No. AA653016, Nov. 25, 1997.

Sjögren, H., "Therapeutic Immunization Against Cancer Antigens Using Genetically Engineered Cells," *Immunotechnology* 3: 161–172, 1997.

Zitvogel et al., "Eradication of Established Murine Tumors Using a Novel Cell–Free Vaccine: Dendritic Cell–Derived Exosomes," *Nature Medicine* 4(5): 594–600, May, 1998.

Hara et al., "Characterization of cell phenotype by a novel cDNA library subtraction system: expression of CD8α in a mast cell–derived interleukin–4–dependent cell line," *Blood* 84(1):189–199, Jul. 1, 1994.

Nelson et al., Genbank Accession No. NP_004908, Mar. 18, 2000.

Sherman et al., "Selecting T cell receptors with high affinity for self–MHC by decreasing the contribution of CD8," *Science* 258(5083):815–818, Oct. 30, 1992.

Theobald, et al., "Targeting p53 as a general tumor antigen," *Proc. Natl. Sci. USA* 92(25):11993–11997, Dec. 5, 1995.

Vasmatzis et al., "Discovery of three genes specifically expressed in human prostate by expressed sequence tag database analysis," *Proc. Natl. Acad. Sci. USA* 95(1):300–304, Jan. 6, 1998.

* cited by examiner

SEQUENCE LISTING

<160> NUMBER OF SEQ ID NOS: 306

<210> SEQ ID NO 1
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 1

```
ttttttttt tttttcacag tataacagct ctttatttct gtgagttcta ctaggaaatc      60
atcaaatctg agggttgtct ggaggacttc aatacacctc cccccatagt gaatcagctt     120
ccagggggtc cagtccctct ccttacttca tccccatccc atgccaaagg aagacctcc     180 ctccttggct cacagccttc tctaggcttc ccagtgcctc caggacagag tgggttatgt     240
tttcagctcc atccttgctg tgagtgtctg gtgcgttgtg cctccagctt ctgctcagtg     300
cttcatggac agtgtccagc acatgtcact ctccactctc tcagtgtgga tccactagtt     360
ctagagcggc cgccaccgcg gtggagctcc agctttttgtt ccctttagtg agggttaatt    420
gcgcgcttgg cgtaatcatg gtcataactg tttcctgtgt gaaattgtta tccgctcaca    480
attccacaca acatacgagc cggaagcata aagtgtaaag cctggggtgc ctaatgagtg    540
anctaactca cattaattgc gttgcgctca ctgnccgctt tccagtcngg aaaactgtcg    600
tgccagctgc attaatgaat cggccaacgc ncggggaaaa gcggtttgcg ttttggggc     660 tcttccgctt ctcgctcact nantcctgcg ctcggtcntt cggctgcggg gaacggtatc    720
actcctcaaa ggnggtatta cggttatccn naaatcnggg gatacccngg aaaaaanttt    780
aacaaaaggg cancaaaggg cngaaacgta aaaa                                 814
```

<210> SEQ ID NO 2
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 2

| | | | | | |
|---|---|---|---|---|---|
| acagaaatgt | tggatggtgg | agcacctttc | tatacgactt | acaggacagc | agatggggaa | 60 |
| ttcatggctg | ttggagcaat | agaacccag | ttctacgagc | tgctgatcaa | aggacttgga | 120 |
| ctaaagtctg | atgaacttcc | caatcagatg | agcatggatg | attggccaga | aatgaagaag | 180 |
| aagtttgcag | atgtatttgc | aaagaagacg | aaggcagagt | ggtgtcaaat | cttttgacggc | 240 |
| acagatgcct | gtgtgactcc | ggttctgact | tttgaggagg | ttgttcatca | tgatcacaac | 300 |
| aaggaacggg | gctcgtttat | caccagtgag | gagcaggacg | tgagccccg | ccctgcacct | 360 |
| ctgctgttaa | acaccccagc | catcccttct | ttcaaaaggg | atccactagt | tctagaagcg | 420 |
| gccgccaccg | cggtggagct | ccagcttttg | ttccctttag | tgagggttaa | ttgcgcgctt | 480 |
| ggcgtaatca | tggtcatagc | tgtttcctgt | gtgaaattgt | tatccgctca | caattccccc | 540 |
| aacatacgag | ccggaacata | aagtgttaag | cctgggtgc | ctaatgantg | agctaactcn | 600 |
| cattaattgc | gttgcgctca | ctgcccgctt | ccagtcggg | aaaactgtcg | tgccactgcn | 660 |
| ttantgaatc | ngccacccc | cgggaaaagg | cggttgcntt | ttgggcctct | tccgctttcc | 720 |
| tcgctcattg | atcctngcnc | ccggtcttcg | gctgcggnga | acggttcact | cctcaaaggc | 780 |
| ggtntnccgg | ttatccccaa | acngggata | cccnga | | | 816 |

<210> SEQ ID NO 3
<211> LENGTH: 773
<212> TYPE: DNA
<213> ORGANISM: Homo sapien
<220> FEATURE:
<221> NAME/KEY: misc_feature
<222> LOCATION: (1)...(773)
<223> OTHER INFORMATION: n = A,T,C or G

<400> SEQUENCE: 3

| | | | | | |
|---|---|---|---|---|---|
| cttttgaaag | aagggatggc | tggggtgttt | aacagcagag | gtgcagggcg | ggggctcacg | 60 |
| tcctgctcct | cactggtgat | aaacgagccc | cgttccttgt | tgtgatcatg | atgaacaacc | 120 |
| tcctcaaaag | tcagaaccgg | agtcacacag | gcatctgtgc | cgtcaaagat | ttgacaccac | 180 |
| tctgccttcg | tcttctttgc | aaatacatct | gcaaacttct | tcttcatttc | tggccaatca | 240 |
| tccatgctca | tctgattggg | aagttcatca | gactttagtc | canntccttt | gatcagcagc | 300 |
| tcgtagaact | ggggttctat | tgctccaaca | gccatgaatt | ccccatctgc | tgtcctgtaa | 360 |
| gtcgtataga | aggtgctcc | accatccaac | atgttctgtc | ctcgaggggg | ggcccggtac | 420 |
| ccaattcgcc | ctatantgag | tcgtattacg | cgcgctcact | ggccgtcgtt | ttacaacgtc | 480 |
| gtgactggga | aaaccctggg | cgttaccaac | ttaatcgcct | tgcagcacat | cccccttttcg | 540 |
| ccagctgggg | gtaatancga | aaaggcccgc | accgatcgcc | cttccaacag | ttgcgcacct | 600 |
| gaatgggnaa | atgggacccc | cctgttaccg | cgcattnaac | cccgcnggg | tttngttgtt | 660 |
| accccacnt | nnaccgctta | cacttttgcca | gcgccttanc | gcccgctccc | tttcnccttt | 720 |
| cttcccttcc | tttcncncnn | ctttcccccg | gggtttcccc | cntcaaaccc | cna | 773 |

<210> SEQ ID NO 4
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 4

| | | | | |
|---|---|---|---|---|
| cctcctgagt | cctactgacc | tgtgctttct | ggtgtggagt | ccagggctgc | taggaaaagg | 60 |
| aatgggcaga | cacaggtgta | tgccaatgtt | tctgaaatgg | gtataatttc | gtcctctcct | 120 |
| tcggaacact | ggctgtctct | gaagacttct | cgctcagttt | cagtgaggac | acacacaaag | 180 |
| acgtgggtga | ccatgttgtt | tgtggggtgc | agagatggga | ggggtggggc | ccaccctgga | 240 |
| agagtggaca | gtgacacaag | gtggacactc | tctacagatc | actgaggata | agctggagcc | 300 |
| acaatgcatg | aggcacacac | acagcaagga | tgacnctgta | aacatagccc | acgctgtcct | 360 |
| gnggcactg | ggaagcctan | atnaggccgt | gagcanaaag | aaggggagga | tccactagtt | 420 |
| ctanagcggc | cgccaccgcg | gtgganctcc | ancttttgtt | ccctttagtg | agggttaatt | 480 |
| gcgcgcttgg | cntaatcatg | gtcatanctn | tttcctgtgt | gaaattgtta | tccgctcaca | 540 |
| attccacaca | acatacgnac | cggaaacata | aantgtaaac | ctggggtgcc | taatgantga | 600 |
| ctaactcaca | ttaattgcgt | tgcgctcact | gcccgctttc | caatcnggaa | acctgtcttg | 660 |
| ccncttgcat | tnatgaatcn | gccaaccccc | ggggaaaagc | gtttgcgttt | tgggcgctct | 720 |
| tccgcttcct | cnctcantta | ntccctncnc | tcggtcattc | cggctgcngc | aaaccggttc | 780 |
| accnctcca | aaggggtat | tccggtttcc | ccnaatccgg | gganancc | | 828 |

<210> SEQ ID NO 5
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 5

| | | | | | | |
|---|---|---|---|---|---|---|
| tttttttttt | tttttactga | tagatggaat | ttattaagct | tttcacatgt | gatagcacat | 60 |
| agttttaatt | gcatccaaag | tactaacaaa | aactctagca | atcaagaatg | gcagcatgtt | 120 |
| attttataac | aatcaacacc | tgtggctttt | aaaatttggt | tttcataaga | taatttatac | 180 |
| tgaagtaaat | ctagccatgc | ttttaaaaaa | tgctttaggt | cactccaagc | ttggcagtta | 240 |
| acatttggca | taaacaataa | taaaacaatc | acaatttaat | aaataacaaa | tacaacattg | 300 |
| taggccataa | tcatatacag | tataaggaaa | aggtggtagt | gttgagtaag | cagttattag | 360 |
| aatagaatac | cttggcctct | atgcaaatat | gtctagacac | tttgattcac | tcagccctga | 420 |
| cattcagttt | tcaaagtagg | agacaggttc | tacagtatca | ttttacagtt | tccaacacat | 480 |
| tgaaaacaag | tagaaaatga | tgagttgatt | tttattaatg | cattacatcc | tcaagagtta | 540 |
| tcaccaaccc | ctcagttata | aaaaattttc | aagttatatt | agtcatataa | cttggtgtgc | 600 |
| ttattttaaa | ttagtgctaa | atggattaag | tgaagacaac | aatggtcccc | taatgtgatt | 660 |
| gatattggtc | atttttacca | gcttctaaat | ctnaactttc | aggcttttga | actggaacat | 720 |
| tgnatnacag | tgttccanag | ttncaaccta | ctggaacatt | acagtgtgct | tgattcaaaa | 780 |
| tgttattttg | ttaaaaatta | aattttaacc | tggtggaaaa | ataatttgaa | atna | 834 |

<210> SEQ ID NO 6
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 6

| | | | | | |
|---|---|---|---|---|---|
| tttttttttt | tttttttttt | aagaccctca | tcaatagatg | gagacataca | gaaatagtca | 60 |
| aaccacatct | acaaaatgcc | agtatcaggc | ggcggcttcg | aagccaaagt | gatgtttgga | 120 |
| tgtaaagtga | aatattagtt | ggcggatgaa | gcagatagtg | aggaaagttg | agccaataat | 180 |
| gacgtgaagt | ccgtggaagc | ctgtggctac | aaaaaatgtt | gagccgtaga | tgccgtcgga | 240 |
| aatggtgaag | ggagactcga | agtactctga | ggcttgtagg | agggtaaaat | agagacccag | 300 |
| taaaattgta | ataagcagtg | cttgaattat | ttggtttcgg | ttgttttcta | ttagactatg | 360 |
| gtgagctcag | gtgattgata | ctcctgatgc | gagtaatacg | gatgtgttta | ggagtgggac | 420 |
| ttctagggga | tttagcgggg | tgatgcctgt | tgggggccag | tgccctccta | gttgggggt | 480 |
| aggggctagg | ctggagtggt | aaaaggctca | gaaaaatcct | gcgaagaaaa | aaacttctga | 540 |
| ggtaataaat | aggattatcc | cgtatcgaag | gccttttggg | acaggtggtg | tgtggtggcc | 600 |
| ttggtatgtg | ctttctcgtg | ttacatcgcg | ccatcattgg | tatatggtta | gtgtgttggg | 660 |
| ttantanggc | ctantatgaa | gaacttttgg | antggaatta | aatcaatngc | ttggccggaa | 720 |
| gtcattanga | nggctnaaaa | ggccctgtta | ngggtctggg | ctnggtttta | cccnacccat | 780 |
| ggaatncncc | ccccggacna | ntgnatccct | attcttaa | | | 818 |

<210> SEQ ID NO 7
<211> LENGTH: 817
<212> TYPE: DNA
<213> ORGANISM: Homo sapien
<220> FEATURE:
<221> NAME/KEY: misc_feature
<222> LOCATION: (1)...(817)
<223> OTHER INFORMATION: n = A,T,C or G

<400> SEQUENCE: 7

| | | | | | |
|---|---|---|---|---|---|
| tttttttttt | tttttttttt | tggctctaga | gggggtagag | ggggtgctat | agggtaaata | 60 |
| cgggccctat | ttcaaagatt | tttaggggaa | ttaattctag | gacgatgggt | atgaaactgt | 120 |
| ggtttgctcc | acagatttca | gagcattgac | cgtagtatac | ccccggtcgt | gtagcggtga | 180 |
| aagtggtttg | gtttagacgt | ccgggaattg | catctgtttt | taagcctaat | gtggggacag | 240 |
| ctcatgagtg | caagacgtct | tgtgatgtaa | ttattatacn | aatgggggct | tcaatcggga | 300 |
| gtactactcg | attgtcaacg | tcaaggagtc | gcaggtcgcc | tggttctagg | aataatgggg | 360 |
| gaagtatgta | ggaattgaag | attaatccgc | cgtagtcggt | gttctcctag | gttcaatacc | 420 |
| attggtggcc | aattgatttg | atggtaaggg | gagggatcgt | tgaactcgtc | tgttatgtaa | 480 |
| aggatncctt | ngggatggga | aggcnatnaa | ggactangga | tnaatggcgg | gcangatatt | 540 |
| tcaaacngtc | tctanttcct | gaacgtctg | aatgttaat | aanaattaan | tttgttatt | 600 |
| gaatnttnng | gaaagggct | tacaggacta | gaaaccaaat | angaaaanta | atnntaangg | 660 |
| cnttatcntn | aaaggtnata | accnctccta | tnatcccacc | caatngnatt | ccccacncnn | 720 |
| acnattggat | ncccccanttc | canaaanggc | cncccccgg | tgnanncnc | cttttgttcc | 780 |

<210> SEQ ID NO 8
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 8

```
catttccggg tttactttct aaggaaagcc gagcggaagc tgctaacgtg ggaatcggtg    60
cataaggaga actttctgct ggcacgcgct agggacaagc gggagagcga ctccgagcgt   120
ctgaagcgca cgtcccagaa ggtggacttg gcactgaaac agctgggaca catccgcgag   180
tacgaacagc gcctgaaagt gctggagcgg gaggtccagc agtgtagccg cgtcctgggg   240
tgggtggccg angcctganc cgctctgcct tgctgccccc angtgggccg ccaccccctg   300
acctgcctgg gtccaaacac tgagccctgc tggcggactt caagganaac ccccacangg   360
ggattttgct cctanantaa ggctcatctg ggcctcggcc ccccacctg gttggccttg   420
tctttgangt gagccccatg tccatctggg ccactgtcng gaccacctt ngggagtgtt   480
ctccttacaa ccacannatg cccggctcct cccggaaacc antcccancc tgngaaggat   540
caagncctgn atccactnnt nctanaaccg gccncnccg cngtggaacc cnccttntgt   600
tcctttcnt tnagggttaa tnncgccttg gccttnccan ngtcctncnc nttttccnnt   660
gttnaaattg ttangcnccc ncnntcccn cnncnncnan cccgacccnn annttnnann   720
ncctgggggt ccnncngat tgaccnncc ncctntant tgcnttnggg nncnntgccc   780
ctttccctct ngggannncg                                              799
```

<210> SEQ ID NO 9
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 9

```
acgccttgat cctcccaggc tgggactggt tctgggagga gccgggcatg ctgtggtttg    60
taangatgac actcccaaag gtggtcctga cagtggccca gatggacatg gggctcacct   120
caaggacaag gccaccaggt gcgggggccg aagcccacat gatccttact ctatgagcaa   180
aatcccctgt gggggcttct ccttgaagtc cgccancagg gctcagtctt tggacccang   240
caggtcatgg ggttgtngnc caactggggg ccncaacgca aaanggcnca gggcctcngn   300
cacccatccc angacgcggc tacactnctg gacctcccnc tccaccactt tcatgcgctg   360
ttcntacccg cgnatntgtc ccanctgttt cngtgccnac tccancttct nggacgtgcg   420
ctacatacgc ccggantcnc nctcccgctt tgtccctatc cacgtnccan caacaaattt   480
cnccntantg caccnattcc cacntttnnc agntttccnc nncgngcttc cttntaaaag   540
ggttganccc cggaaaatnc cccaaggggg ggggccngg tacccaactn cccctnata   600
gctgaantcc ccatnaccnn gnctcnatgg ancnntccnt tttaannacn ttctnaactt   660
gggaanancc ctcgnccntn ccccnttaa tcccnccttg cnangnncnt ccccnntcc   720
ncccnnntng gcntntnann cnaaaaggc ccnnnancaa tctcctnncn cctcanttcg   780
```

```
ccanccctcg aaatcggccn c                                              801
```

<210> SEQ ID NO 10
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 10

```
cagtctatnt ggccagtgtg gcagctttcc ctgtggctgc cggtgccaca tgcctgtccc     60
acagtgtggc cgtggtgaca gcttcagccg ccctcaccgg gttcaccttc tcagccctgc   120
agatcctgcc ctacacactg gcctccctct accaccggga gaagcaggtg ttcctgccca   180
aataccgagg ggacactgga ggtgctagca gtgaggacag cctgatgacc agcttcctgc   240
caggccctaa gcctggagct cccttcccta atggacacgt gggtgctgga ggcagtggcc   300
tgctcccacc tccacccgcg ctctgcgggg cctctgcctg tgatgtctcc gtacgtgtgg   360
tggtgggtga gcccaccgan gccagggtgg ttccgggccg gggcatctgc ctggacctcg   420
ccatcctgga tagtgcttcc tgctgtccca ngtggcccca tccctgttta tgggctccat   480
tgtccagctc agcagtctg tcactgccta tatggtgtct gccgcaggcc tgggtctggt   540
cccatttact ttgctacaca ggtantattt gacaagaacg anttggccaa atactcagcg   600
ttaaaaaatt ccagcaacat tgggggtgga aggcctgcct cactgggtcc aactccccgc   660
tcctgttaac cccatggggc tgccggcttg ccgccaatt tctgttgctg ccaaantnat    720
gtggctctct gctgccacct gttgctggct gaagtgcnta cngcncanct nggggggtng   780
ggngttccc                                                          789
```

<210> SEQ ID NO 11
<211> LENGTH: 772
<212> TYPE: DNA
<213> ORGANISM: Homo sapien
<220> FEATURE:
<221> NAME/KEY: misc_feature
<222> LOCATION: (1)...(772)
<223> OTHER INFORMATION: n = A,T,C or G

<400> SEQUENCE: 11

```
cccaccctac ccaaatatta gacaccaaca cagaaaagct agcaatggat tcccttctac     60
tttgttaaat aaataagtta aatatttaaa tgcctgtgtc tctgtgatgg caacagaagg   120
accaacaggc cacatcctga taaaggtaa gaggggggtg gatcagcaaa aagacagtgc   180
tgtgggctga ggggacctgg ttcttgtgtg ttgcccctca ggactcttcc cctacaaata   240
actttcatat gttcaaatcc catggaggag tgtttcatcc tagaaactcc catgcaagag   300
ctacattaaa cgaagctgca ggttaagggg cttanagatg ggaaaccagg tgactgagtt   360
tattcagctc ccaaaaaccc ttctctaggt gtgtctcaac taggaggcta gctgttaacc   420
ctgagcctgg gtaatccacc tgcagagtcc ccgcattcca gtgcatggaa cccttctggc   480
ctccctgtat aagtccagac tgaaacccc ttggaaggnc tccagtcagg cagccctana   540
aactggggaa aaaagaaaag gacgccccan ccccagctg tgcanctacg cacctcaaca   600
gcacagggtg gcagcaaaaa aaccactta ctttgggaca aacaaaaact nggggggca    660
accccggcac cccnanggg gttaacagga ancnggggaa cntgaaccc aattnaggca    720
```

| ggcccnccac cccnaatntt gctgggaaat ttttcctccc ctaaattntt tc | 772 |

<210> SEQ ID NO 12
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 12

| gccccaattc cagctgccac accacccacg gtgactgcat tagttcggat gtcatacaaa | 60 |
| agctgattga agcaaccctc tactttttgg tcgtgagcct tttgcttggt gcaggtttca | 120 |
| ttggctgtgt tggtgacgtt gtcattgcaa cagaatgggg gaaaggcact gttctctttg | 180 |
| aagtanggtg agtcctcaaa atccgtatag ttggtgaagc cacagcactt gagcccttc | 240 |
| atggtggtgt tccacacttg agtgaagtct tcctgggaac cataatcttt cttgatggca | 300 |
| ggcactacca gcaacgtcag ggaagtgctc agccattgtg gtgtacacca aggcgaccac | 360 |
| agcagctgcn acctcagcaa tgaagatgan gaggangatg aagaagaacg tcncgagggc | 420 |
| acacttgctc tcagtcttan caccatanca gcccntgaaa accaananca aagaccacna | 480 |
| cnccggctgc gatgaagaaa tnaccccncg ttgacaaact tgcatggcac tgggancccac | 540 |
| agtggcccna aaaatcttca aaaggatgc cccatcnatt gaccccccaa atgcccactg | 600 |
| ccaacagggg ctgccccacn cncnnaacga tgancccatt gnacaagatc tncntggtct | 660 |
| tnatnaacnt gaaccctgcn tngtggctcc tgttcaggnc cnnggcctga cttctnaann | 720 |
| aangaactcn gaagncccca cnggananc g | 751 |

<210> SEQ ID NO 13
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 13

| gagccaggcg tccctctgcc tgcccactca gtggcaacac ccgggagctg ttttgtcctt | 60 |
| tgtggancct cagcagtncc ctctttcaga actcantgcc aaganccctg aacaggagcc | 120 |
| accatgcagt gcttcagctt cattaagacc atgatgatcc tcttcaattt gctcatcttt | 180 |
| ctgtgtggtg cagccctgtt ggcagtgggc atctgggtgt caatcgatgg ggcatccttt | 240 |
| ctgaagatct tcgggccact gtcgtccagt gccatgcagt ttgtcaacgt gggctacttc | 300 |
| ctcatcgcag ccggcgttgt ggtcttagct ctaggtttcc tgggctgcta tggtgctaag | 360 |
| actgagagca agtgtgccct cgtgacgttc ttcttcatcc tcctcctcat cttcattgct | 420 |
| gaggttgcaa tgctgtggtc gccttggtgt acaccacaat ggctgagcac ttcctgacgt | 480 |
| tgctggtaat gcctgccatc aanaaaagat tatgggttcc caggaanact tcactcaagt | 540 |
| gttggaacac caccatgaaa gggctcaagt gctgtggctt cnnccaacta tacggatttt | 600 |
| gaagantcac ctacttcaaa gaaaanagtg cctttccccc atttctgttg caattgacaa | 660 |
| acgtccccaa cacagccaat tgaaaacctg cacccaaccc aaangggtcc ccaaccanaa | 720 |
| attnaaggg | 729 |

<210> SEQ ID NO 14
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 14

| | | | | | |
|---|---|---|---|---|---|
| tgctcttcct | caaagttgtt | cttgttgcca | taacaaccac | cataggtaaa | gcgggcgcag | 60 |
| tgttcgctga | aggggttgta | gtaccagcgc | gggatgctct | ccttgcagag | tcctgtgtct | 120 |
| ggcaggtcca | cgcagtgccc | tttgtcactg | gggaaatgga | tgcgctggag | ctcgtcaaag | 180 |
| ccactcgtgt | atttttcaca | ggcagcctcg | tccgacgcgt | cggggcagtt | gggggtgtct | 240 |
| tcacactcca | ggaaactgtc | natgcagcag | ccattgctgc | agcggaactg | ggtgggctga | 300 |
| cangtgccag | agcacactgg | atggcgcctt | tccatgnnan | gggccctgng | gaaagtccc | 360 |
| tganccccan | anctgcctct | caaangcccc | accttgcaca | ccccgacagg | ctagaatgga | 420 |
| atcttcttcc | cgaaaggtag | ttnttcttgt | tgcccaaacc | anccccntaa | acaaactctt | 480 |
| gcanatctgc | tccgnggggg | tcntantacc | ancgtgggaa | agaaccccca | ggcngcgaac | 540 |
| caancttgtt | tggatncgaa | gcnataatct | nctnttctgc | ttggtggaca | gcaccantna | 600 |
| ctgtnnanct | ttagnccntg | gtcctcntgg | gttgnncttg | aacctaatcn | ccnntcaact | 660 |
| gggacaaggt | aantngccnt | cctttnaatt | cccnancntn | cccctggtt | tgggttttn | 720 |
| cncnctccta | ccccagaaan | nccgtgttcc | ccccaacta | ggggccnaaa | ccnttnttc | 780 |
| cacaaccctn | ccccacccac | gggttcngnt | ggttng | | | 816 |

<210> SEQ ID NO 15
<211> LENGTH: 783
<212> TYPE: DNA
<213> ORGANISM: Homo sapien
<220> FEATURE:
<221> NAME/KEY: misc_feature
<222> LOCATION: (1)...(783)
<223> OTHER INFORMATION: n = A,T,C or G

<400> SEQUENCE: 15

| | | | | | |
|---|---|---|---|---|---|
| ccaaggcctg | ggcaggcata | nacttgaagg | tacaacccca | ggaacccctg | gtgctgaagg | 60 |
| atgtggaaaa | cacagattgg | cgcctactgc | ggggtgacac | ggatgtcagg | gtagagagga | 120 |
| aagacccaaa | ccaggtggaa | ctgtggggac | tcaaggaang | cacctacctg | ttccagctga | 180 |
| cagtgactag | ctcagaccac | ccagaggaca | cggccaacgt | cacagtcact | gtgctgtcca | 240 |
| ccaagcagac | agaagactac | tgcctcgcat | ccaacaangt | gggtcgctgc | cggggctctt | 300 |
| tcccacgctg | gtactatgac | cccacggagc | agatctgcaa | gagtttcgtt | tatggaggct | 360 |
| gcttgggcaa | caagaacaac | taccttcggg | aagaagagtg | cattctancc | tgtcngggtg | 420 |
| tgcaaggtgg | gccttttgana | ngcanctctg | gggctcangc | gactttcccc | cagggcccct | 480 |
| ccatggaaag | gcgccatcca | ntgttctctg | gcacctgtca | gcccacccag | ttccgctgca | 540 |
| ncaatggctg | ctgcatcnac | antttcctng | aattgtgaca | acaccccca | ntgccccaa | 600 |
| ccctcccaac | aaagcttccc | tgttnaaaaa | tacnccantt | ggcttttnac | aaacnccgg | 660 |
| cncctccntt | ttccccnntn | aacaagggc | nctngcnttt | gaactgcccn | aacccnggaa | 720 |
| tctnccnngg | aaaaantncc | ccccctggtt | cctnnaancc | cctccncnaa | anctnccccc | 780 |
| ccc | | | | | | 783 |

```
<210> SEQ ID NO 16
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 16
gccccaattc cagctgccac accacccacg gtgactgcat tagttcggat gtcatacaaa      60
agctgattga agcaaccctc tacttttttgg tcgtgagcct tttgcttggt gcaggtttca    120
ttggctgtgt tggtgacgtt gtcattgcaa cagaatgggg gaaaggcact gttctctttg    180
aagtagggtg agtcctcaaa atccgtatag ttggtgaagc cacagcactt gagcccttttc   240
atggtggtgt tccacacttg agtgaagtct tcctgggaac cataatcttt cttgatggca    300
ggcactacca gcaacgtcag gaagtgctca gccattgtgg tgtacaccaa ggcgaccaca    360
gcagctgcaa cctcagcaat gaagatgagg aggaggatga agaagaacgt cncgagggca    420
cacttgctct ccgtcttagc accatagcag cccangaaac caagagcaaa gaccacaacg    480
ccngctgcga atgaaagaaa ntacccacgt tgacaaactg catggccact ggacgacagt    540
tggcccgaan atcttcagaa aagggatgcc ccatcgattg aacacccana tgcccactgc    600
cnacagggct gcnccncncn gaaagaatga gccattgaag aaggatcntc ntggtcttaa    660
tgaactgaaa ccntgcatgg tggcccctgt tcagggctct tggcagtgaa ttctganaaa    720
aaggaacngc ntnagccccc ccaaangana aaacacccccc gggtgttgcc ctgaattggc   780
ggccaaggan ccctgccccn g                                              801

<210> SEQ ID NO 17
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 17
gtgagagcca ggcgtccctc tgcctgccca ctcagtggca acacccggga gctgttttgt      60
cctttgtgga gcctcagcag ttccctcttt cagaactcac tgccaagagc cctgaacagg    120
agccaccatg cagtgcttca gcttcattaa gaccatgatg atcctcttca atttgctcat    180
ctttctgtgt ggtgcagccc tgttggcagt gggcatctgg gtgtcaatcg atggggcatc    240
ctttctgaag atcttcgggc cactgtcgtc cagtgccatg cagtttgtca acgtgggcta    300
cttcctcatc gcagccggcg ttgtggtctt tgctcttggt ttcctgggct gctatggtgc    360
taagacggag agcaagtgtg ccctcgtgac gttcttcttc atcctcctcc tcatcttcat    420
tgctgaagtt gcagctgctg tggtcgcctt ggtgtacacc acaatggctg aaccattcct    480
gacgttgctg gtantgcctg ccatcaanaa agattatggg ttcccaggaa aaattcactc    540
aantntggaa caccnccatg aaaagggctc caatttctgn tggcttcccc aactataccg    600
gaattttgaa aganntcnccc tacttccaaa aaaaaanant tgcctttncc cccnttctgt   660
tgcaatgaaa acntcccaan acngccaatn aaaacctgcc cnnncaaaaa ggntcncaaa   720
caaaaaaant nnaagggttn                                                740
```

<210> SEQ ID NO 18
<211> LENGTH: 802
<212> TYPE: DNA
<213> ORGANISM: Homo sapien
<220> FEATURE:
<221> NAME/KEY: misc_feature
<222> LOCATION: (1)...(802)
<223> OTHER INFORMATION: n = A,T,C or G

<400> SEQUENCE: 18

| | | | | | |
|---|---|---|---|---|---|
| ccgctggttg | cgctggtcca | gngnagccac | gaagcacgtc | agcatacaca | gcctcaatca | 60 |
| caaggtcttc | cagctgccgc | acattacgca | gggcaagagc | ctccagcaac | actgcatatg | 120 |
| ggatacactt | tactttagca | gccagggtga | caactgagag | gtgtcgaagc | ttattcttct | 180 |
| gagcctctgt | tagtggagga | agattccggg | cttcagctaa | gtagtcagcg | tatgtcccat | 240 |
| aagcaaacac | tgtgagcagc | cggaaggtag | aggcaaagtc | actctcagcc | agctctctaa | 300 |
| cattgggcat | gtccagcagt | tctccaaaca | cgtagacacc | agnggcctcc | agcacctgat | 360 |
| ggatgagtgt | ggccagcgct | gcccccttgg | ccgacttggc | taggagcaga | aattgctcct | 420 |
| ggttctgccc | tgtcaccttc | acttccgcac | tcatcactgc | actgagtgtg | ggggacttgg | 480 |
| gctcaggatg | tccagagacg | tggttccgcc | ccctcnctta | atgacaccgn | ccanncaacc | 540 |
| gtcggctccc | gccgantgng | ttcgtcgtnc | ctgggtcagg | gtctgctggc | cnctacttgc | 600 |
| aancttcgtc | nggcccatgg | aattcaccnc | accggaactn | gtangatcca | ctnnttctat | 660 |
| aaccggncgc | caccgcnnnt | ggaactccac | tcttnttncc | tttacttgag | ggttaaggtc | 720 |
| acccttnncg | ttaccttggt | ccaaaccntn | ccntgtgtcg | anatngtnaa | tcnggnccna | 780 |
| tnccanccnc | atangaagcc | ng | | | | 802 |

<210> SEQ ID NO 19
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 19

| | | | | | |
|---|---|---|---|---|---|
| cnaagcttcc | aggtnacggg | ccgcnaancc | tgacccnagg | tancanaang | cagncngcgg | 60 |
| gagcccaccg | tcacgngggng | gngtctttat | nggagggggc | ggagccacat | cnctggacnt | 120 |
| cntgacccca | actcccncc | ncncantgca | gtgatgagtg | cagaactgaa | ggtnacgtgg | 180 |
| caggaaccaa | gancaaannc | tgctccnntc | caagtcggcn | naggggcgg | ggctggccac | 240 |
| gcncatccnt | cnagtgctgn | aaagcccnn | cctgtctact | tgtttggaga | acngcnnnga | 300 |
| catgcccagn | gttanataac | nggcngagag | tnantttgcc | tctcccttcc | ggctgcgcan | 360 |
| cgngtntgct | tagnggacat | aacctgacta | cttaactgaa | cccnngaatc | tnccnccct | 420 |
| ccactaagct | cagaacaaaa | aacttcgaca | ccactcantt | gtcacctgnc | tgctcaagta | 480 |
| aagtgtaccc | catncccaat | gtntgctnga | ngctctgncc | tgcnttangt | tcggtcctgg | 540 |
| gaagacctat | caattnaagc | tatgtttctg | actgcctctt | gctccctgna | acaancnacc | 600 |
| cnncnntcca | aggggggnc | ggcccccaat | cccccaacc | ntnaattnan | tttanccccn | 660 |
| ccccnggcc | cggccttta | cnancntcnn | nnacnggna | aaaccnnngc | tttncccaac | 720 |
| nnaatccncc | t | | | | | 731 |

<210> SEQ ID NO 20

<211> LENGTH: 754
<212> TYPE: DNA
<213> ORGANISM: Homo sapien
<220> FEATURE:
<221> NAME/KEY: misc_feature
<222> LOCATION: (1)...(754)
<223> OTHER INFORMATION: n = A,T,C or G

<400> SEQUENCE: 20

```
ttttttttt ttttttttt taaaaacccc ctccattnaa tgnaaacttc cgaaattgtc      60
caacccctc ntccaaatnn ccntttccgg gnggggttc caaacccaan ttannttttgg    120
annttaaatt aaatnttnnt tggnggnnna anccnaatgt nangaaagtt naacccanta    180
tnancttnaa tncctggaaa ccngtngntt ccaaaaatnt ttaaccctta antccctccg    240
aaatngttna nggaaaaccc aanttctcnt aaggttgttt gaaggntnaa tnaaaanccc    300
nnccaattgt ttttngccac gcctgaatta attggnttcc gntgttttcc nttaaaanaa    360
ggnnancccc ggttantnaa tccccccnnc cccaattata ccganttttt ttngaattgg    420
ganccncgg gaattaacgg ggnnnntccc tnttggggggg cnggnncccc ccccntcggg    480
ggttngggnc aggncnnaat tgtttaaggg tccgaaaaat ccctccnaga aaaaanctc    540
ccaggntgag nntngggttt ncccccccc canggcccct ctcgnanagt tgggggttttgg   600
ggggcctggg atttttntttc ccctnttncc tccccccccc ccgggganag aggttngngt   660
tttgntcnc ggccccnccn aagancttttn ccganttnan ttaaatcccnt gcctnggcga    720
agtccnttgn agggntaaan ggccccctnn cggg                                754
```

<210> SEQ ID NO 21
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 21

```
atcancccat gaccccnaac nngggaccnc tcanccggnc nnncnaccnc cggccnatca      60
nngtnagnnc actncnnttn natcacnccc cnccnactac gcccncnanc cnacgcncta    120
nncanatncc actgannggcg cgangtngan ngagaaanct nataccanag ncaccanacn    180
ccagctgtcc nanaangcct nnnatacngg nnnatccaat ntgnanccctc cnaagtattn    240
nncnncanat gattttcctn anccgattac ccntncccccc tanccccctcc ccccaacna    300
cgaaggcnct ggnccnaagg nngcgncncc ccgctagntc cccnncaagt cncncnccta    360
aactcanccn nattacncgc ttcntgagta tcactccccg aatctcaccc tactcaactc    420
aaaaanatcn gatacaaaat aatncaagcc tgnttatnac actntgactg ggtctctatt    480
ttagnggtcc ntnaancntc ctaatacttc cagtctncct tcnccaatttt ccnaanggct    540
ctttcngaca gcatntttttg gttcccnnntt gggttcttan ngaattgccc ttcntngaac    600
gggctcntct tttccttcgg ttancctggn ttcnnccggc cagttattatt ttcccnttttt    660
aaattcntnc cntttantttt tggcnttcna accccccggc cttgaaaacg gcccccctggt    720
aaaaggttgt tttganaaaa ttttttgtttt gttcc                              755
```

<210> SEQ ID NO 22
<211> LENGTH: 849
<212> TYPE: DNA
<213> ORGANISM: Homo sapien
<220> FEATURE:
<221> NAME/KEY: misc_feature
<222> LOCATION: (1)...(849)
<223> OTHER INFORMATION: n = A,T,C or G

<400> SEQUENCE: 22

| | | | | | |
|---|---|---|---|---|---|
| tttttttttt | ttttangtg | tngtcgtgca | ggtagaggct | tactacaant | gtgaanacgt | 60 |
| acgctnggan | taangcgacc | cganttctag | ganncnccct | aaaatcanac | tgtgaagatn | 120 |
| atcctgnnna | cggaanggtc | accggnngat | nntgctaggg | tgnccnctcc | cannncnttn | 180 |
| cataactcng | nggccctgcc | caccaccttc | ggcggcccng | ngnccgggcc | cgggtcattn | 240 |
| gnnttaaccn | cactnngcna | ncggtttccn | nccccnncng | acccnggcga | tccggggtnc | 300 |
| tctgtcttcc | cctgnagncn | anaaantggg | ccncggnccc | ctttacccct | nnacaagcca | 360 |
| cngccntcta | nccncngccc | ccctccant | nngggggact | gccnanngct | ccgttnctng | 420 |
| nnaccccnnn | gggtncctcg | gttgtcgant | cnaccgnang | ccanggattc | cnaaggaagg | 480 |
| tgcgttnttg | gccctaccc | ttcgctncgg | nncacccttc | ccgacnanga | nccgctcccg | 540 |
| cncnncgnng | cctcncctcg | caacacccgc | nctcntcngt | ncggnnnccc | ccccacccgc | 600 |
| nccctcncnc | ngncgnancn | ctccncncc | gtctcannca | ccaccccgcc | ccgccaggcc | 660 |
| ntcanccacn | ggnngacnng | nagcncnntc | gcnccgcgcn | gcgncccct | cgccncngaa | 720 |
| ctncntcngg | ccantnncgc | tcaanccnna | cnaaacgccg | ctgcgcggcc | cgnagcgncc | 780 |
| ncctccncga | gtcctcccgn | cttccnaccc | angnnttccn | cgaggacacn | nnaccccgcc | 840 |
| nncangcgg | | | | | | 849 |

<210> SEQ ID NO 23
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 23

| | | | | | |
|---|---|---|---|---|---|
| gcgcaaacta | tacttcgctc | gnactcgtgc | gcctcgctnc | tcttttcctc | cgcaaccatg | 60 |
| tctgacnanc | ccgattnggc | ngatatcnan | aagntcganc | agtccaaact | gantaacaca | 120 |
| cacacncnan | aganaaatcc | nctgccttcc | anagtanacn | attgaacnng | agaaccangc | 180 |
| nggcgaatcg | taatnaggcg | tgcgccgcca | atntgtcncc | gtttattntn | ccagcntcnc | 240 |
| ctnccnaccc | tacntcttcn | nagctgtcnn | accctngtn | cgnaccccc | naggtcggga | 300 |
| tcgggttnn | nntgaccgng | cnnccctcc | ccnntccat | nacgancnc | ccgcaccacc | 360 |
| nanngcncgc | nccccgnnct | cttcgccncc | ctgtcctntn | ccctgtngc | ctggcncngn | 420 |
| accgcattga | ccctcgccnn | ctncnngaaa | ncgnanacgt | ccgggttgnn | anancgctg | 480 |
| tgggnnngcg | tctgcnccgc | gttccttccn | ncnncttcca | ccatcttcnt | tacngggtct | 540 |
| ccncgcctc | tcnncacnc | cctgggacgc | tntcctntgc | cccccttnac | tcccccctt | 600 |
| cgncgtgncc | cgncccacc | ntcatttnca | nacgntcttc | acaannncct | ggntnnctcc | 660 |
| cnancngncn | gtcanccnag | ggaaggnggg | ggnnccnntg | nttgacgttg | ngngangtc | 720 |
| cgaanantcc | tcnccntcan | cnctacccct | cgggcgnnct | ctcngttncc | aacttancaa | 780 |
| ntctcccccg | ngngcncntc | tcagcctcnc | ccncccncct | ctctgcantg | tnctctgctc | 840 |
| tnaccnntac | gantnttcgn | cnccctcttt | cc | | | 872 |

<210> SEQ ID NO 24
<211> LENGTH: 815
<212> TYPE: DNA
<213> ORGANISM: Homo sapien
<220> FEATURE:
<221> NAME/KEY: misc_feature
<222> LOCATION: (1)...(815)
<223> OTHER INFORMATION: n = A,T,C or G

<400> SEQUENCE: 24

| | | | | | |
|---|---|---|---|---|---|
| gcatgcaagc | ttgagtattc | tatagngtca | cctaaatanc | ttggcntaat | catggtcnta | 60 |
| nctgncttcc | tgtgtcaaat | gtatacnaan | tanatatgaa | tctnatntga | caagannqta | 120 |
| tcntncatta | gtaacaantg | tnntgtccat | cctgtcngan | canattccca | tnnattncgn | 180 |
| cgcattcncn | gcncantatn | taatngggaa | ntcnnntnnn | ncaccnncat | ctatcntncc | 240 |
| gcncctgac | tggnagagat | ggatnantc | tnntntgacc | nacatgttca | tcttggattn | 300 |
| aanancccc | cgcngnccac | cggttngnng | cnagccnntc | ccaagacctc | ctgtggaggt | 360 |
| aacctgcgtc | aganncatca | aacntgggaa | acccgcnncc | angtnnaagt | ngnnncanan | 420 |
| gatcccgtcc | aggnttnacc | atcccttcnc | agcgcccct | ttngtgcctt | anagngnagc | 480 |
| gtgtccnanc | cnctcaacat | ganacgcgcc | agnccanccg | caattnggca | caatgtcgnc | 540 |
| gaaccccta | ggggantna | tncaaancc | caggattgtc | cncncangaa | atcccncanc | 600 |
| cccncctac | ccnnctttgg | gacngtgacc | aantcccgga | gtnccagtcc | ggccngnctc | 660 |
| ccccaccggt | nnccntgggg | gggtgaanct | cngnntcanc | cngncgaggn | ntcgnaagga | 720 |
| accggncctn | ggncgaanng | ancnntcnga | agngccncnt | cgtataaccc | ccctcncca | 780 |
| nccnacngnt | agntcccccc | cngggtncgg | aangg | | | 815 |

<210> SEQ ID NO 25
<211> LENGTH: 775
<212> TYPE: DNA
<213> ORGANISM: Homo sapien
<220> FEATURE:
<221> NAME/KEY: misc_feature
<222> LOCATION: (1)...(775)
<223> OTHER INFORMATION: n = A,T,C or G

<400> SEQUENCE: 25

| | | | | | |
|---|---|---|---|---|---|
| ccgagatgtc | tcgctccgtg | gccttagctg | tgctcgcgct | actctctctt | tctggcctgg | 60 |
| aggctatcca | gcgtactcca | aagattcagg | tttactcacg | tcatccagca | gagaatggaa | 120 |
| agtcaaattt | cctgaattgc | tatgtgtctg | ggtttcatcc | atccgacatt | gaanttgact | 180 |
| tactgaagaa | tgganagaga | attgaaaaag | tggagcattc | agacttgtct | ttcagcaagg | 240 |
| actggtcttt | ctatctcntg | tactacactg | aattcacccc | cactgaaaaa | gatgagtatg | 300 |
| cctgccgtgt | gaaccatgtg | actttgtcac | agcccaagat | agttaagtgg | gatcgagaca | 360 |
| tgtaagcagn | cnncatggaa | gtttgaagat | gccgcatttg | gattggatga | attccaaatt | 420 |
| ctgcttgctt | gcnttttaat | antgatatgc | ntatacaccc | taccctttat | gnccccaaat | 480 |
| tgtagggtt | acatnantgt | tcncntngga | catgatcttc | ctttataant | ccnccnttcg | 540 |
| aattgcccgt | cnccngttn | ngaatgtttc | cnnaaccacg | gttggctccc | ccaggtcncc | 600 |
| tcttacggaa | gggcctgggc | cncttttcaa | ggttggggga | accnaaaatt | tcncttntgc | 660 |
| ccncccncca | cnntcttgng | nncncanttt | ggaaccctc | cnattcccct | tggcctccna | 720 |
| nccttnncta | anaaaacttn | aaancgtngc | naaanntttn | acttccccc | ttacc | 775 |

```
<210> SEQ ID NO 26
<211> LENGTH: 820
<212> TYPE: DNA
<213> ORGANISM: Homo sapien
<220> FEATURE:
<221> NAME/KEY: misc_feature
<222> LOCATION: (1)...(820)
<223> OTHER INFORMATION: n = A,T,C or G

<400> SEQUENCE: 26
anattantac agtgtaatct tttcccagag gtgtgtanag ggaacggggc ctagaggcat      60
cccanagata ncttatanca acagtgcttt gaccaagagc tgctgggcac atttcctgca     120
gaaaaggtgg cggtccccat cactcctcct ctcccatagc catcccagag gggtgagtag     180
ccatcangcc ttcggtggga gggagtcang gaaacaacan accacagagc anacagacca     240
ntgatgacca tgggcgggag cgagcctctt ccctgnaccg gggtggcana nganagccta     300 nctgagggt cacactataa acgttaacga ccnagatnan cacctgcttc aagtgcaccc      360
ttcctacctg acnaccagng accnnnaact gcngcctggg gacagcnctg ggancagcta     420
acnnagcact cacctgcccc cccatggccg tncgcntccc tggtcctgnc aagggaagct     480
ccctgttgga attncgggga naccaaggga nccccctcct ccanctgtga aggaaaaann     540
gatggaattt tncccttccg gccnntcccc tcttcctta cacgcccct nntactcntc       600 tccctctntt ntcctgncnc acttttnacc ccnnnattc ccttnattga tcggannctn     660
ganattccac tnncgcctnc cntcnatcg naanacnaaa nactntctna cccngggat      720 gggnnccctcg ntcatcctct cttttttcnct accnccnntt ctttgcctct ccttngatca     780
tccaaccntc gntggccntn cccccccnnn tcctttnccc                            820

<210> SEQ ID NO 27
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 27
tctgggtgat ggcctcttcc tcctcaggga cctctgactg ctctgggcca agaatctct       60 tgtttcttct ccgagcccca ggcagcggtg attcagccct gcccaacctg attctgatga    120
ctgcggatgc tgtgacggac ccaaggggca aataggtgcc caggtccag ggaggggcgc      180 ctgctgagca cttccgcccc tcaccctgcc cagcccctgc catgagctct gggctgggtc    240
tccgcctcca gggttctgct cttccangca ngccancaag tggcgctggg ccacactggc    300
ttcttcctgc cccntccctg gctctgantc tctgtcttcc tgtcctgtgc angcnccttg    360
gatctcagtt tccctcnctc anngaactct gtttctgann tcttcantta actntgantt    420
tatnaccnan tggnctgtnc tgtcnnactt taatgggccn gaccggctaa tccctccctc    480
nctcccttcc anttcnnnna accngcttnc cntcntctcc cntanccgg ccngggaanc     540 ctcctttgcc ctnaccangg gccnnnaccg ccntnnctn ggggggcnng gtnnctncnc     600 ctgtnnccc cnctcncnnt tncctcgtcc cnncnncgcn nngcanntc ncgtcccnn       660 tnnctcttcn ngtntcgnaa ngtcncntn tnnnnngcn ngntnntnc tccctctcnc       720 cnnntgnang tnnttnnnnc ncngnnccc nnnncnnnn nggnnntnn tctncncngc       780 cccnnccccc ngnattaagg cctccnntct ccggccnc                             818
```

<210> SEQ ID NO 28
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 28

| | | | | | |
|---|---|---|---|---|---|
| aggaagggcg | gagggatatt | gtangggatt | gagggatagg | agnataangg | gggaggtgtg | 60 |
| tcccaacatg | anggtgnngt | tctcttttga | angaggggttg | ngtttttann | ccnggtgggt | 120 |
| gattnaaccc | cattgtatgg | agnnaaaggn | tttnagggat | ttttcggctc | ttatcagtat | 180 |
| ntanattcct | gtnaatcgga | aaatnatntt | tcnncnggaa | aatnttgctc | ccatccgnaa | 240 |
| attnctcccg | ggtagtgcat | nttnggggggn | cngccangtt | tcccaggctg | ctanaatcgt | 300 |
| actaaagntt | naagtgggan | tncaaatgaa | aacctnncac | agagnatccn | tacccgactg | 360 |
| tnnnttncct | tcgccctntg | actctgcnng | agcccaatac | ccnngngnat | gtcnccccngn | 420 |
| nnngcgncnc | tgaaannnnc | tcgnggctnn | gancatcang | gggtttcgca | tcaaaagcnn | 480 |
| cgtttcncat | naaggcactt | tngcctcatc | caaccnctng | ccctcnncca | tttngccgtc | 540 |
| nggttcncct | acgctnntg | cncctnnntn | ganattttnc | ccgcctnggg | naancctcct | 600 |
| gnaatgggta | gggncttntc | ttttnaccnn | gnggtntact | aatcnnctnc | acgcntnctt | 660 |
| tctcnacccc | cccccttttt | caatcccanc | ggcnaatggg | gtctccccnn | cganggggggg | 720 |
| nnncccannc | c | | | | | 731 |

<210> SEQ ID NO 29
<211> LENGTH: 822
<212> TYPE: DNA
<213> ORGANISM: Homo sapien
<220> FEATURE:
<221> NAME/KEY: misc_feature
<222> LOCATION: (1)...(822)
<223> OTHER INFORMATION: n = A,T,C or G

<400> SEQUENCE: 29

| | | | | | |
|---|---|---|---|---|---|
| actagtccag | tgtggtggaa | ttccattgtg | ttggggncnc | ttctatgant | antnttagat | 60 |
| cgctcanacc | tcacanccctc | ccnacnangc | ctataangaa | nannaataga | nctgtncnnt | 120 |
| atntntacnc | tcatanncct | cnnnacccac | tccctcttaa | cccntactgt | gcctatngcn | 180 |
| tnnctantct | ntgccgcctn | cnanccaccn | gtgggccnac | cncnngnatt | ctcnatctcc | 240 |
| tcnccatntn | gcctananta | ngtncatacc | ctatacctac | nccaatgcta | nnnctaancn | 300 |
| tccatnantt | annntaacta | ccactgacnt | ngactttcnc | atnanctcct | aatttgaatc | 360 |
| tactctgact | cccacngcct | annnattagc | ancntcccc | nacnatntct | caaccaaatc | 420 |
| ntcaacaacc | tatctanctg | ttcnccaacc | nttncctccg | atcccnnac | aaccccctc | 480 |
| ccaaatacccc | nccacctgac | ncctaaccccn | caccatcccg | gcaagccnan | ggcatttan | 540 |
| ccactggaat | cacnatngga | naaaaaaaac | ccnaactctc | tancncnnat | ctccctaana | 600 |
| aatnctcctn | naatttactn | ncantnccat | caanccccacn | tgaaacnnaa | cccctgtttt | 660 |
| tanatcccctt | ctttcgaaaa | ccnaccccttt | annncccaac | ctttngggcc | cccccnctnc | 720 |
| ccnaatgaag | gncncccaat | cnangaaacg | nccntgaaaa | ancnaggcna | ananntccg | 780 |
| canatcctat | cccttanttn | ggggncccctt | ncccngggcc | cc | | 822 |

<210> SEQ ID NO 30
<211> LENGTH: 787
<212> TYPE: DNA
<213> ORGANISM: Homo sapien
<220> FEATURE:
<221> NAME/KEY: misc_feature
<222> LOCATION: (1)...(787)
<223> OTHER INFORMATION: n = A,T,C or G

<400> SEQUENCE: 30

| | | | | |
|---|---|---|---|---|
| cggccgcctg | ctctggcaca | tgcctcctga | atggcatcaa | aagtgatgga | ctgcccattg | 60 |
| ctagagaaga | ccttctctcc | tactgtcatt | atggagccct | gcagactgag | ggctcccctt | 120 |
| gtctgcagga | tttgatgtct | gaagtcgtgg | agtgtggctt | ggagctcctc | atctacatna | 180 |
| gctggaagcc | ctggagggcc | tctctcgcca | gcctcccccct | tctctccacg | ctctccangg | 240 |
| acaccagggg | ctccaggcag | cccattattc | ccagnangac | atggtgtttc | tccacgcgga | 300 |
| cccatggggc | ctgnaaggcc | agggtctcct | ttgacaccat | ctctcccgtc | ctgcctggca | 360 |
| ggccgtggga | tccactantt | ctanaacggn | cgccaccncg | gtgggagctc | cagcttttgt | 420 |
| tcccnttaat | gaaggttaat | tgcncgcttg | gcgtaatcat | nggtcanaac | tntttcctgt | 480 |
| gtgaaattgt | tntcccctc | ncnattccnc | ncnacatacn | aacccggaan | cataaagtgt | 540 |
| taaagcctgg | gggtngcctn | nngaatnaac | tnaactcaat | taattgcgtt | ggctcatggc | 600 |
| ccgctttccn | ttcnggaaaa | ctgtcntccc | ctgcnttnnt | gaatcggcca | cccccncggg | 660 |
| aaaagcggtt | tgcnttttng | ggggntcctt | ccncttcccc | cctcnctaan | ccctncgcct | 720 |
| cggtcgttnc | nggtngcggg | gaangggnat | nnnctcccnc | naaggggng | agnnngntat | 780 |
| ccccaaa | | | | | | 787 |

<210> SEQ ID NO 31
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 31

| | | | | | | |
|---|---|---|---|---|---|---|
| tttttttttt | tttttttggc | gatgctactg | tttaattgca | ggaggtgggg | gtgtgtgtac | 60 |
| catgtaccag | ggctattaga | agcaagaagg | aaggagggag | ggcagagcgc | cctgctgagc | 120 |
| aacaaaggac | tcctgcagcc | ttctctgtct | gtctcttggc | gcaggcacat | ggggaggcct | 180 |
| cccgcagggt | gggggccacc | agtccagggg | tgggagcact | acanggggtg | ggagtgggtg | 240 |
| gtggctggtn | cnaatggcct | gncacanatc | cctacgattc | ttgacacctg | gatttcacca | 300 |
| ggggaccttc | tgttctccca | nggnaacttc | ntnnatctcn | aaagaacaca | actgtttctt | 360 |
| cngcanttct | ggctgttcat | ggaaagcaca | ggtgtccnat | ttnggctggg | acttggtaca | 420 |
| tatggttccg | gcccacctct | cccntcnaan | aagtaattca | cccccccccn | cntctnttg | 480 |
| cctgggccct | taantaccca | caccggaact | canttantta | ttcatcttng | gntgggcttg | 540 |
| ntnatcnccn | cctgaangcg | ccaagttgaa | aggccacgcc | gtnccncctc | cccatagnan | 600 |
| nttttnncnt | canctaatgc | ccccccnggc | aacnatccaa | tcccccccccn | tggggcccc | 660 |
| agcccanggc | ccccgnctcg | ggnnccngn | cncgnantcc | ccaggntctc | ccantcngnc | 720 |
| ccnnngcncc | cccgcacgca | gaacanaagg | ntngagccnc | cgcannnnnn | nggtnncnac | 780 |
| ctcgccccccc | ccnncgnng | | | | | 799 |

<210> SEQ ID NO 32
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 32

| | | | | | | |
|---|---|---|---|---|---|---|
| tttttttttt | tttttttttt | tttttttttt | tttttttttt | tttttttttt | tttttttttt | 60 |
| ttttnccnag | ggcaggttta | ttgacaacct | cncgggacac | aancaggctg | gggacaggac | 120 |
| ggcaacaggc | tccggcggcg | gcggcggcgg | ccctacctgc | ggtaccaaat | ntgcagcctc | 180 |
| cgctcccgct | tgatnttcct | ctgcagctgc | aggatgcent | aaaacagggc | ctcggccntn | 240 |
| ggtgggcacc | ctgggatttn | aatttccacg | ggcacaatgc | ggtcgcancc | cctcaccacc | 300 |
| nattaggaat | agtggtntta | cccnccnccg | ttggcncact | ccccntggaa | accacttntc | 360 |
| gcggctccgg | catctggtct | taaaccttgc | aaacnctggg | gccctcttt | tggttantnt | 420 |
| nccngccaca | atcatnactc | agactggcnc | gggctggccc | caaaaaancn | ccccaaaacc | 480 |
| ggnccatgtc | ttnncggggt | tgctgcnatn | tncatcacct | cccgggcnca | ncaggncaac | 540 |
| ccaaaagttc | ttgnggcccn | caaaaaanct | ccggggggnc | ccagtttcaa | caaagtcatc | 600 |
| cccttggcc | cccaaatcct | cccccgntt | nctgggtttg | ggaacccacg | cctctnnctt | 660 |
| tggnnggcaa | gntggntccc | ccttcgggcc | cccggtgggc | ccnnctctaa | ngaaaacncc | 720 |
| ntcctnnnca | ccatccccc | nngnnacgnc | tancaangna | tccctttttt | tanaaacggg | 780 |
| ccccccncg | | | | | | 789 |

<210> SEQ ID NO 33
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 33

| | | | | | | |
|---|---|---|---|---|---|---|
| gacagaacat | gttggatggt | ggagcacctt | tctatacgac | ttacaggaca | gcagatgggg | 60 |
| aattcatggc | tgttggagca | atanaacccc | agttctacga | gctgctgatc | aaaggacttg | 120 |
| gactaaagtc | tgatgaactt | cccaatcaga | tgagcatgga | tgattggcca | gaaatgaana | 180 |
| agaagtttgc | agatgtattt | gcaaagaaga | cgaaggcaga | gtggtgtcaa | atctttgacg | 240 |
| gcacagatgc | ctgtgtgact | ccggttctga | cttttgagga | ggttgttcat | catgatcaca | 300 |
| acaangaacg | gggctcgttt | atcaccantg | aggagcagga | cgtgagcccc | cgccctgcac | 360 |
| ctctgctgtt | aaacacccca | gccatccctt | ctttcaaaag | ggatccacta | cttctagagc | 420 |
| ggncgccacc | gcgtggagc | tccagctttt | gttcccttta | gtgagggtta | attgcgcgct | 480 |
| tggcgtaatc | atggtcatan | ctgtttcctg | tgtgaaattg | ttatccgctc | acaattccac | 540 |
| acaacatacg | anccggaagc | atnaaatttt | aaagcctggn | ggtngcctaa | tgantgaact | 600 |
| nactcacatt | aattggcttt | gcgctcactg | cccgctttcc | agtccggaaa | acctgtcctt | 660 |
| gccagctgcc | nttaatgaat | cnggccaccc | ccgggggaaa | aggcngtttg | cttnttgggg | 720 |
| cgcncttccc | gctttctcgc | ttcctgaant | ccttcccccc | ggtctttcgg | cttgcggcna | 780 |
| acggtatcna | cct | | | | | 793 |

<210> SEQ ID NO 34
<211> LENGTH: 756
<212> TYPE: DNA
<213> ORGANISM: Homo sapien
<220> FEATURE:
<221> NAME/KEY: misc_feature
<222> LOCATION: (1)...(756)
<223> OTHER INFORMATION: n = A,T,C or G

<400> SEQUENCE: 34

| gccgcgaccg gcatgtacga gcaactcaag ggcgagtgga accgtaaaag ccccaatctt | 60 |
| ancaagtgcg gggaanagct gggtcgactc aagctagttc ttctggagct caacttcttg | 120 |
| ccaaccacag ggaccaagct gaccaaacag cagctaattc tggcccgtga catactggag | 180 |
| atcggggccc aatggagcat cctacgcaan gacatcccct ccttcgagcg ctacatggcc | 240 |
| cagctcaaat gctactactt tgattacaan gagcagctcc ccgagtcagc ctatatgcac | 300 |
| cagctcttgg gcctcaacct cctcttcctg ctgtcccaga accgggtggc tgantnccac | 360 |
| acgganttgg ancggctgcc tgcccaanga catacanacc aatgtctaca tcnaccacca | 420 |
| gtgtcctgga gcaatactga tgganggcag ctaccncaaa gtnttcctgg ccnagggtaa | 480 |
| catcccccgc cgagagctac accttcttca ttgacatcct gctcgacact atcagggatg | 540 |
| aaaatcgcng ggttgctcca gaaaggctnc aanaanatcc ttttcnctga aggccccgg | 600 |
| atncnctagt nctagaatcg gcccgccatc gcggtgganc ctccaacctt tcgtttnccct | 660 |
| ttactgaggg ttnattgccg cccttggcgt tatcatggtc acnccngttn cctgtgttga | 720 |
| aattnttaac cccccacaat tccacgccna cattng | 756 |

<210> SEQ ID NO 35
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 35

| ggggatctct anatcnacct gnatgcatgg ttgtcggtgt ggtcgctgtc gatgaanatg | 60 |
| aacaggatct tgcccttgaa gctctcggct gctgtnttta agttgctcag tctgccgtca | 120 |
| tagtcagaca cnctcttggg caaaaaacan caggatntga gtcttgattt cacctccaat | 180 |
| aatcttcngg gctgtctgct cggtgaactc gatgacnang gcagctggt tgtgtntgat | 240 |
| aaantccanc angttctcct tggtgacctc cccttcaaag ttgttccggc cttcatcaaa | 300 |
| cttctnnaan angannancc canctttgtc gagctggnat ttggcannaaca cgtcactgtt | 360 |
| ggaaactgat cccaaatggt atgtcatcca tcgcctctgc tgcctgcaaa aaacttgctt | 420 |
| ggcncaaatc cgactccccn tccttgaaag aagccnatca caccccctc cctggactcc | 480 |
| nncaangact ctnccgctnc cccntccnng cagggttggt ggcannccgg gcccntgcgc | 540 |
| ttcttcagcc agttcacnat nttcatcagc ccctctgcca gctgtttnat tccttggggg | 600 |
| ggaaccgtc tctcccttcc tgaannaact ttgaccgtng gaatagccgc gcntcnccnt | 660 |
| acntnctggg ccgggttcaa antccctccn ttgncnntcn cctcgggcca ttctggattt | 720 |
| nccnaacttt ttccttcccc cnccccncgg ngtttggntt tttcatnggg ccccaactct | 780 |
| gctnttggcc antcccctgg gggcntntan cnccccctnt ggtcccntng ggcc | 834 |

<210> SEQ ID NO 36
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 36

| | | | | | |
|---|---|---|---|---|---|
| cggncgcttt | ccngccgcgc | cccgtttcca | tgacnaaggc | tcccttcang | ttaaatacnn | 60 |
| cctagnaaac | attaatgggt | tgctctacta | atacatcata | cnaaccagta | agcctgccca | 120 |
| naacgccaac | tcaggccatt | cctaccaaag | gaagaaaggc | tggtctctcc | accccctgta | 180 |
| ggaaaggcct | gccttgtaag | acaccacaat | ncggctgaat | ctnaagtctt | gtgttttact | 240 |
| aatggaaaaa | aaaaataaac | aanaggtttt | gttctcatgg | ctgcccaccg | cagcctggca | 300 |
| ctaaaacanc | ccagcgctca | cttctgcttg | ganaaatatt | ctttgctctt | ttggacatca | 360 |
| ggcttgatgg | tatcactgcc | acntttccac | ccagctgggc | nccnttcccc | catntttgtc | 420 |
| antganctgg | aaggcctgaa | ncttagtctc | caaaagtctc | ngcccacaag | accggccacc | 480 |
| agggangtc | ntttncagtg | gatctgccaa | anantacccn | tatcatcnnt | gaataaaaag | 540 |
| gccctgaac | ganatgcttc | cancanccct | taagacccca | aatcctngaa | ccatggtgcc | 600 |
| cttccggtct | gatccnaaag | gaatgttcct | gggtcccant | ccctcctttg | ttncttacgt | 660 |
| tgtnttggac | ccntgctngn | atnacccaan | tganatcccc | ngaagcaccc | tnccctggc | 720 |
| atttganttt | cntaaattct | ctgccctacn | nctgaaagca | cnattccctn | ggcnccnaan | 780 |
| ggngaactca | agaaggtctn | ngaaaaacca | cncn | | | 814 |

<210> SEQ ID NO 37
<211> LENGTH: 760
<212> TYPE: DNA
<213> ORGANISM: Homo sapien
<220> FEATURE:
<221> NAME/KEY: misc_feature
<222> LOCATION: (1)...(760)
<223> OTHER INFORMATION: n = A,T,C or G

<400> SEQUENCE: 37

| | | | | | |
|---|---|---|---|---|---|
| gcatgctgct | cttcctcaaa | gttgttcttg | ttgccataac | aaccaccata | ggtaaagcgg | 60 |
| gcgcagtgtt | cgctgaaggg | gttgtagtac | cagcgcggga | tgctctcctt | gcagagtcct | 120 |
| gtgtctggca | ggtccacgca | atgccctttg | tcactgggga | aatggatgcg | ctggagctcg | 180 |
| tcnaaccac | tcgtgtattt | ttcacangca | gcctcctccg | aagcntccgg | gcagttgggg | 240 |
| gtgtcgtcac | actccactaa | actgtcgatn | cancagccca | ttgctgcagc | ggaactgggt | 300 |
| gggctgacag | gtgccagaac | acactggatn | ggccttttcca | tggaagggcc | tgggggaaat | 360 |
| cncctnancc | caaactgcct | ctcaaaggcc | accttgcaca | ccccgacagg | ctagaaatgc | 420 |
| actcttcttc | ccaaaggtag | ttgttcttgt | tgcccaagca | ncctccanca | aaccaaaanc | 480 |
| ttgcaaaatc | tgctccgtgg | gggtcatnnn | taccanggtt | ggggaaanaa | accggcngn | 540 |
| ganccncctt | gtttgaatgc | naaggnaata | atcctcctgt | cttgcttggg | tggaanagca | 600 |
| caattgaact | gttaacnttg | ggccgnttc | cnctngggtg | gtctgaaact | aatcaccgtc | 660 |
| actgaaaaa | ggtangtgcc | ttccttgaat | tcccaaantt | ccctngntt | tgggtnnttt | 720 |
| ctcctctncc | ctaaaaatcg | tnttccccc | ccntanggcg | | | 760 |

<210> SEQ ID NO 38
<211> LENGTH: 724
<212> TYPE: DNA
<213> ORGANISM: Homo sapien
<220> FEATURE:
<221> NAME/KEY: misc_feature
<222> LOCATION: (1)...(724)
<223> OTHER INFORMATION: n = A,T,C or G

<400> SEQUENCE: 38

| | | | | | |
|---|---|---|---|---|---|
| tttttttttt | tttttttttt | tttttttttt | ttttaaaaa | cccctccat | tgaatgaaaa | 60 |
| cttccnaaat | tgtccaaccc | cctcnnccaa | atnccattt | ccgggggggg | gttccaaacc | 120 |
| caaattaatt | ttgganttta | aattaaatnt | tnattnggggg | aanaanccaa | atgtnaagaa | 180 |
| aatttaaccc | attataact | taaatncctn | gaaacccntg | gnttccaaaa | atttttaacc | 240 |
| cttaaatccc | tccgaaattg | ntaaggaaa | accaaattcn | cctaaggctn | tttgaaggtt | 300 |
| ngatttaaac | ccccttnant | tnttttnacc | cnngnctnaa | ntatttngnt | tccggtgttt | 360 |
| tcctnttaan | cntnggtaac | tcccgntaat | gaannnccct | aaccaatta | aaccgaattt | 420 |
| tttttgaatt | ggaaattccn | nggaattna | ccggggtttt | tcccntttgg | gggccatncc | 480 |
| cccnctttcg | gggtttgggn | ntaggttgaa | tttttnnang | nccaaaaaa | nccccaana | 540 |
| aaaaaactcc | caagnnttaa | ttngaatntc | ccccttccca | ggccttttgg | gaaaggnggg | 600 |
| tttntggggg | ccngggantt | cnttccccn | ttnccnccc | cccccngt | aaangttat | 660 |
| ngnntttggt | ttttgggccc | cttnanggac | cttccggatn | gaaattaaat | ccccgggncg | 720 |
| gccg | | | | | | 724 |

<210> SEQ ID NO 39
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 39

| | | | | | |
|---|---|---|---|---|---|
| tttttttttt | tttttctttg | ctcacattta | attttattt | tgatttttt | taatgctgca | 60 |
| caacacaata | tttatttcat | ttgtttcttt | tatttcattt | tatttgtttg | ctgctgctgt | 120 |
| tttatttatt | tttactgaaa | gtgagaggga | acttttgtgg | ccttttttcc | ttttctgta | 180 |
| ggccgcctta | agctttctaa | atttggaaca | tctaagcaag | ctgaaggaa | aaggggggttt | 240 |
| cgcaaaatca | ctcgggggaa | nggaaaggtt | gctttgttaa | tcatgcccta | tggtgggtga | 300 |
| ttaactgctt | gtacaattac | ntttcacttt | taattaattg | tgctnaangc | tttaattana | 360 |
| cttgggggtt | ccctccccan | accaacccn | ctgacaaaaa | gtgccngccc | tcaaatnatg | 420 |
| tcccggcnnt | cnttgaaaca | cacngcngaa | ngttctcatt | ntccccncnc | caggtnaaaa | 480 |
| tgaagggtta | ccatntttaa | cnccacctcc | acntggcnnn | gcctgaatcc | tcnaaaancn | 540 |
| ccctcaancn | aattnctnng | cccggtcnc | gcntnngtcc | cnccccgggct | ccggaantn | 600 |
| caccccnga | anncnntnnc | naacnaaatt | ccgaaaatat | tcccnntcnc | tcaattcccc | 660 |
| cnnagactnt | cctcnncnan | cncaattttc | ttttnntcac | gaacncgnnc | cnaaaatgn | 720 |
| nnnncncctc | cnctngtccn | naatcnccan | c | | | 751 |

<210> SEQ ID NO 40
<211> LENGTH: 753
<212> TYPE: DNA

<213> ORGANISM: Homo sapien
<220> FEATURE:
<221> NAME/KEY: misc_feature
<222> LOCATION: (1)...(753)
<223> OTHER INFORMATION: n = A,T,C or G

<400> SEQUENCE: 40

| | | | | | |
|---|---|---|---|---|---|
| gtggtatttt | ctgtaagatc | aggtgttcct | ccctcgtagg | tttagaggaa | acaccctcat | 60
| agatgaaaac | cccccgaga | cagcagcact | gcaactgcca | agcagccggg | gtaggagggg | 120
| cgccctatgc | acagctgggc | ccttgagaca | gcagggcttc | gatgtcaggc | tcgatgtcaa | 180
| tggtctggaa | gcggcggctg | tacctgcgta | ggggcacacc | gtcagggccc | accaggaact | 240
| tctcaaagtt | ccaggcaacn | tcgttgcgac | acaccggaga | ccaggtgatn | agcttggggt | 300
| cggtcataan | cgcggtggcg | tcgtcgctgg | gagctggcag | ggcctcccgc | aggaaggcna | 360
| ataaaaggtg | cgccccgca | ccgttcanct | cgcacttctc | naanaccatg | angttgggct | 420
| cnaacccacc | accannccgg | acttccttga | nggaattccc | aaatctcttc | gntcttgggc | 480
| ttctnctgat | gccctanctg | gttgcccngn | atgccaanca | nccccaancc | ccggggtcct | 540
| aaancaccen | cctcctcntt | tcatctgggt | tnttntcccc | ggaccntggt | tcctctcaag | 600
| ggancccata | tctcnaccan | tactcaccnt | nccccccnt | gnnacccanc | cttctanngn | 660
| ttcccnceg | nectctggcc | cntcaaanan | gcttncacna | cctgggtctg | ccttccccec | 720
| tncectatet | gnacccenen | tttgtctcan | tnt | | | 753

<210> SEQ ID NO 41
<211> LENGTH: 341
<212> TYPE: DNA
<213> ORGANISM: Homo sapien

<400> SEQUENCE: 41

| | | | | | |
|---|---|---|---|---|---|
| actatatcca | tcacaacaga | catgcttcat | cccatagact | tcttgacata | gcttcaaatg | 60
| agtgaaccca | tccttgattt | atatacatat | atgttctcag | tattttggga | gcctttccac | 120
| ttctttaaac | cttgttcatt | atgaacactg | aaaataggaa | tttgtgaaga | gttaaaaagt | 180
| tatagcttgt | ttacgtagta | agttttgaa | gtctacattc | aatccagaca | cttagttgag | 240
| tgttaaactg | tgatttttaa | aaatatcat | ttgagaatat | tctttcagag | gtattttcat | 300
| ttttacttt | tgattaattg | tgttttatat | attagggtag | t | | 341

<210> SEQ ID NO 42
<211> LENGTH: 101
<212> TYPE: DNA
<213> ORGANISM: Homo sapien

<400> SEQUENCE: 42

| | | | | | |
|---|---|---|---|---|---|
| acttactgaa | tttagttctg | tgctcttcct | tatttagtgt | tgtatcataa | atactttgat | 60
| gtttcaaaca | ttctaaataa | ataattttca | gtggcttcat | a | | 101

<210> SEQ ID NO 43
<211> LENGTH: 305
<212> TYPE: DNA
<213> ORGANISM: Homo sapien

<400> SEQUENCE: 43

| | | | | | |
|---|---|---|---|---|---|
| acatctttgt | tacagtctaa | gatgtgttct | taaatcacca | ttccttcctg | gtcctcaccc | 60
| tccagggtgg | tctcacactg | taattagagc | tattgaggag | tctttacagc | aaattaagat | 120
| tcagatgcct | tgctaagtct | agagttctag | agttatgttt | cagaaagtct | aagaaaccca | 180

```
cctcttgaga ggtcagtaaa gaggacttaa tatttcatat ctacaaaatg accacaggat      240
tggatacaga acgagagtta tcctggataa ctcagagctg agtacctgcc cgggggccgc      300
tcgaa                                                                  305
```

<210> SEQ ID NO 44
<211> LENGTH: 852
<212> TYPE: DNA
<213> ORGANISM: Homo sapien
<220> FEATURE:
<221> NAME/KEY: misc_feature
<222> LOCATION: (1)...(852)
<223> OTHER INFORMATION: n = A,T,C or G

<400> SEQUENCE: 44

```
acataaatat cagagaaaag tagtctttga aatatttacg tccaggagtt ctttgtttct       60
gattatttgg tgtgtgtttt ggtttgtgtc caaagtattg gcagcttcag ttttcatttt      120
ctctccatcc tcgggcattc ttcccaaatt tatataccag tcttcgtcca tccacacgct      180
ccagaatttc tcttttgtag taatatctca tagctcggct gagcttttca taggtcatgc      240
tgctgttgtt cttctttta ccccatagct gagccactgc ctctgatttc aagaacctga       300
agacgccctc agatcggtct tcccatttta ttaatcctgg gttcttgtct gggttcaaga      360
ggatgtcgcg gatgaattcc cataagtgag tccctctcgg gttgtgcttt ttggtgtggc      420
acttggcagg ggggtcttgc tccttttca tatcaggtga ctctgcaaca ggaaggtgac       480
tggtggttgt catggagatc tgagcccggc agaaagtttt gctgtccaac aaatctactg      540
tgctaccata gttggtgtca tataaatagt tctngtcttt ccaggtgttc atgatggaag      600
gctcagtttg ttcagtcttg acaatgacat tgtgtgtgga ctggaacagg tcactactgc      660
actggccgtt ccacttcaga tgctgcaagt tgctgtagag gagntgcccc gccgtccctg      720
ccgcccgggt gaactcctgc aaactcatgc tgcaaaggtg ctcgccgttg atgtcgaact      780
cntggaaagg gatacaattg gcatccagct ggttggtgtc caggaggtga tggagccact      840
cccacacctg gt                                                         852
```

<210> SEQ ID NO 45
<211> LENGTH: 234
<212> TYPE: DNA
<213> ORGANISM: Homo sapien

<400> SEQUENCE: 45

```
acaacagacc cttgctcgct aacgacctca tgctcatcaa gttggacgaa tccgtgtccg       60
agtctgacac catccggagc atcagcattg cttcgcagtg ccctaccgcg gggaactctt      120
gcctcgtttc tggctggggt ctgctggcga acggcagaat gcctaccgtg ctgcagtgcg      180
tgaacgtgtc ggtggtgtct gaggaggtct gcagtaagct ctatgacccg ctgt            234
```

<210> SEQ ID NO 46
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 46

```
acttttatt taaatgttta taaggcagat ctatgagaat gatagaaaac atggtgtgta        60
```

-continued

| | |
|---|---|
| atttgatagc aatattttgg agattacaga gttttagtaa ttaccaatta cacagttaaa | 120 |
| aagaagataa tatattccaa gcanatacaa aatatctaat gaaagatcaa ggcaggaaaa | 180 |
| tgantataac taattgacaa tggaaaatca attttaatgt gaattgcaca ttatcctttta | 240 |
| aaagctttca aaanaaanaa ttattgcagt ctanttaatt caaacagtgt taaatggtat | 300 |
| caggataaan aactgaaggg canaaagaat taattttcac ttcatgtaac ncacccanat | 360 |
| ttacaatggc ttaaatgcan ggaaaaagca gtggaagtag ggaagtantc aaggtctttc | 420 |
| tggtctctaa tctgccttac tctttgggtg tggctttgat cctctggaga cagctgccag | 480 |
| ggctcctgtt atatccacaa tcccagcagc aagatgaagg gatgaaaaag gacacatgct | 540 |
| gccttccttt gaggagactt catctcactg ccaacactc agtcacatgt | 590 |

<210> SEQ ID NO 47
<211> LENGTH: 774
<212> TYPE: DNA
<213> ORGANISM: Homo sapien
<220> FEATURE:
<221> NAME/KEY: misc_feature
<222> LOCATION: (1)...(774)
<223> OTHER INFORMATION: n = A,T,C or G

<400> SEQUENCE: 47

| | |
|---|---|
| acaagggggc ataatgaagg agtgggggana gattttaaag aaggaaaaaa aacgaggccc | 60 |
| tgaacagaat tttcctgnac aacggggctt caaaataatt ttcttgggga ggttcaagac | 120 |
| gcttcactgc ttgaaactta aatggatgtg ggacanaatt ttctgtaatg accctgaggg | 180 |
| cattacagac gggactctgg gaggaaggat aaacagaaag gggacaaagg ctaatcccaa | 240 |
| aacatcaaag aaaggaaggt ggcgtcatac ctcccagcct acacagttct ccagggctct | 300 |
| cctcatccct ggaggacgac agtggaggaa caactgacca tgtccccagg ctcctgtgtg | 360 |
| ctggctcctg gtcttcagcc cccagctctg gaagcccacc ctctgctgat cctgcgtggc | 420 |
| ccacactcct tgaacacaca tccccaggtt atattcctgg acatggctga acctcctatt | 480 |
| cctacttccg agatgccttg ctccctgcag cctgtcaaaa tcccactcac cctccaaacc | 540 |
| acggcatggg aagcctttct gacttgcctg attactccag catcttggaa caatccctga | 600 |
| ttccccactc cttagaggca agatagggtg gttaagagta gggctggacc acttggagcc | 660 |
| aggctgctgg cttcaaaattn tggctcattt acgagctatg ggaccttggg caagtnatct | 720 |
| tcacttctat gggcntcatt ttgttctacc tgcaaaatgg gggataataa tagt | 774 |

<210> SEQ ID NO 48
<211> LENGTH: 124
<212> TYPE: DNA
<213> ORGANISM: Homo sapien
<220> FEATURE:
<221> NAME/KEY: misc_feature
<222> LOCATION: (1)...(124)
<223> OTHER INFORMATION: n = A,T,C or G

<400> SEQUENCE: 48

| | |
|---|---|
| canaaattga aatttttataa aaaggcattt ttctcttata tccataaaat gatataattt | 60 |
| ttgcaantat anaaatgtgt cataaattat aatgttcctt aattacagct caacgcaact | 120 |
| tggt | 124 |

<210> SEQ ID NO 49
<211> LENGTH: 147
<212> TYPE: DNA
<213> ORGANISM: Homo sapien

```
<220> FEATURE:
<221> NAME/KEY: misc_feature
<222> LOCATION: (1)...(147)
<223> OTHER INFORMATION: n = A,T,C or G

<400> SEQUENCE: 49
gccgatgcta ctattttatt gcaggaggtg ggggtgtttt tattattctc tcaacagctt      60
tgtggctaca ggtggtgtct gactgcatna aaaanttttt tacgggtgat tgcaaaaatt     120
ttagggcacc catatcccaa gcantgt                                         147

<210> SEQ ID NO 50
<211> LENGTH: 107
<212> TYPE: DNA
<213> ORGANISM: Homo sapien

<400> SEQUENCE: 50
acattaaatt aataaaagga ctgttgggt tctgctaaaa cacatggctt gatatattgc       60
atggtttgag gttaggagga gttaggcata tgttttggga gaggggt                  107

<210> SEQ ID NO 51
<211> LENGTH: 204
<212> TYPE: DNA
<213> ORGANISM: Homo sapien

<400> SEQUENCE: 51
gtcctaggaa gtctagggga cacacgactc tggggtcacg gggccgacac acttgcacgg      60
cgggaaggaa aggcagagaa gtgacaccgt caggggaaa tgacagaaag gaaaatcaag     120
gccttgcaag gtcagaaagg ggactcaggg cttccaccac agccctgccc cacttggcca    180 cctcccttt gggaccagca atgt                                            204

<210> SEQ ID NO 52
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 52
acaaagataa catttatctt ataacaaaaa tttgatagtt ttaaaggtta gtattgtgta      60
gggtattttc caaaagacta agagataac tcaggtaaaa agttagaaat gtataaaaca    120
ccatcagaca ggtttttaaa aaacaacata ttacaaaatt agacaatcat ccttaaaaaa    180
aaaacttctt gtatcaattt cttttgttca aaatgactga cttaantatt tttaaatatt    240
tcanaaacac ttcctcaaaa attttcaana tggtagcttt canatgtncc ctcagtccca    300
atgttgctca gataaataaa tctcgtgaga acttaccacc caccacaagc tttctggggc    360
atgcaacagt gtcttttctt tncttttttct ttttttttt ttacaggcac agaaactcat    420
caattttatt tggataacaa agggtctcca aattatattg aaaaataaat ccaagttaat    480
atcactcttg t                                                          491

<210> SEQ ID NO 53
<211> LENGTH: 484
<212> TYPE: DNA
<213> ORGANISM: Homo sapien
<220> FEATURE:
<221> NAME/KEY: misc_feature
<222> LOCATION: (1)...(484)
```

```
<223> OTHER INFORMATION: n = A,T,C or G

<400> SEQUENCE: 53
acataattta gcagggctaa ttaccataag atgctattta ttaanaggtn tatgatctga      60
gtattaacag ttgctgaagt ttggtatttt tatgcagcat tttcttttttg ctttgataac    120 actacagaac ccttaaggac actgaaaatt agtaagtaaa gttcagaaac attagctgct    180
caatcaaatc tctacataac actatagtaa ttaaaacgtt aaaaaaaagt gttgaaatct    240
gcactagtat anaccgctcc tgtcaggata aactgctttt ggaacagaaa gggaaaaanc    300
agctttgant ttctttgtgc tgatangagg aaaggctgaa ttaccttgtt gcctctccct    360
aatgattggc aggtcnggta aatnccaaaa catattccaa ctcaacactt cttttccncg    420
tancttgant ctgtgtattc caggancagg cggatggaat gggccagccc ncggatgttc    480 cant                                                                 484

<210> SEQ ID NO 54
<211> LENGTH: 151
<212> TYPE: DNA
<213> ORGANISM: Homo sapien

<400> SEQUENCE: 54
actaaacctc gtgcttgtga actccataca gaaaacggtg ccatccctga acacggctgg     60
ccactgggta tactgctgac aaccgcaaca acaaaaacac aaatccttgg cactggctag   120
tctatgtcct ctcaagtgcc ttttttgtttg t                                  151

<210> SEQ ID NO 55
<211> LENGTH: 91
<212> TYPE: DNA
<213> ORGANISM: Homo sapien

<400> SEQUENCE: 55
acctggcttg tctccgggtg gttcccggcg ccccccacgg tccccagaac ggacactttc     60
gccctccagt ggatactcga gccaaagtgg t                                    91

<210> SEQ ID NO 56
<211> LENGTH: 133
<212> TYPE: DNA
<213> ORGANISM: Homo sapien

<400> SEQUENCE: 56
ggcggatgtg cgttggttat atacaaatat gtcattttat gtaagggact tgagtatact     60 tggattttttg gtatctgtgg gttggggggga cggtccagga accaataccc catggatacc  120
aagggacaac tgt                                                        133

<210> SEQ ID NO 57
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 57
actctggaga acctgagccg ctgctccgcc tctgggatga ggtgatgcan gcngtggcgc      60
gactgggagc tgagcccttc cctttgcgcc tgcctcagag gattgttgcc gacntgcana   120
tctcantggg ctggatncat gcagggt                                         147
```

<210> SEQ ID NO 58
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 58

| | | |
|---|---|---|
| acagggatat aggttttnaag ttattgtnat tgtaaaatac attgaattttt ctgtatactc | 60 |
| tgattacata catttatcct ttaaaaaaga tgtaaatctt aatttttatg ccatctatta | 120 |
| atttaccaat gagttacctt gtaaatgaga agtcatgata gcactgaatt ttaactagtt | 180 |
| ttgacttcta agtttggt | 198 |

<210> SEQ ID NO 59
<211> LENGTH: 330
<212> TYPE: DNA
<213> ORGANISM: Homo sapien

<400> SEQUENCE: 59

| | |
|---|---|
| acaacaaatg ggttgtgagg aagtcttatc agcaaaactg gtgatggcta ctgaaaagat | 60 |
| ccattgaaaa ttatcattaa tgattttaaa tgacaagtta tcaaaaactc actcaatttt | 120 |
| cacctgtgct agcttgctaa aatgggagtt aactctagag caaatatagt atcttctgaa | 180 |
| tacagtcaat aaatgacaaa gccagggcct acaggtggtt tccagacttt ccagacccag | 240 |
| cagaaggaat ctattttatc acatggatct ccgtctgtgc tcaaaatacc taatgatatt | 300 |
| tttcgtcttt attggacttc tttgaagagt | 330 |

<210> SEQ ID NO 60
<211> LENGTH: 175
<212> TYPE: DNA
<213> ORGANISM: Homo sapien

<400> SEQUENCE: 60

| | |
|---|---|
| accgtgggtg ccttctacat tcctgacggc tccttcacca acatctggtt ctacttcggc | 60 |
| gtcgtgggct ccttcctctt catcctcatc cagctggtgc tgctcatcga ctttgcgcac | 120 |
| tcctggaacc agcggtggct gggcaaggcc gaggagtgcg attcccgtgc ctggt | 175 |

<210> SEQ ID NO 61
<211> LENGTH: 154
<212> TYPE: DNA
<213> ORGANISM: Homo sapien

<400> SEQUENCE: 61

| | |
|---|---|
| accccacttt tcctcctgtg agcagtctgg acttctcact gctacatgat gagggtgagt | 60 |
| ggttgttgct cttcaacagt atcctcccct ttccggatct gctgagccgg acagcagtgc | 120 |
| tggactgcac agccccgggg ctccacattg ctgt | 154 |

<210> SEQ ID NO 62
<211> LENGTH: 30
<212> TYPE: DNA
<213> ORGANISM: Homo sapien

<400> SEQUENCE: 62

| | |
|---|---|
| cgctcgagcc ctatagtgag tcgtattaga | 30 |

<210> SEQ ID NO 63
<211> LENGTH: 89
<212> TYPE: DNA
<213> ORGANISM: Homo sapien

<400> SEQUENCE: 63

| | | | | | |
|---|---|---|---|---|---|
| acaagtcatt | tcagcaccct | tgctcttca | aaactgacca | tcttttatat | ttaatgcttc | 60 |
| ctgtatgaat | aaaaatggtt | atgtcaagt | | | | 89 |

<210> SEQ ID NO 64
<211> LENGTH: 97
<212> TYPE: DNA
<213> ORGANISM: Homo sapien

<400> SEQUENCE: 64

| | | | | | |
|---|---|---|---|---|---|
| accggagtaa | ctgagtcggg | acgctgaatc | tgaatccacc | aataaataaa | ggttctgcag | 60 |
| aatcagtgca | tccaggattg | gtccttggat | ctggggt | | | 97 |

<210> SEQ ID NO 65
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 65

| | | | | | |
|---|---|---|---|---|---|
| acaacaanaa | ntccttctt | taggccactg | atggaaacct | ggaaccccct | tttgatggca | 60 |
| gcatggcgtc | ctaggccttg | acacagcggc | tggggtttgg | gctntcccaa | accgcacacc | 120 |
| ccaaccctgg | tctacccaca | nttctggcta | tgggctgtct | ctgccactga | acatcagggt | 180 |
| tcggtcataa | natgaaatcc | caangggac | agaggtcagt | agaggaagct | caatgagaaa | 240 |
| ggtgctgttt | gctcagccag | aaaacagctg | cctggcattc | gccgctgaac | tatgaacccg | 300 |
| tgggggtgaa | ctaccccca | gaggaatcat | gcctgggcga | tgcaaggtg | ccaacaggag | 360 |
| gggcgggagg | agcatgt | | | | | 37 |

<210> SEQ ID NO 66
<211> LENGTH: 305
<212> TYPE: DNA
<213> ORGANISM: Homo sapien

<400> SEQUENCE: 66

| | | | | | |
|---|---|---|---|---|---|
| acgcctttcc | ctcagaattc | agggaagaga | ctgtcgcctg | ccttcctccg | ttgttgcgtg | 60 |
| agaacccgtg | tgccccttcc | caccatatcc | accctcgctc | catctttgaa | ctcaaacacg | 120 |
| aggaactaac | tgcaccctgg | tcctctcccc | agtccccagt | tcaccctcca | tccctcacct | 180 |
| tcctccactc | taagggatat | caacactgcc | cagcacaggg | gccctgaatt | tatgtggttt | 240 |
| ttatatattt | tttaataaga | tgcactttat | gtcatttttt | aataaagtct | gaagaattac | 300 |
| tgttt | | | | | | 305 |

<210> SEQ ID NO 67
<211> LENGTH: 385
<212> TYPE: DNA
<213> ORGANISM: Homo sapien

<400> SEQUENCE: 67

| | | | | | |
|---|---|---|---|---|---|
| actacacaca | ctccacttgc | ccttgtgaga | cactttgtcc | cagcacttta | ggaatgctga | 60 |

```
ggtcggacca gccacatctc atgtgcaaga ttgcccagca gacatcaggt ctgagagttc      120
cccttttaaa aaaggggact tgcttaaaaa agaagtctag ccacgattgt gtagagcagc      180
tgtgctgtgc tggagattca cttttgagag agttctcctc tgagacctga tctttagagg      240
ctgggcagtc ttgcacatga gatggggctg gtctgatctc agcactcctt agtctgcttg      300
cctctcccag ggcccagcc tggccacacc tgcttacagg gcactctcag atgcccatac      360
catagtttct gtgctagtgg accgt                                            385

<210> SEQ ID NO 68
<211> LENGTH: 73
<212> TYPE: DNA
<213> ORGANISM: Homo sapien

<400> SEQUENCE: 68
acttaaccag atatattttt accccagatg gggatattct ttgtaaaaaa tgaaaataaa       60 gttttttaa tgg                                                          73

<210> SEQ ID NO 69
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 69
actagtccag tgtggtggaa ttccattgtg ttgggggctc tcaccctcct ctcctgcagc       60
tccagctttg tgctctgcct ctgaggagac catggcccag catctgagta ccctgctgct      120
cctgctggcc accctagctg tggccctggc ctggagcccc aaggaggagg ataggataat      180
cccgggtggc atctataacg cagacctcaa tgatgagtgg gtacagcgtg cccttcactt      240
cgccatcagc gagtataaca aggccaccaa agatgactac tacagacgtc cgctgcgggt      300
actaagagcc aggcaacaga ccgttggggg ggtgaattac ttcttcgacg tagaggtggg      360
ccgaaccata tgtaccaagt cccagcccaa cttggacacc tgtgccttcc atgaacagcc      420
agaactgcag aagaaacagt tgtgctcttt cgagatctac gaagttccct ggggagaaca      480
gaangtccct gggtgaaatc caggtgtcaa gaaatcctan ggatctgttg ccaggc          536

<210> SEQ ID NO 70
<211> LENGTH: 477
<212> TYPE: DNA
<213> ORGANISM: Homo sapien

<400> SEQUENCE: 70 atgacccta cagggggccc tctcagccct cctaatgacc tccggcctag ccatgtgatt       60
tcacttccac tccataacgc tcctcatact aggcctacta accaacacac taaccatata      120
ccaatgatgg cgcgatgtaa cacgagaaag cacataccaa ggccaccaca caccacctgt      180
ccaaaaaggc cttcgatacg ggataatcct atttattacc tcagaagttt ttttcttcgc      240 agggatttt ctgagccttt taccactcca gcctagcccc tacccccaa ctaggagggc      300 actggccccc aacaggcatc acccgctaa atcccctaga agtcccactc ctaaacacat      360
ccgtattact cgcatcagga gtatcaatca cctgagctca ccatagtcta atagaaaaca      420
accgaaacca aattattcaa agcactgctt attacaattt tactgggtct ctattttt        477
```

<210> SEQ ID NO 71
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 71

| | | | | | |
|---|---|---|---|---|---|
| agagctatag | gtacagtgtg | atctcagctt | tgcaaacaca | ttttctacat | agatagtact | 60 |
| aggtattaat | agatatgtaa | agaaagaaat | cacaccatta | ataatggtaa | gattggttta | 120 |
| tgtgatttta | gtggtatttt | tggcacccct | atatatgttt | tccaaacttt | cagcagtgat | 180 |
| attatttcca | taacttaaaa | agtgagtttg | aaaagaaaa | tctccagcaa | gcatctcatt | 240 |
| taaataaagg | tttgtcatct | ttaaaaatac | agcaatatgt | gactttttaa | aaaagctgtc | 300 |
| aaataggtgt | gaccctacta | ataattatta | gaaatacatt | taaaaacatc | gagtacctca | 360 |
| agtcagtttg | ccttgaaaaa | tatcaaatat | aactcttaga | gaaatgtaca | taaaagaatg | 420 |
| cttcgtaatt | ttggagtang | aggttccctc | ctcaattttg | tatttttaaa | aagtacatgg | 480 |
| taaaaaaaaa | aattcacaac | agtatataag | gctgtaaaat | gaagaattct | gcc | 533 |

<210> SEQ ID NO 72
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G

<400> SEQUENCE: 72

| | | | | | |
|---|---|---|---|---|---|
| tattacggaa | aaacacacca | cataattcaa | ctancaaaga | anactgcttc | agggcgtgta | 60 |
| aaatgaaagg | cttccaggca | gttatctgat | taaagaacac | taaaagaggg | acaaggctaa | 120 |
| aagccgcagg | atgtctacac | tatancaggc | gctatttggg | ttggctggag | gagctgtgga | 180 |
| aaacatggan | agattggtgc | tgganatcgc | cgtggctatt | cctcattgtt | attacanagt | 240 |
| gaggttctct | gtgtgcccac | tggtttgaaa | accgttctnc | aataatgata | gaatagtaca | 300 |
| cacatgagaa | ctgaaatggc | ccaaacccag | aaagaaagcc | caactagatc | ctcagaanac | 360 |
| gcttctaggg | acaataaccg | atgaagaaaa | gatggcctcc | ttgtgccccc | gtctgttatg | 420 |
| atttctctcc | attgcagcna | naaacccgtt | cttctaagca | aacncaggtg | atgatggcna | 480 |
| aaatacaccc | cctcttgaag | naccnggagg | a | | | 511 |

<210> SEQ ID NO 73
<211> LENGTH: 499
<212> TYPE: DNA
<213> ORGANISM: Homo sapien
<220> FEATURE:
<221> NAME/KEY: misc_feature
<222> LOCATION: (1)...(499)
<223> OTHER INFORMATION: n = A,T,C or G

<400> SEQUENCE: 73

| | | | | | |
|---|---|---|---|---|---|
| cagtgccagc | actggtgcca | gtaccagtac | caataacagt | gccagtgcca | gtgccagcac | 60 |
| cagtggtggc | ttcagtgctg | gtgccagcct | gaccgccact | ctcacatttg | ggctcttcgc | 120 |
| tggccttggt | ggagctggtg | ccagcaccag | tggcagctct | ggtgcctgtg | gtttctccta | 180 |
| caagtgagat | tttagatatt | gttaatcctg | ccagtctttc | tcttcaagcc | agggtgcatc | 240 |

```
ctcagaaacc tactcaacac agcactctag gcagccacta tcaatcaatt gaagttgaca      300
ctctgcatta aatctatttg ccatttctga aaaaaaaaa aaaaaaaggg cggccgctcg      360
antctagagg gcccgtttaa acccgctgat cagcctcgac tgtgccttct anttgccagc      420
catctgttgt ttgcccctcc cccgntgcct tccttgaccc tggaaagtgc cactcccact      480
gtcctttcct aantaaaat                                                   499
```

<210> SEQ ID NO 74
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 74

```
tttcatagga gaacacactg aggagatact tgaagaattt ggattcagcc gcgaagagat       60
ttatcagctt aactcagata aaatcattga agtaataag gtaaaagcta gtctctaact       120
tccaggccca cggctcaagt gaatttgaat actgcattta cagtgtagag taacacataa      180
cattgtatgc atgaaaacat ggaggaacag tattacagtg tcctaccact ctaatcaaga      240
aaagaattac agactctgat ctacagtga tgattgaatt ctaaaaatgg taatcattag       300
ggcttttgat ttataanact ttgggtactt atactaaatt atggtagtta tactgccttc      360
cagtttgctt gatatatttg ttgatattaa gattcttgac ttatattttg aatgggttct      420
actgaaaaan gaatgatata ttcttgaaga catcgatata catttattta cactcttgat      480
tctacaatgt agaaaatgaa ggaaatgccc caaattgtat ggtgataaaa gtcccgt        537
```

<210> SEQ ID NO 75
<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 75

```
caaanacaat tgttcaaaag atgcaaatga tacactactg ctgcagctca caaacacctc       60
tgcatattac acgtacctcc tcctgctcct caagtagtgt ggtctatttt gccatcatca      120
cctgctgtct gcttagaaga acggctttct gctgcaangg agagaaatca taacagacgg      180
tggcacaagg aggccatctt ttcctcatcg gttattgtcc ctagaagcgt cttctgagga      240
tctagttggg ctttctttct gggtttgggc catttcantt ctcatgtgtg tactattcta      300
tcattattgt ataacggttt tcaaaccngt gggcacncag agaacctcac tctgtaataa      360
caatgaggaa tagccacggt gatctccagc accaaatctc tccatgtttnt tccagagctc      420 ctccagccaa cccaaatagc cgctgctatn gtgtagaaca tccctgn                    467
```

<210> SEQ ID NO 76
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 76

```
aagctgacag cattcgggcc gagatgtctc gctccgtggc cttagctgtg ctcgcgctac    60
tctctctttc tggcctggag gctatccagc gtactccaaa gattcaggtt tactcacgtc   120
atccagcaga gaatggaaag tcaaatttcc tgaattgcta tgtgtctggg tttcatccat   180
ccgacattga agttgactta ctgaagaatg gagagagaat tgaaaaagtg gagcattcag   240
acttgtcttt cagcaaggac tggtctttct atctcttgta ctacactgaa ttcaccccca   300
ctgaaaaaga tgagtatgcc tgccgtgtga accatgtgac tttgtcacag cccaagatng   360
ttnagtggga tcganacatg taagcagcan catgggaggt                         400
```

<210> SEQ ID NO 77
<211> LENGTH: 248
<212> TYPE: DNA
<213> ORGANISM: Homo sapien

<400> SEQUENCE: 77

```
ctggagtgcc ttggtgtttc aagcccctgc aggaagcaga atgcaccttc tgaggcacct    60
ccagctgccc cggcggggga tgcgaggctc ggagcaccct tgcccggctg tgattgctgc   120
caggcactgt tcatctcagc ttttctgtcc ctttgctccc ggcaagcgct tctgctgaaa   180
gttcatatct ggagcctgat gtcttaacga ataaaggtcc catgctccac ccgaaaaaaa   240
aaaaaaaa                                                           248
```

<210> SEQ ID NO 78
<211> LENGTH: 201
<212> TYPE: DNA
<213> ORGANISM: Homo sapien

<400> SEQUENCE: 78

```
actagtccag tgtggtggaa ttccattgtg ttgggcccaa cacaatggct acctttaaca    60
tcacccagac cccgccctgc ccgtgcccca cgctgctgct aacgacagta tgatgcttac   120
tctgctactc ggaaactatt tttatgtaat taatgtatgc tttcttgttt ataaatgcct   180
gatttaaaaa aaaaaaaaaa a                                             201
```

<210> SEQ ID NO 79
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 79

```
tcctttttgtt aggttttttga dacaaccccta gacctaaact gtgtcacaga cttctgaatg    60
tttaggcagt gctagtaatt cctcgtaat gattctgtta ttactttcct attctttatt   120
cctctttctt ctgaagatta tgaagttgaa aattgaggt ggataaatac aaaaaggtag   180
tgtgatagta taagtatcta agtgcagatg aaagtgtgtt atatatatcc attcaaaatt   240
atgcaagtta gtaattactc agggttaact aaattacttt aatatgctgt tgaacctact   300
ctgttccttg gctagaaaaa attataaaca ggactttgtt agtttgggaa gccaaattga   360
taatattcta tgttctaaaa gttgggctat acataaanta tnaagaaata tggaattta   420
ttcccaggaa tatggggttc atttatgaat antacccggg anagaagttt tgantnaaac   480
cngttttggt taatacgtta atatgtcctn aatnacaag gcntgactta tttccaaaaa   540
```

```
aaaaaaaaaa aa                                                              552

<210> SEQ ID NO 80
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 80
acagggattt gagatgctaa ggccccagag atcgtttgat ccaaccctct tattttcaga     60
ggggaaaatg gggcctagaa gttacagagc atctagctgg tgcgctggca ccctggcct    120 cacacagact cccgagtagc tgggactaca ggcacacagt cactgaagca ggccctgttt    180
gcaattcacg ttgccacctc caacttaaac attcttcata tgtgatgtcc ttagtcacta    240
aggttaaact ttcccaccca gaaaaggcaa cttagataaa atcttagagt actttcatac    300
tcttctaagt cctcttccag cctcactttg agtcctcctt ggggttgat aggaantntc     360 tcttggcttt ctcaataaaa tctctatcca tctcatgttt aatttggtac gcntaaaaat    420
gctgaaaaaa ttaaaatgtt ctggtttcnc tttaaaaaaa aaaaaaaaaa aaaaaa        476

<210> SEQ ID NO 81
<211> LENGTH: 232
<212> TYPE: DNA
<213> ORGANISM: Homo sapien
<220> FEATURE:
<221> NAME/KEY: misc_feature
<222> LOCATION: (1)...(232)
<223> OTHER INFORMATION: n = A,T,C or G

<400> SEQUENCE: 81 ttttttttg tatgccntcn ctgtggngtt attgttgctg ccaccctgga ggagcccagt       60
ttcttctgta tctttctttt ctgggggatc ttcctggctc tgcccctcca ttcccagcct    120
ctcatcccca tcttgcactt ttgctagggt tggaggcgct ttcctggtag cccctcagag    180
actcagtcag cgggaataag tcctagggggt gggggtgtg gcaagccggc ct            232

<210> SEQ ID NO 82
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 82
aggcgggagc agaagctaaa gccaaagccc aagaagagtg gcagtgccag cactggtgcc     60
agtaccagta ccaataacat gccagtgcca gtgccagcac cagtggtggc ttcagtgctg    120
gtgccagcct gaccgccact ctcacatttg ggctcttcgc tggccttggt ggagctggtg    180
ccagcaccag tggcagctct ggtgcctgtg gtttctccta caagtgagat tttagatatt    240
gttaatcctg ccagtctttc tcttcaagcc agggtgcatc ctcagaaacc tactcaacac    300
agcactctng gcagccacta tcaatcaatt gaagttgaca ctctgcatta aatctatttg    360
ccatttcaaa aaaaaaaaaa aaa                                             383

<210> SEQ ID NO 83
```

-continued

```
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 83
accgaattgg gaccgctggc ttataagcga tcatgtcctc cagtattacc tcaacgagca        60
gggagatcga gtctatacgc tgaagaaatt tgacccgatg ggacaacaga cctgctcagc       120
ccatcctgct cggttctccc cagatgacaa atactctcga caccgaatca ccatcaagaa       180
acgcttcaag gtgctcatga cccagcaacc gcgccctgtc ctctgagggt ccttaaactg       240
atgtcttttc tgccacctgt tacccctcgg agactccgta accaaactct tcggactgtg       300
agccctgatg cctttttgcc agccatactc tttggcntcc agtctctcgt ggcgattgat       360
tatgcttgtg tgaggcaatc atggtggcat cacccatnaa gggaacacat ttganttttt       420
tttcncatat tttaaattac naccagaata nttcagaata aatgaattga aaaactctta       480
aaaaaaaaaa aaaa                                                         494

<210> SEQ ID NO 84
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 84
gctggtagcc tatggcgtgg ccacggangg gctcctgagg cacgggacag tgacttccca        60
agtatcctgc gccgcgtctt ctaccgtccc tacctgcaga tcttcgggca gattccccag       120
gaggacatgg acgtggccct catggagcac agcaactgct cgtcggagcc cggcttctgg       180
gcacaccctc ctggggccca ggcgggcacc tgcgtctccc agtatgccaa ctggctggtg       240
gtgctgctcc tcgtcatctt cctgctcgtg gccaacatcc tgctggtcac ttgctcattg       300
ccatgttcag ttacacattc ggcaaagtac agggcaacag cnatctctac tgggaaggcc       360
agcgttnccg cctcatccgg                                                   380

<210> SEQ ID NO 85
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 85
gagttagctc ctccacaacc ttgatgaggt cgtctgcagt ggcctctcgc ttcataccgc        60
tnccatcgtc atactgtagg tttgccacca cctcctgcat cttggggcgg ctaatatcca       120
ggaaactctc aatcaagtca ccgtcnatna acctgtggc tggttctgtc ttccgctcgg        180
tgtgaaagga tctccagaag gagtgctcga tcttccccac acttttgatg actttattga       240
gtcgattctg catgtccagc aggaggttgt accagtctct tgacagtgag gtcaccagcc       300
ctatcatgcc nttgaacgtg ccgaagaaca ccgagccttg tgtgggggt gnagtctcac        360
ccagattctg cattaccaga nagccgtggc aaaaganatt gacaactcgc ccaggnngaa       420
```

```
aaagaacacc tcctggaagt gctngccgct cctcgtccnt tggtggnngc gcntnccttt      480
t                                                                      481
```

<210> SEQ ID NO 86
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 86

```
aacatcttcc tgtataatgc tgtgtaatat cgatccgatn ttgtctgctg agaattcatt       60
acttggaaaa gcaacttnaa gcctggacac tggtattaaa attcacaata tgcaacactt      120
taaacagtgt gtcaatctgc tcccttactt tgtcatcacc agtctgggaa taagggtatg      180
ccctattcac acctgttaaa agggcgctaa gcatttttga ttcaacatct ttttttttga      240
cacaagtccg aaaaaagcaa aagtaaacag ttnttaattt gttagccaat tcactttctt      300
catgggacag agccatttga tttaaaaagc aaattgcata atattgagct ttgggagctg      360
atatntgagc ggaagantag cctttctact tcaccagaca caactccttt catattggga      420
tgttnacnaa agttatgtct cttacagatg ggatgctttt gtggcaattc tg              472
```

<210> SEQ ID NO 87
<211> LENGTH: 413
<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G

<400> SEQUENCE: 87

```
agaaaccagt atctctnaaa acaacctctc ataccttgtg gacctaattt tgtgtgcgtg       60
tgtgtgtgcg cgcatattat atagacaggc acatctttt tactttgta aaagcttatg       120
cctctttggt atctatatct gtgaaagttt taatgatctg ccataatgtc ttggggacct      180
ttgtcttctg tgtaaatggt actagagaaa acacctatnt tatgagtcaa tctagttngt      240
tttattcgac atgaaggaaa tttccagatn acaacactna caaactctcc cttgactagg      300
ggggacaaag aaaagcanaa ctgaacatna gaaacaattn cctggtgaga aattncataa      360
acagaaattg ggtngtatat tgaaananng catcattnaa acgtttttt ttt             413
```

<210> SEQ ID NO 88
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

<400> SEQUENCE: 88

```
cgcagcgggt cctctctatc tagctccagc ctctcgcctg ccccactccc cgcgtcccgc       60
gtcctagccn accatggccg ggcccctgcg cgcccgctg ctcctgctgg ccatcctggc      120
cgtggccctg gccgtgagcc ccgcggccgg ctccagtccc ggcaagccgc cgcgcctggt      180
gggaggccca tggaccccgc gtggaagaag aaggtgtgcg gcgtgcactg gactttgccg      240
```

```
tcggcnanta caacaaaccc gcaacnactt ttaccnagcn cgcgctgcag gttgtgccgc    300
cccaancaaa ttgttactng gggtaantaa ttcttggaag ttgaacctgg gccaaacnng    360
tttaccagaa ccnagccaat tngaacaatt nccctccat aacagcccct tttaaaaagg    420
gaancantcc tgntctttc caaatttt                                        448
```

<210> SEQ ID NO 89
<211> LENGTH: 463
<212> TYPE: DNA
<213> ORGANISM: Homo sapien
<220> FEATURE:
<221> NAME/KEY: misc_feature
<222> LOCATION: (1)...(463)
<223> OTHER INFORMATION: n = A,T,C or G

<400> SEQUENCE: 89

```
gaattttgtg cactggccac tgtgatggaa ccattgggcc aggatgcttt gagtttatca    60
gtagtgattc tgccaaagtt ggtgttgtaa catgagtatg taaaatgtca aaaaattagc    120
agaggtctag gtctgcatat cagcagacag tttgtccgtg tattttgtag ccttgaagtt    180
ctcagtgaca agttnnttct gatgcgaagt tctnattcca gtgttttagt cctttgcatc    240
tttnatgttn agacttgcct ctntnaaatt gcttttgtnt tctgcaggta ctatctgtgg    300
tttaacaaaa tagaannact tctctgcttn gaanatttga atatcttaca tctnaaaatn    360
aattctctcc ccatannaaa acccangccc ttgggnaat ttgaaaaang gntccttcnn    420
aattcnnana anttcagntn tcatacaaca naacngganc ccc                     463
```

<210> SEQ ID NO 90
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 90

```
agggattgaa ggtctnttnt actgtcggac tgttcancca ccaactctac aagttgctgt    60
cttccactca ctgtctgtaa gcntnttaac ccagactgta tcttcataaa tagaacaaat    120
tcttcaccag tcacatcttc taggacctttt ttggattcag ttagtataag ctcttccact    180
tcctttgtta agacttcatc tggtaaagtc ttaagttttg tagaaaggaa tttaattgct    240
cgttctctaa caatgtcctc tccttgaagt atttggctga acaacccacc tnaagtccct    300
ttgtgcatcc atttttaaata tacttaatag ggcattggtn cactaggtta aattctgcaa    360
gagtcatctg tctgcaaaag ttgcgttagt atatctgcca                         400
```

<210> SEQ ID NO 91
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 91

```
gagctcggat ccaataatct ttgtctgagg gcagcacaca tatncagtgc catggnaact    60
ggtctacccc acatgggagc agcatgccgt agntatataa ggtcattccc tgagtcagac    120
atgcctcttt gactaccgtg tgccagtgct ggtgattctc acacacctcc nnccgctctt    180
```

```
tgtggaaaaa ctggcacttg nctggaacta gcaagacatc acttacaaat tcacccacga      240
gacacttgaa aggtgtaaca aagcgactct tgcattgctt tttgtccctc cggcaccagt      300
tgtcaatact aacccgctgg tttgcctcca tcacatttgt gatctgtagc tctggataca      360
tctcctgaca gtactgaaga acttcttctt ttgtttcaaa agcaactctt ggtgcctgtt      420
ngatcaggtt cccatttccc agtccgaatg ttcacatggc atatnttact tcccacaaaa      480
```

<210> SEQ ID NO 92
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 92

```
atacagccca natcccacca cgaagatgcg cttgttgact gagaacctga tgcggtcact       60
ggtcccgctg tagccccagc gactctccac ctgctgaag cggttgatgc tgcactcctt      120
cccacgcagg cagcagcggg gccggtcaat gaactccact cgtggcttgg ggttgacggt      180
taantgcagg aagaggctga ccacctcgcg gtccaccagg atgcccgact gtgcgggacc      240
tgcagcgaaa ctcctcgatg gtcatgagcg ggaagcgaat gangcccagg gccttgccca      300
gaaccttccg cctgttctct ggcgtcacct gcagctgctg ccgctacac tcggcctcgg      360 accagcggac aaacggcgtt gaacagccgc acctcacgga tgcccantgt gtcgcgctcc      420
aggaacggcn ccagcgtgtc caggtcaatg tcggtgaanc ctccgcgggt aatggcg       477
```

<210> SEQ ID NO 93
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 93

```
gaacggctgg accttgcctc gcattgtgct gctggcagga ataccttggc aagcagctcc       60
agtccgagca gccccagacc gctgccgccc gaagctaagc ctgcctctgg ccttcccctc      120
cgcctcaatg cagaaccant agtgggagca ctgtgtttag agttaagagt gaacactgtn      180
tgattttact tgggaatttc ctctgttata tagcttttcc caatgctaat ttccaaacaa      240
caacaacaaa ataacatgtt tgcctgttna gttgtataaa agtangtgat tctgtatnta      300
aagaaaatat tactgttaca tatactgctt gcaanttctg tatttattgg tnctctggaa      360
ataaatatat tattaaa                                                     377
```

<210> SEQ ID NO 94
<211> LENGTH: 495
<212> TYPE: DNA
<213> ORGANISM: Homo sapien
<220> FEATURE:
<221> NAME/KEY: misc_feature
<222> LOCATION: (1)...(495)
<223> OTHER INFORMATION: n = A,T,C or G

<400> SEQUENCE: 94

```
ccctttgagg ggttagggtc cagttcccag tggaagaaac aggccaggag aantgcgtgc       60
```

| | |
|---|---|
| cgagctgang cagatttccc acagtgaccc cagagccctg ggctatagtc tctgaccct | 120 |
| ccaaggaaag accaccttct ggggacatgg gctggagggc aggacctaga ggcaccaagg | 180 |
| gaaggcccca ttccggggct gttccccgag gaggaaggga aggggctctg tgtgcccccc | 240 |
| acgaggaana ggccctgant cctgggatca nacaccct cacgtgtatc cccacacaaa | 300 |
| tgcaagctca ccaaggtccc ctctcagtcc cttccctaca ccctgaacgg ncactggccc | 360 |
| acacccaccc agancancca cccgccatgg ggaatgtnct caaggaatcg cngggcaacg | 420 |
| tggactctng tcccnnaagg gggcagaatc tccaatagan ggannngaacc cttgctnana | 480 |
| aaaaaaaana aaaaa | 495 |

<210> SEQ ID NO 95
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 95

| | |
|---|---|
| ggttacttgg tttcattgcc accacttagt ggatgtcatt tagaaccatt ttgtctgctc | 60 |
| cctctggaag ccttgcgcag agcggacttt gtaattgttg gagaataact gctgaatttt | 120 |
| tagctgtttt gagttgattc gcaccactgc accacaactc aatatgaaaa ctatttnact | 180 |
| tatttattat cttgtgaaaa gtatacaatg aaaattttgt tcatactgta tttatcaagt | 240 |
| atgatgaaaa gcaatagata tatattcttt tattatgttn aattatgatt gccattatta | 300 |
| atcggcaaaa tgtggagtgt atgttctttt cacagtaata tatgcctttt gtaacttcac | 360 |
| ttggttattt tattgtaaat gaattacaaa attcttaatt taagaaaatg gtangttata | 420 |
| tttanttcan taatttcttt ccttgtttac gttaattttg aaaagaatgc at | 472 |

<210> SEQ ID NO 96
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 96

| | |
|---|---|
| ctgaagcatt tcttcaaact tntctacttt tgtcattgat acctgtagta agttgacaat | 60 |
| gtggtgaaat ttcaaaatta tatgtaactt ctactagttt tactttctcc cccaagtctt | 120 |
| ttttaactca tgatttttac acacacaatc cagaacttat tatatagcct ctaagtcttt | 180 |
| attcttcaca gtagatgatg aaagagtcct ccagtgtctt gngcanaatg ttctagntat | 240 |
| agctggatac atacngtggg agttctataa actcatacct cagtgggact naaccaaaat | 300 |
| tgtgttagtc tcaattccta ccacactgag ggagcctccc aaatcactat attcttatct | 360 |
| gcaggtactc ctccagaaaa acngacaggg caggcttgca tgaaaaagtn acatctgcgt | 420 |
| tacaaagtct atcttcctca nangtctgtn aaggaacaat ttaatcttct agcttt | 476 |

<210> SEQ ID NO 97
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 97

| | | | | | |
|---|---|---|---|---|---|
| actctttcta | atgctgatat | gatcttgagt | ataagaatgc | atatgtcact | agaatggata | 60 |
| aaataatgct | gcaaacttaa | tgttcttatg | caaaatggaa | cgctaatgaa | acacagctta | 120 |
| caatcgcaaa | tcaaaactca | caagtgctca | tctgttgtag | atttagtgta | ataagactta | 180 |
| gattgtgctc | cttcggatat | gattgtttct | canatcttgg | gcaatnttcc | ttagtcaaat | 240 |
| caggctacta | gaattctgtt | attggatatn | tgagagcatg | aaattttaa | naatacactt | 300 |
| gtgattatna | aattaatcac | aaatttcact | tatacctgct | atcagcagct | agaaaaacat | 360 |
| ntnnttttta | natcaaagta | ttttgtgttt | ggaantgtnn | aaatgaaatc | tgaatgtggg | 420 |
| ttcnatctta | ttttttcccn | gacnactant | tncttttta | gggnctattc | tganccatc | 479 |

<210> SEQ ID NO 98
<211> LENGTH: 461
<212> TYPE: DNA
<213> ORGANISM: Homo sapien

<400> SEQUENCE: 98

| | | | | | |
|---|---|---|---|---|---|
| agtgacttgt | cctccaacaa | aacccttga | tcaagtttgt | ggcactgaca | atcagaccta | 60 |
| tgctagttcc | tgtcatctat | tcgctactaa | atgcagactg | gaggggacca | aaaaggggca | 120 |
| tcaactccag | ctggattatt | ttggagcctg | caaatctatt | cctacttgta | cggactttga | 180 |
| agtgattcag | tttcctctac | ggatgagaga | ctggctcaag | aatatcctca | tgcagcttta | 240 |
| tgaagccact | ctgaacacgc | tggttatcta | gatgagaaca | gagaaataaa | gtcagaaaat | 300 |
| ttacctggag | aaaagaggct | ttggctgggg | accatcccat | tgaaccttct | cttaaggact | 360 |
| ttaagaaaaa | ctaccacatg | ttgtgtatcc | tggtgccggc | cgtttatgaa | ctgaccaccc | 420 |
| tttggaataa | tcttgacgct | cctgaacttg | ctcctctgcg | a | | 461 |

<210> SEQ ID NO 99
<211> LENGTH: 171
<212> TYPE: DNA
<213> ORGANISM: Homo sapien

<400> SEQUENCE: 99

| | | | | | |
|---|---|---|---|---|---|
| gtggccgcgc | gcaggtgttt | cctcgtaccg | cagggccccc | tcccttcccc | aggcgtccct | 60 |
| cggcgcctct | gcgggcccga | ggaggagcgg | ctggcgggtg | ggggagtgt | gacccaccct | 120 |
| cggtgagaaa | agccttctct | agcgatctga | gaggcgtgcc | ttggggggtac | c | 171 |

<210> SEQ ID NO 100
<211> LENGTH: 269
<212> TYPE: DNA
<213> ORGANISM: Homo sapien

<400> SEQUENCE: 100

| | | | | | |
|---|---|---|---|---|---|
| cggccgcaag | tgcaactcca | gctggggccg | tgcggacgaa | gattctgcca | gcagttggtc | 60 |
| cgactgcgac | gacggcggcg | gcgacagtcg | caggtgcagc | gcgggcgcct | gggtcttgc | 120 |
| aaggctgagc | tgacgccgca | gaggtcgtgt | cacgtcccac | gaccttgacg | ccgtcgggga | 180 |
| cagccggaac | agagcccggt | gaagcgggag | gcctcgggga | gccctcggg | aagggcggcc | 240 |
| cgagagatac | gcaggtgcag | gtggccgcc | | | | 269 |

<210> SEQ ID NO 101

```
<211> LENGTH: 405
<212> TYPE: DNA
<213> ORGANISM: Homo sapien

<400> SEQUENCE: 101 ttttttttttt ttttggaatc tactgcgagc acagcaggtc agcaacaagt ttattttgca     60
gctagcaagg taacagggta gggcatggtt acatgttcag gtcaacttcc tttgtcgtgg    120
ttgattggtt tgtctttatg ggggcggggt ggggtagggg aaacgaagca ataacatgg     180 agtgggtgca ccctccctgt agaacctggt tacaaagctt ggggcagttc acctggtctg    240
tgaccgtcat tttcttgaca tcaatgttat tagaagtcag gatatctttt agagagtcca   300
ctgttctgga gggagattag ggtttcttgc caaatccaac aaaatccact gaaaagttg     360 gatgatcagt acgaataccg aggcatattc tcatatcggt ggcca                    405

<210> SEQ ID NO 102
<211> LENGTH: 470
<212> TYPE: DNA
<213> ORGANISM: Homo sapien

<400> SEQUENCE: 102
tttttttttt tttttttttt tttttttttt tttttttttt tttttttttt tttttttttt    60
ggcacttaat ccattttat ttcaaaatgt ctacaaattt aatcccatta tacggtattt     120
tcaaaatcta aattattcaa attagccaaa tccttaccaa ataataccca aaaatcaaaa    180 atacttct ttcagcaaac ttgttacata aattaaaaaa atatatacgg ctggtgtttt      240
caaagtacaa ttatcttaac actgcaaaca ttttaaggaa ctaaaataaa aaaaaacact   300 ccgcaaagt taagggaac aacaaattct tttacaacac cattataaaa atcatatctc     360
aaatcttagg ggaatatata cttcacacgg gatcttaact tttactcact tgtttatt    420 ttttaaacca ttgtttgggc ccaacacaat ggaatccccc ctggactagt              470

<210> SEQ ID NO 103
<211> LENGTH: 581
<212> TYPE: DNA
<213> ORGANISM: Homo sapien

<400> SEQUENCE: 103
tttttttttt tttttttga ccccctctt ataaaaaaca agttaccatt ttattttact      60
tacacatatt tattttataa ttggtattag atattcaaaa ggcagctttt aaaatcaaac   120
taaatggaaa ctgccttaga tacataattc ttaggaatta gcttaaaatc tgcctaaagt    180
gaaaatcttc tctagctctt ttgactgtaa attttgact cttgtaaaac atccaaattc     240
atttttcttg tctttaaaat tatctaatct ttccattttt tccctattcc aagtcaattt    300
gcttctctag cctcatttcc tagctcttat ctactattag taagtggctt ttttcctaaa    360
agggaaaaca ggaagagaaa tggcacacaa aacaaacatt ttatattcat atttctacct    420
acgttaataa aatagcattt tgtgaagcca gctcaaaaga aggcttagat ccttttatgt    480
ccattttagt cactaaacga tatcaaagtg ccagaatgca aaaggtttgt gaacatttat    540
tcaaaagcta atataagata tttcacatac tcatctttct g                        581

<210> SEQ ID NO 104
<211> LENGTH: 578
<212> TYPE: DNA
<213> ORGANISM: Homo sapien

<400> SEQUENCE: 104
```

```
tttttttttt tttttttttt ttttctctt cttttttttt gaaatgagga tcgagttttt        60
cactctctag ataggcatg aagaaaactc atctttccag ctttaaaata acaatcaaat        120
ctcttatgct atatcatatt ttaagttaaa ctaatgagtc actggcttat cttctcctga      180
aggaaatctg ttcattcttc tcattcatat agttatatca agtactacct tgcatattga      240 gaggttttc ttctctattt acacatatat ttccatgtga atttgtatca aacctttatt      300
ttcatgcaaa ctagaaaata atgtttcttt tgcataagag aagagaacaa tatagcatta      360
caaaactgct caaattgttt gttaagttat ccattataat tagttggcag gagctaatac      420
aaatcacatt tacgacagca ataataaaac tgaagtacca gttaaatatc caaataatt        480 aaaggaacat tttagcctg ggtataatta gctaattcac tttacaagca tttattagaa      540
tgaattcaca tgttattatt cctagcccaa cacaatgg                              578
```

<210> SEQ ID NO 105
<211> LENGTH: 538
<212> TYPE: DNA
<213> ORGANISM: Homo sapien

<400> SEQUENCE: 105

```
tttttttttt ttttcagta ataatcagaa caatatttat ttttatattt aaaattcata      60
gaaaagtgcc ttacatttaa taaaagtttg tttctcaaag tgatcagagg aattagatat      120
gtcttgaaca ccaatattaa tttgaggaaa atacaccaaa atacattaag taaattattt      180
aagatcatag agcttgtaag tgaaaagata aaatttgacc tcagaaactc tgagcattaa      240
aaatccacta ttagcaaata aattactatg gacttcttgc tttaattttg tgatgaatat      300
ggggtgtcac tggtaaacca acacattctg aaggatacat tacttagtga tagattctta      360
tgtactttgc taatacgtgg atatgagttg acaagtttct cttcttcaa tcttttaagg      420 ggcgagaaat gaggaagaaa agaaaaggat tacgcatact gttctttcta tggaaggatt      480
agatatgttt cctttgccaa tattaaaaaa ataataatgt ttactactag tgaaaccc        538
```

<210> SEQ ID NO 106
<211> LENGTH: 473
<212> TYPE: DNA
<213> ORGANISM: Homo sapien

<400> SEQUENCE: 106

```
tttttttttt ttttttagtc aagtttctat ttttattata attaaagtct tggtcatttc      60
atttattagc tctgcaactt acatatttaa attaaagaaa cgttttagac aactgtacaa      120
tttataaatg taaggtgcca ttattgagta atatattcct ccaagagtgg atgtgtccct      180
tctcccacca actaatgaac agcaacatta gtttaatttt attagtagat atacactgct      240
gcaaacgcta attctcttct ccatccccat gtgatattgt gtatatgtgt gagttggtag      300
aatgcatcac aatctacaat caacagcaag atgaagctag gctgggcttt cggtgaaaat      360
agactgtgtc tgtctgaatc aaatgatctg acctatcctc ggtggcaaga actcttcgaa      420
ccgcttcctc aaaggcgctg ccacatttgt ggctctttgc acttgtttca aaa            473
```

<210> SEQ ID NO 107
<211> LENGTH: 1621
<212> TYPE: DNA
<213> ORGANISM: Homo sapien

<400> SEQUENCE: 107

-continued

```
cgccatggca ctgcagggca tctcggtcat ggagctgtcc ggcctggccc cgggcccgtt      60
ctgtgctatg gtcctggctg acttcggggc gcgtgtggta cgcgtggacc ggcccggctc     120
ccgctacgac gtgagccgct tgggccgggg caagcgctcg ctagtgctgg acctgaagca     180
gccgcgggga gccgccgtgc tgcggcgtct gtgcaagcgg tcggatgtgc tgctggagcc     240
cttccgccgc ggtgtcatgg agaaactcca gctgggccca gagattctgc agcgggaaaa     300
tccaaggctt atttatgcca ggctgagtgg atttggccag tcaggaagct tctgccggtt     360
agctggccac gatatcaact atttggcttt gtcaggtgtt ctctcaaaaa ttggcagaag     420
tggtgagaat ccgtatgccc cgctgaatct cctggctgac tttgctggtg gtggccttat     480
gtgtgcactg ggcattataa tggctctttt tgaccgcaca cgcactgaca agggtcaggt     540
cattgatgca aatatggtgg aaggaacagc atatttaagt tcttttctgt ggaaaactca     600
gaaatcgagt ctgtgggaag cacctcgagg acagaacatg ttggatggtg gagcaccttt     660
ctatacgact tacaggacag cagatgggga attcatggct gttggagcaa tagaacccca     720
gttctacgag ctgctgatca aaggacttgg actaaagtct gatgaacttc ccaatcagat     780
gagcatggat gattggccag aaatgaagaa gaagtttgca gatgtatttg caagaagac      840 gaaggcagag tggtgtcaaa tcttttgacgg cacagatgcc tgtgtgactc cggttctgac     900
ttttgaggag gttgttcatc atgatcacaa caaggaacgg ggctcgttta tcaccagtga     960
ggagcaggac gtgagccccc gccctgcacc tctgctgtta acacccccag ccatcccttc    1020
tttcaaaagg gatcctttca taggagaaca cactgaggag atacttgaag aatttggatt    1080
cagccgcgaa gagatttatc agcttaactc agataaaatc attgaaagta ataaggtaaa    1140
agctagtctc taacttccag gcccacggct caagtgaatt tgaatactgc atttacagtg    1200
tagagtaaca cataacattg tatgcatgga acatggagg aacagtatta cagtgtccta    1260
ccactctaat caagaaaaga attacagact ctgattctac agtgatgatt gaattctaaa    1320
aatggttatc attagggctt ttgatttata aactttggg tacttatact aaattatggt    1380
agttattctg ccttccagtt tgcttgatat atttgttgat attaagattc ttgacttata    1440
ttttgaatgg gttctagtga aaaggaatg atatattctt gaagacatcg atatacattt    1500
atttacactc ttgattctac aatgtagaaa atgaggaaat gccacaaatt gtatggtgat    1560
aaaagtcacg tgaaacaaaa aaaaaaaaaa aaaaaaaaaa aaaaaaaaaa aaaaaaaaaa    1620
a                                                                   1621
```

<210> SEQ ID NO 108
<211> LENGTH: 382
<212> TYPE: PRT
<213> ORGANISM: Homo sapien

<400> SEQUENCE: 108

```
Met Ala Leu Gln Gly Ile Ser Val Met Glu Leu Ser Gly Leu Ala Pro
 1               5                  10                  15

Gly Pro Phe Cys Ala Met Val Leu Ala Asp Phe Gly Ala Arg Val Val
                20                  25                  30

Arg Val Asp Arg Pro Gly Ser Arg Tyr Asp Val Ser Arg Leu Gly Arg
            35                  40                  45

Gly Lys Arg Ser Leu Val Leu Asp Leu Lys Gln Pro Arg Gly Ala Ala
        50                  55                  60

Val Leu Arg Arg Leu Cys Lys Ser Asp Val Leu Leu Glu Pro Phe
 65                  70                  75                  80
```

-continued

```
Arg Arg Gly Val Met Glu Lys Leu Gln Leu Gly Pro Glu Ile Leu Gln
                85                  90                  95
Arg Glu Asn Pro Arg Leu Ile Tyr Ala Arg Leu Ser Gly Phe Gly Gln
            100                 105                 110
Ser Gly Ser Phe Cys Arg Leu Ala Gly His Asp Ile Asn Tyr Leu Ala
        115                 120                 125
Leu Ser Gly Val Leu Ser Lys Ile Gly Arg Ser Gly Glu Asn Pro Tyr
    130                 135                 140
Ala Pro Leu Asn Leu Leu Ala Asp Phe Ala Gly Gly Leu Met Cys
145                 150                 155                 160
Ala Leu Gly Ile Ile Met Ala Leu Phe Asp Arg Thr Arg Thr Asp Lys
                165                 170                 175
Gly Gln Val Ile Asp Ala Asn Met Val Glu Gly Thr Ala Tyr Leu Ser
            180                 185                 190
Ser Phe Leu Trp Lys Thr Gln Lys Ser Ser Leu Trp Glu Ala Pro Arg
        195                 200                 205
Gly Gln Asn Met Leu Asp Gly Gly Ala Pro Phe Tyr Thr Thr Tyr Arg
    210                 215                 220
Thr Ala Asp Gly Glu Phe Met Ala Val Gly Ala Ile Glu Pro Gln Phe
225                 230                 235                 240
Tyr Glu Leu Leu Ile Lys Gly Leu Gly Leu Lys Ser Asp Glu Leu Pro
                245                 250                 255
Asn Gln Met Ser Met Asp Asp Trp Pro Glu Met Lys Lys Lys Phe Ala
            260                 265                 270
Asp Val Phe Ala Lys Lys Thr Lys Ala Glu Trp Cys Gln Ile Phe Asp
        275                 280                 285
Gly Thr Asp Ala Cys Val Thr Pro Val Leu Thr Phe Glu Glu Val Val
    290                 295                 300
His His Asp His Asn Lys Glu Arg Gly Ser Phe Ile Thr Ser Glu Glu
305                 310                 315                 320
Gln Asp Val Ser Pro Arg Pro Ala Pro Leu Leu Leu Asn Thr Pro Ala
                325                 330                 335
Ile Pro Ser Phe Lys Arg Asp Pro Phe Ile Gly Glu His Thr Glu Glu
            340                 345                 350
Ile Leu Glu Glu Phe Gly Phe Ser Arg Glu Glu Ile Tyr Gln Leu Asn
        355                 360                 365
Ser Asp Lys Ile Ile Glu Ser Asn Lys Val Lys Ala Ser Leu
    370                 375                 380
```

<210> SEQ ID NO 109
<211> LENGTH: 1524
<212> TYPE: DNA
<213> ORGANISM: Homo sapien

<400> SEQUENCE: 109

```
ggcacgaggc tgcgccaggg cctgagcgga ggcgggggca gcctcgccag cgggggcccc      60
gggcctggcc atgcctcact gagccagcgc ctgcgcctct acctcgccga cagctggaac     120
cagtgcgacc tagtggctct cacctgcttc ctcctgggcg tgggctgccg gctgaccccg     180
ggtttgtacc acctgggccg cactgtcctc tgcatcgact tcatggtttt cacggtgcgg     240
ctgcttcaca tcttcacggt caacaaacag ctggggccca gatcgtcat cgtgagcaag      300
atgatgaagg acgtgttctt cttcctcttc ttcctcggcg tgtggctggt agcctatggc     360
gtggccacgg aggggctcct gaggccacgg gacagtgact tcccaagtat cctgcgccgc     420
```

-continued

| | | |
|---|---|---|
| gtcttctacc gtccctacct gcagatcttc gggcagattc cccaggagga catgacgtg | 480 |
| gccctcatgg agcacagcaa ctgctcgtcg agcccggct tctgggcaca ccctcctggg | 540 |
| gcccaggcgg gcacctgcgt ctcccagtat gccaactggc tggtggtgct gctcctcgtc | 600 |
| atcttcctgc tcgtggccaa catcctgctg gtcaacttgc tcattgccat gttcagttac | 660 |
| acattcggca agtacaggg caacagcgat ctctactgga aggcgcagcg ttaccgcctc | 720 |
| atccgggaat tccactctcg gcccgcgctg gccccgccct ttatcgtcat ctcccacttg | 780 |
| cgcctcctgc tcaggcaatt gtgcaggcga ccccggagcc cccagccgtc ctccccggcc | 840 |
| ctcgagcatt tccgggttta cctttctaag gaagccgagc ggaagctgct aacgtgggaa | 900 |
| tcggtgcata aggagaactt tctgctggca cgcgctaggg acaagcggga gagcgactcc | 960 |
| gagcgtctga agcgcacgtc ccagaaggtg gacttggcac tgaaacagct gggacacatc | 1020 |
| cgcgagtacg aacagcgcct gaaagtgctg gagcgggagg tccagcagtg tagccgcgtc | 1080 |
| ctggggtggg tggccgaggc cctgagccgc tctgccttgc tgccccagg tgggccgcca | 1140 |
| cccccctgacc tgcctgggtc caaagactga gccctgctgg cggacttcaa ggagaagccc | 1200 |
| ccacaggga ttttgctcct agagtaaggc tcatctgggc ctcggccccc gcacctggtg | 1260 |
| gccttgtcct tgaggtgagc cccatgtcca tctgggccac tgtcaggacc acctttggga | 1320 |
| gtgtcatcct tacaaaccac agcatgcccg gctcctccca gaaccagtcc cagcctggga | 1380 |
| ggatcaaggc ctggatcccg ggccgttatc catctggagg ctgcagggtc cttggggtaa | 1440 |
| cagggaccac agacccctca ccactcacag attcctcaca ctggggaaat aaagccattt | 1500 |
| cagaggaaaa aaaaaaaaa aaaa | 1524 |

<210> SEQ ID NO 110
<211> LENGTH: 3410
<212> TYPE: DNA
<213> ORGANISM: Homo sapien

<400> SEQUENCE: 110

| | | |
|---|---|---|
| gggaaccagc ctgcacgcgc tggctccggg tgacagccgc gcgcctcggc caggatctga | 60 |
| gtgatgagac gtgtccccac tgaggtgccc cacagcagca ggtgttgagc atgggctgag | 120 |
| aagctggacc ggcaccaaag ggctggcaga aatgggcgcc tggctgattc ctaggcagtt | 180 |
| ggcggcagca aggaggagag gccgcagctt ctggagcaga gccgagacga agcagttctg | 240 |
| gagtgcctga acgcccccct gagccctacc cgcctggccc actatggtcc agaggctgtg | 300 |
| ggtgagccgc ctgctgcggc accggaaagc ccagctcttg ctggtcaacc tgctaacctt | 360 |
| tggcctggag gtgtgtttgg ccgcaggcat cacctatgtg ccgcctctgc tgctggaagt | 420 |
| gggggtagag gagaagttca tgaccatggt gctgggcatt ggtccagtgc tgggcctggt | 480 |
| ctgtgtcccg ctcctaggct cagccagtga ccactgcgt ggacgctatg gccgccgccg | 540 |
| gcccttcatc tgggcactgt ccttgggcat cctgctgagc ctctttctca tcccaagggc | 600 |
| cggctggcta gcagggctgc tgtgcccgga tcccaggccc ctggagctgg cactgctcat | 660 |
| cctgggcgtg gggctgctgg acttctgtgg ccaggtgtgc ttcactccac tggaggccct | 720 |
| gctctctgac ctcttccggg accggaccag ctgtcgccag gctactctg tctatgcctt | 780 |
| catgatcagt cttggggct gcctgggcta cctcctgcct gccattgact gggacaccag | 840 |
| tgccctggcc ccctacctgg gcacccagga ggagtgcctc tttggcctgc tcaccctcat | 900 |
| cttcctcacc tgcgtagcag ccacactgct ggtggctgag gaggcagcgc tgggcccac | 960 |
| cgagccagca gaagggctgt cggccccctc cttgtcgccc cactgctgtc catgccgggc | 1020 |

-continued

```
ccgcttggct ttccggaacc tgggcgccct gcttccccgg ctgcaccagc tgtgctgccg   1080
catgccccgc accctgcgcc ggctcttcgt ggctgagctg tgcagctgga tggcactcat   1140
gaccttcacg ctgttttaca cggatttcgt gggcgagggg ctgtaccagg gcgtgcccag   1200
agctgagccg ggcaccgagg cccggagaca ctatgatgaa ggcgttcgga tgggcagcct   1260
ggggctgttc ctgcagtgcg ccatctccct ggtcttctct ctggtcatgg accggctggt   1320
gcagcgattc ggcactcgag cagtctattt ggccagtgtg gcagctttcc ctgtggctgc   1380
cggtgccaca tgcctgtccc acagtgtggc cgtggtgaca gcttcagccg ccctcaccgg   1440
gttcaccttc tcagccctgc agatcctgcc ctacacactg gcctccctct accaccggga   1500
gaagcaggtg ttcctgccca ataccgaggg gacactgga ggtgctagca gtgaggacag   1560
cctgatgacc agcttcctgc caggccctaa gcctggagct cccttcccta atggacacgt   1620
gggtgctgga ggcagtggcc tgctcccacc tccacccgcg ctctgcgggg cctctgcctg   1680
tgatgtctcc gtacgtgtgg tggtgggtga gcccaccgag gccagggtgg ttccgggccg   1740
gggcatctgc ctggacctcg ccatcctgga tagtgccttc ctgctgtccc aggtggcccc   1800
atccctgttt atgggctcca ttgtccagct cagccagtct gtcactgcct atatggtgtc   1860
tgccgcaggc ctgggtctgg tcgccattta ctttgctaca caggtagtat ttgacaagag   1920
cgacttggcc aaatactcag cgtagaaaac ttccagcaca ttggggtgga gggcctgcct   1980
cactgggtcc cagctccccg ctcctgttag ccccatgggg ctgccgggct ggccgccagt   2040
ttctgttgct gccaaagtaa tgtggctctc tgctgccacc ctgtgctgct gaggtgcgta   2100
gctgcacagc tgggggctgg ggcgtccctc tcctctctcc ccagtctcta gggctgcctg   2160
actggaggcc ttccaagggg gtttcagtct ggacttatac agggaggcca gaagggctcc   2220
atgcactgga atgcggggac tctgcaggtg gattacccag gctcagggtt aacagctagc   2280
ctcctagttg agacacacct agagaagggt ttttgggagc tgaataaact cagtcacctg   2340
gtttcccatc tctaagcccc ttaacctgca gcttcgttta atgtagctct tgcatgggag   2400
tttctaggat gaaacactcc tccatgggat ttgaacatat gacttatttg taggggaaga   2460
gtcctgaggg gcaacacaca agaaccaggt cccctcagcc cacagcactg tcttttttgct   2520 gatccacccc cctcttacct tttatcagga tgtggcctgt tggtccttct gttgccatca   2580
cagagacaca ggcatttaaa tatttaactt atttatttaa caaagtagaa gggaatccat   2640
tgctagcttt tctgtgttgg tgtctaatat ttgggtaggg tgggggatcc ccaacaatca   2700
ggtcccctga gatagctggt cattgggctg atcattgcca gaatcttctt ctcctggggt   2760
ctggcccccc aaaatgccta acccaggacc ttggaaattc tactcatccc aaatgataat   2820
tccaaatgct gttacccaag gttagggtgt tgaaggaagg tagagggtgg ggcttcaggt   2880
ctcaacggct tccctaacca cccctcttct cttggcccag cctggttccc cccacttcca   2940
ctcccctcta ctctctctag gactgggctg atgaaggcac tgcccaaaat ttcccctacc   3000
cccaactttc ccctaccccc aactttcccc accagctcca caaccctgtt ggagctact   3060 gcaggaccag aagcacaaag tgcggtttcc caagcctttg tccatctcag cccccagagt   3120
atatctgtgc ttggggaatc tcacacagaa actcaggagc accccctgcc tgagctaagg   3180
gaggtcttat ctctcagggg gggtttaagt gccgtttgca ataatgtcgt cttatttatt   3240
tagcggggtg aatattttat actgtaagtg agcaatcaga gtataatgtt tatggtgaca   3300
aaattaaagg cttttcttata tgtttaaaaa aaaaaaaaaa aaaaaaaaa aaaaaaaaa    3360
```

```
aaaaaaaara aaaaaaaaaa aaaaaaaaaa aaaaaaataa aaaaaaaaaa         3410
```

<210> SEQ ID NO 111
<211> LENGTH: 1289
<212> TYPE: DNA
<213> ORGANISM: Homo sapien

<400> SEQUENCE: 111

```
agccaggcgt ccctctgcct gcccactcag tggcaacacc cgggagctgt tttgtccttt    60
gtggagcctc agcagttccc tctttcagaa ctcactgcca agagccctga acaggagcca   120
ccatgcagtg cttcagcttc attaagacca tgatgatcct cttcaatttg ctcatctttc   180
tgtgtggtgc agccctgttg gcagtgggca tctgggtgtc aatcgatggg gcatcctttc   240
tgaagatctt cgggccactg tcgtccagtg ccatgcagtt tgtcaacgtg ggctacttcc   300
tcatcgcagc cggcgttgtg gtctttgctc ttggtttcct gggctgctat ggtgctaaga   360
ctgagagcaa gtgtgccctc gtgacgttct tcttcatcct cctcctcatc ttcattgctg   420
aggttgcagc tgctgtggtc gccttggtgt acaccacaat ggctgagcac ttcctgacgt   480
tgctggtagt gcctgccatc aagaaagatt atggttccca ggaagacttc actcaagtgt   540
ggaacaccac catgaaaggg ctcaagtgct gtggcttcac caactatacg gattttgagg   600
actcacccta cttcaaagag aacagtgcct ttcccccatt ctgttgcaat gacaacgtca   660
ccaacacagc caatgaaacc tgcaccaagc aaaaggctca cgaccaaaaa gtagagggtt   720
gcttcaatca gcttttgtat gacatccgaa ctaatgcagt caccgtgggt ggtgtggcag   780
ctggaattgg gggcctcgag ctggctgcca tgattgtgtc catgtatctg tactgcaatc   840
tacaataagt ccacttctgc ctctgccact actgctgcca catgggaact gtgaagaggc   900
accctggcaa gcagcagtga ttgggggagg ggacaggatc taacaatgtc acttgggcca   960
gaatggacct gcccttctg ctccagactt ggggctagat agggaccact cctttttagcg  1020
atgcctgact tccttccat tggtgggtgg atgggtgggg ggcattccag agcctctaag   1080
gtagccagtt ctgttgccca ttcccccagt ctattaaacc cttgatatgc ccctaggcc   1140
tagtggtgat cccagtgctc tactggggga tgagagaaag gcattttata gcctgggcat  1200
aagtgaaatc agcagagcct ctgggtggat gtgtagaagg cacttcaaaa tgcataaacc  1260
tgttacaatg ttaaaaaaaa aaaaaaaaa                                     1289
```

<210> SEQ ID NO 112
<211> LENGTH: 315
<212> TYPE: PRT
<213> ORGANISM: Homo sapien

<400> SEQUENCE: 112

```
Met Val Phe Thr Val Arg Leu Leu His Ile Phe Thr Val Asn Lys Gln
 1               5                  10                  15

Leu Gly Pro Lys Ile Val Ile Val Ser Lys Met Met Lys Asp Val Phe
             20                  25                  30

Phe Phe Leu Phe Phe Leu Gly Val Trp Leu Val Ala Tyr Gly Val Ala
         35                  40                  45

Thr Glu Gly Leu Leu Arg Pro Arg Asp Ser Asp Phe Pro Ser Ile Leu
     50                  55                  60

Arg Arg Val Phe Arg Pro Tyr Leu Gln Ile Phe Gly Gln Ile Pro
 65                  70                  75                  80

Gln Glu Asp Met Asp Val Ala Leu Met Glu His Ser Asn Cys Ser Ser
             85                  90                  95
```

```
Glu Pro Gly Phe Trp Ala His Pro Pro Gly Ala Gln Ala Gly Thr Cys
            100                 105                 110
Val Ser Gln Tyr Ala Asn Trp Leu Val Val Leu Leu Val Ile Phe
        115                 120                 125
Leu Leu Val Ala Asn Ile Leu Leu Val Asn Leu Leu Ile Ala Met Phe
130                 135                 140
Ser Tyr Thr Phe Gly Lys Val Gln Gly Asn Ser Asp Leu Tyr Trp Lys
145                 150                 155                 160
Ala Gln Arg Tyr Arg Leu Ile Arg Glu Phe His Ser Arg Pro Ala Leu
                165                 170                 175
Ala Pro Pro Phe Ile Val Ile Ser His Leu Arg Leu Leu Arg Gln
            180                 185                 190
Leu Cys Arg Arg Pro Arg Ser Pro Gln Pro Ser Ser Pro Ala Leu Glu
        195                 200                 205
His Phe Arg Val Tyr Leu Ser Lys Glu Ala Glu Arg Lys Leu Leu Thr
        210                 215                 220
Trp Glu Ser Val His Lys Glu Asn Phe Leu Leu Ala Arg Ala Arg Asp
225                 230                 235                 240
Lys Arg Glu Ser Asp Ser Glu Arg Leu Lys Arg Thr Ser Gln Lys Val
                245                 250                 255
Asp Leu Ala Leu Lys Gln Leu Gly His Ile Arg Glu Tyr Glu Gln Arg
            260                 265                 270
Leu Lys Val Leu Glu Arg Glu Val Gln Gln Cys Ser Arg Val Leu Gly
        275                 280                 285
Trp Val Ala Glu Ala Leu Ser Arg Ser Ala Leu Leu Pro Pro Gly Gly
    290                 295                 300
Pro Pro Pro Asp Leu Pro Gly Ser Lys Asp
305                 310                 315

<210> SEQ ID NO 113
<211> LENGTH: 553
<212> TYPE: PRT
<213> ORGANISM: Homo sapien

<400> SEQUENCE: 113

Met Val Gln Arg Leu Trp Val Ser Arg Leu Leu Arg His Arg Lys Ala
1               5                   10                  15
Gln Leu Leu Leu Val Asn Leu Leu Thr Phe Gly Leu Glu Val Cys Leu
            20                  25                  30
Ala Ala Gly Ile Thr Tyr Val Pro Pro Leu Leu Glu Val Gly Val
        35                  40                  45
Glu Glu Lys Phe Met Thr Met Val Leu Gly Ile Gly Pro Val Leu Gly
    50                  55                  60
Leu Val Cys Val Pro Leu Leu Gly Ser Ala Ser Asp His Trp Arg Gly
65                  70                  75                  80
Arg Tyr Gly Arg Arg Arg Pro Phe Ile Trp Ala Leu Ser Leu Gly Ile
                85                  90                  95
Leu Leu Ser Leu Phe Leu Ile Pro Arg Ala Gly Trp Leu Ala Gly Leu
            100                 105                 110
Leu Cys Pro Asp Pro Arg Pro Leu Glu Leu Ala Leu Leu Ile Leu Gly
        115                 120                 125
Val Gly Leu Leu Asp Phe Cys Gly Gln Val Cys Phe Thr Pro Leu Glu
    130                 135                 140
Ala Leu Leu Ser Asp Leu Phe Arg Asp Pro Asp His Cys Arg Gln Ala
```

```
            145                 150                 155                 160
Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
                180                 185                 190

Gly Thr Gln Glu Glu Cys Leu Phe Gly Leu Leu Thr Leu Ile Phe Leu
                195                 200                 205

Thr Cys Val Ala Ala Thr Leu Leu Val Ala Glu Glu Ala Ala Leu Gly
                210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
                245                 250                 255

Leu Pro Arg Leu His Gln Leu Cys Cys Arg Met Pro Arg Thr Leu Arg
                260                 265                 270

Arg Leu Phe Val Ala Glu Leu Cys Ser Trp Met Ala Leu Met Thr Phe
                275                 280                 285

Thr Leu Phe Tyr Thr Asp Phe Val Gly Glu Gly Leu Tyr Gln Gly Val
                290                 295                 300

Pro Arg Ala Glu Pro Gly Thr Glu Ala Arg Arg His Tyr Asp Glu Gly
305                 310                 315                 320

Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg
                340                 345                 350

Ala Val Tyr Leu Ala Ser Val Ala Ala Phe Pro Val Ala Ala Gly Ala
                355                 360                 365

Thr Cys Leu Ser His Ser Val Ala Val Val Thr Ala Ser Ala Ala Leu
                370                 375                 380

Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
                405                 410                 415

Asp Thr Gly Gly Ala Ser Ser Glu Asp Ser Leu Met Thr Ser Phe Leu
                420                 425                 430

Pro Gly Pro Lys Pro Gly Ala Pro Phe Pro Asn Gly His Val Gly Ala
                435                 440                 445

Gly Gly Ser Gly Leu Leu Pro Pro Pro Ala Leu Cys Gly Ala Ser
                450                 455                 460

Ala Cys Asp Val Ser Val Arg Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
                500                 505                 510

Ile Val Gln Leu Ser Gln Ser Val Thr Ala Tyr Met Val Ser Ala Ala
                515                 520                 525

Gly Leu Gly Leu Ala Ile Tyr Phe Ala Thr Gln Val Val Phe Asp
                530                 535                 540

Lys Ser Asp Leu Ala Lys Tyr Ser Ala
545                 550

<210> SEQ ID NO 114
```

```
<211> LENGTH: 241
<212> TYPE: PRT
<213> ORGANISM: Homo sapien

<400> SEQUENCE: 114

Met Gln Cys Phe Ser Phe Ile Lys Thr Met Met Ile Leu Phe Asn Leu
 1               5                  10                  15

Leu Ile Phe Leu Cys Gly Ala Ala Leu Leu Ala Val Gly Ile Trp Val
             20                  25                  30

Ser Ile Asp Gly Ala Ser Phe Leu Lys Ile Phe Gly Pro Leu Ser Ser
         35                  40                  45

Ser Ala Met Gln Phe Val Asn Val Gly Tyr Phe Leu Ile Ala Ala Gly
     50                  55                  60

Val Val Val Phe Ala Leu Gly Phe Leu Gly Cys Tyr Gly Ala Lys Thr
 65                  70                  75                  80

Glu Ser Lys Cys Ala Leu Val Thr Phe Phe Ile Leu Leu Leu Ile
                 85                  90                  95

Phe Ile Ala Glu Val Ala Ala Ala Val Val Ala Leu Val Tyr Thr Thr
                100                 105                 110

Met Ala Glu His Phe Leu Thr Leu Leu Val Val Pro Ala Ile Lys Lys
                115                 120                 125

Asp Tyr Gly Ser Gln Glu Asp Phe Thr Gln Val Trp Asn Thr Thr Met
            130                 135                 140

Lys Gly Leu Lys Cys Cys Gly Phe Thr Asn Tyr Thr Asp Phe Glu Asp
145                 150                 155                 160

Ser Pro Tyr Phe Lys Glu Asn Ser Ala Phe Pro Pro Phe Cys Cys Asn
                165                 170                 175

Asp Asn Val Thr Asn Thr Ala Asn Glu Thr Cys Thr Lys Gln Lys Ala
            180                 185                 190

His Asp Gln Lys Val Glu Gly Cys Phe Asn Gln Leu Leu Tyr Asp Ile
        195                 200                 205

Arg Thr Asn Ala Val Thr Val Gly Gly Val Ala Ala Gly Ile Gly Gly
    210                 215                 220

Leu Glu Leu Ala Ala Met Ile Val Ser Met Tyr Leu Tyr Cys Asn Leu
225                 230                 235                 240

Gln

<210> SEQ ID NO 115
<211> LENGTH: 366
<212> TYPE: DNA
<213> ORGANISM: Homo sapien

<400> SEQUENCE: 115
gctctttctc tcccctcctc tgaatttaat tctttcaact tgcaatttgc aaggattaca      60
catttcactg tgatgtatat tgtgttgcaa aaaaaaaaaa gtgtctttgt ttaaaattac     120
ttggtttgtg aatccatctt gcttttccc cattggaact agtcattaac ccatctctga     180
actggtagaa aaacatctga agagctagtc tatcagcatc tgacaggtga attggatggt     240
tctcagaacc atttcaccca gacagcctgt ttctatcctg tttaataaat tagtttgggt     300
tctctacatg cataacaaac cctgctccaa tctgtcacat aaaagtctgt gacttgaagt     360
ttagtc                                                                366

<210> SEQ ID NO 116
<211> LENGTH: 282
<212> TYPE: DNA
```

<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 116
acaaagatga accatttcct atattatagc aaaattaaaa tctacccgta ttctaatatt    60
gagaaatgag atnaaacaca atnttataaa gtctacttag agaagatcaa gtgacctcaa   120
agactttact attttcatat tttaagacac atgatttatc ctattttagt aacctggttc   180
atacgttaaa caaaggataa tgtgaacagc agagaggatt tgttggcaga aaatctatgt   240
tcaatctnga actatctana tcacagacat ttctattcct tt                     282

<210> SEQ ID NO 117
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 117
acacatgtcg cttcactgcc ttcttagatg cttctggtca acatanagga acagggacca    60
tatttatcct ccctcctgaa acaattgcaa aataanacaa aatatatgaa acaattgcaa   120
aataaggcaa aatatatgaa acaacaggtc tcgagatatt ggaaatcagt caatgaagga   180
tactgatccc tgatcactgt cctaatgcag gatgtgggaa acagatgagg tcacctctgt   240
gactgcccca gcttactgcc tgtagagagt ttctangctg cagttcagac agggagaaat   300
tgggt                                                              305

<210> SEQ ID NO 118
<211> LENGTH: 71
<212> TYPE: DNA
<213> ORGANISM: Homo sapien
<220> FEATURE:
<221> NAME/KEY: misc_feature
<222> LOCATION: (1)...(71)
<223> OTHER INFORMATION: n = A,T,C or G

<400> SEQUENCE: 118
accaaggtgt ntgaatctct gacgtgggga tctctgattc ccgcacaatc tgagtggaaa    60
aantcctggg t                                                        71

<210> SEQ ID NO 119
<211> LENGTH: 212
<212> TYPE: DNA
<213> ORGANISM: Homo sapien
<220> FEATURE:
<221> NAME/KEY: misc_feature
<222> LOCATION: (1)...(212)
<223> OTHER INFORMATION: n = A,T,C or G

<400> SEQUENCE: 119
actccggttg gtgtcagcag cacgtggcat tgaacatngc aatgtggagc ccaaaccaca    60
gaaaatgggg tgaaattggc caactttcta tnaacttatg ttggcaantt tgccaccaac   120
agtaagctgg cccttctaat aaaagaaaat tgaaaggttt ctcactaanc ggaattaant   180
aatggantca aganactccc aggcctcagc gt                                 212

<210> SEQ ID NO 120
<211> LENGTH: 90
<212> TYPE: DNA
<213> ORGANISM: Homo sapien
<220> FEATURE:
<221> NAME/KEY: misc_feature
<222> LOCATION: (1)...(90)
<223> OTHER INFORMATION: n = A,T,C or G

<400> SEQUENCE: 120
actcgttgca natcaggggc cccccagagt caccgttgca ggagtccttc tggtcttgcc    60
ctccgccggc gcagaacatg ctggggtggt                                    90

<210> SEQ ID NO 121
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 121
tgtancgtga anacgacaga nagggttgtc aaaaatggag aanccttgaa gtcattttga    60
gaataagatt tgctaaaaga tttggggcta aaacatggtt attgggagac atttctgaag   120
atatncangt aaattangga atgaattcat ggttcttttg ggaattcctt tacgatngcc   180
agcatanact tcatgtgggg atancagcta cccttgta                           218

<210> SEQ ID NO 122
<211> LENGTH: 171
<212> TYPE: DNA
<213> ORGANISM: Homo sapien

<400> SEQUENCE: 122 tagggtgta tgcaactgta aggacaaaaa ttgagactca actggcttaa ccaataaagg    60
catttgttag ctcatggaac aggaagtcgg atggtggggc atcttcagtg ctgcatgagt   120
caccaccccg gcggggtcat ctgtgccaca ggtccctgtt gacagtgcgg t            171

<210> SEQ ID NO 123
<211> LENGTH: 76
<212> TYPE: DNA
<213> ORGANISM: Homo sapien
<220> FEATURE:
<221> NAME/KEY: misc_feature
<222> LOCATION: (1)...(76)
<223> OTHER INFORMATION: n = A,T,C or G

<400> SEQUENCE: 123
tgtagcgtga agacnacaga atggtgtgtg ctgtgctatc caggaacaca tttattatca    60
ttatcaanta ttgtgt                                                    76

<210> SEQ ID NO 124
<211> LENGTH: 131
<212> TYPE: DNA
<213> ORGANISM: Homo sapien

<400> SEQUENCE: 124
acctttcccc aaggccaatg tcctgtgtgc taactggccg gctgcaggac agctgcaatt    60 caatgtctg ggtcatatgg aggggaggag actctaaaat agccaattt attctcttgg    120 ttaagatttg t                                                        131

<210> SEQ ID NO 125
<211> LENGTH: 432
<212> TYPE: DNA
<213> ORGANISM: Homo sapien

<400> SEQUENCE: 125

```
actttatcta ctggctatga aatagatggt ggaaaattgc gttaccaact ataccactgg      60
cttgaaaaag aggtgatagc tcttcagagg acttgtgact tttgctcaga tgctgaagaa     120
ctacagtctg catttggcag aaatgaagat gaatttggat taaatgagga tgctgaagat     180
ttgcctcacc aaacaaaagt gaaacaactg agagaaaatt tcaggaaaa agacagtgg       240
ctcttgaagt atcagtcact tttgagaatg tttcttagtt actgcatact tcatggatcc     300
catggtgggg gtcttgcatc tgtaagaatg gaattgattt tgcttttgca agaatctcag     360
caggaaacat cagaaccact attttctagc cctctgtcag agcaaacctc agtgcctctc     420
ctctttgctt gt                                                         432
```

<210> SEQ ID NO 126
<211> LENGTH: 112
<212> TYPE: DNA
<213> ORGANISM: Homo sapien

<400> SEQUENCE: 126

```
acacaacttg aatagtaaaa tagaaactga gctgaaattt ctaattcact ttctaaccat      60
agtaagaatg atatttcccc ccagggatca ccaaatattt ataaaaattt gt             112
```

<210> SEQ ID NO 127
<211> LENGTH: 54
<212> TYPE: DNA
<213> ORGANISM: Homo sapien

<400> SEQUENCE: 127

```
accacgaaac cacaaacaag atggaagcat caatccactt gccaagcaca gcag            54
```

<210> SEQ ID NO 128
<211> LENGTH: 323
<212> TYPE: DNA
<213> ORGANISM: Homo sapien

<400> SEQUENCE: 128

```
acctcattag taattgtttt gttgtttcat ttttttctaa tgtctcccct ctaccagctc      60
acctgagata acagaatgaa aatggaagga cagccagatt tctcctttgc tctctgctca    120
ttctctctga agtctaggtt acccattttg gggacccatt ataggcaata aacacagttc    180
ccaaagcatt tggacagttt cttgttgtgt tttagaatgg ttttccttt tcttagcctt     240
ttcctgcaaa aggctcactc agtcccttgc ttgctcagtg gactgggctc cccagggcct    300
aggctgcctt cttttccatg tcc                                             323
```

<210> SEQ ID NO 129
<211> LENGTH: 192
<212> TYPE: DNA
<213> ORGANISM: Homo sapien
<220> FEATURE:
<221> NAME/KEY: misc_feature
<222> LOCATION: (1)...(192)
<223> OTHER INFORMATION: n = A,T,C or G

<400> SEQUENCE: 129

```
acatacatgt gtgtatattt ttaaatatca cttttgtatc actctgactt tttagcatac      60
```

| | |
|---|---|
| tgaaaacaca ctaacataat ttntgtgaac catgatcaga tacaacccaa atcattcatc | 120 |
| tagcacattc atctgtgata naaagatagg tgagtttcat ttccttcacg ttggccaatg | 180 |
| gataaacaaa gt | 192 |

<210> SEQ ID NO 130
<211> LENGTH: 362
<212> TYPE: DNA
<213> ORGANISM: Homo sapien
<220> FEATURE:
<221> NAME/KEY: misc_feature
<222> LOCATION: (1)...(362)
<223> OTHER INFORMATION: n = A,T,C or G

<400> SEQUENCE: 130

| | |
|---|---|
| ccctttttta tggaatgagt agactgtatg tttgaanatt tanccacaac ctctttgaca | 60 |
| tataatgacg caacaaaaag gtgctgttta gtcctatggt tcagtttatg ccctgacaa | 120 |
| gtttccattg tgttttgccg atcttctggc taatcgtggt atcctccatg ttattagtaa | 180 |
| ttctgtattc cattttgtta acgcctggta gatgtaacct gctangaggc taactttata | 240 |
| cttatttaaa agctcttatt ttgtggtcat taaaatggca atttatgtgc agcactttat | 300 |
| tgcagcagga agcacgtgtg ggttggttgt aaagctcttt gctaatctta aaagtaatg | 360 |
| gg | 362 |

<210> SEQ ID NO 131
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 131

| | |
|---|---|
| cttttttgaaa gatcgtgtcc actcctgtgg acatcttgtt ttaatggagt ttcccatgca | 60 |
| gtangactgg tatggttgca gctgtccaga taaaaacatt tgaagagctc caaaatgaga | 120 |
| gttctcccag gttcgccctg ctgctccaag tctcagcagc agcctctttt aggaggcatc | 180 |
| ttctgaacta gattaaggca gcttgtaaat ctgatgtgat ttggtttatt atccaactaa | 240 |
| cttccatctg ttatcactgg agaaagccca gactcccccan gacnggtacg gattgtgggc | 300 |
| atanaaggat tgggtgaagc tggcgttgtg gt | 332 |

<210> SEQ ID NO 132
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 132

| | |
|---|---|
| acttttgcca ttttgtatat ataaacaatc ttgggacatt ctcctgaaaa ctaggtgtcc | 60 |
| agtggctaag agaactcgat ttcaagcaat tctgaaagga aaaccagcat gacacagaat | 120 |
| ctcaaattcc caaacagggg ctctgtggga aaaatgaggg aggacctttg tatctcgggt | 180 |
| tttagcaagt taaaatgaan atgacaggaa aggcttattt atcaacaaag agaagagttg | 240 |
| ggatgcttct aaaaaaaact ttggtagaga aaataggaat gctnaatcct agggaagcct | 300 |

| gtaacaatct acaattggtc ca | 322 |

<210> SEQ ID NO 133
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G
<400> SEQUENCE: 133

| acaagccttc acaagtttaa ctaaattggg attaatcttt ctgtanttat ctgcataatt | 60 |
| cttgttttc tttccatctg gctcctgggt tgacaatttg tggaaacaac tctattgcta | 120 |
| ctatttaaaa aaaatcacaa atctttccct ttaagctatg ttnaattcaa actattcctg | 180 |
| ctattcctgt tttgtcaaag aaattatatt tttcaaaata tgtntatttg tttgatgggt | 240 |
| cccacgaaac actaataaaa accacagaga ccagcctg | 278 |

<210> SEQ ID NO 134
<211> LENGTH: 121
<212> TYPE: DNA
<213> ORGANISM: Homo sapien
<220> FEATURE:
<221> NAME/KEY: misc_feature
<222> LOCATION: (1)...(121)
<223> OTHER INFORMATION: n = A,T,C or G
<400> SEQUENCE: 134

| gtttanaaaa cttgtttagc tccatagagg aaagaatgtt aaactttgta ttttaaaaca | 60 |
| tgattctctg aggttaaact tggttttcaa atgttatttt tacttgtatt ttgcttttgg | 120 |
| t | 121 |

<210> SEQ ID NO 135
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G
<400> SEQUENCE: 135

| acttanaacc atgcctagca catcagaatc cctcaaagaa catcagtata atcctatacc | 60 |
| atancaagtg gtgactggtt aagcgtgcga caaaggtcag ctggcacatt acttgtgtgc | 120 |
| aaacttgata cttttgttct aagtaggaac tagtatacag tncctaggan tggtactcca | 180 |
| gggtgcccc caactcctgc agccgctcct ctgtgccagn ccctgnaagg aactttcgct | 240 |
| ccacctcaat caagccctgg gccatgctac ctgcaattgg ctgaacaaac gtttgctgag | 300 |
| ttcccaagga tgcaaagcct ggtgctcaac tcctggggcg tcaactcagt | 350 |

<210> SEQ ID NO 136
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G
<400> SEQUENCE: 136

| tgtaccgtga agacgacaga agttgcatgg cagggacagg gcagggccga ggccagggtt | 60 |

```
gctgtgattg tatccgaata ntcctcgtga gaaaagataa tgagatgacg tgagcagcct      120
gcagacttgt gtctgccttc aanaagccag acaggaaggc cctgcctgcc ttggctctga      180 cctgcggcc agccagccag ccacaggtgg gcttcttcct tttgtggtga caacnccaag       240
aaaactgcag aggcccaggg tcaggtgtna gtgggtangt gaccataaaa caccaggtgc      300
tcccaggaac ccgggcaaag gccatcccca cctacagcca gcatgcccac tggcgtgatg      360
ggtgcagang gatgaagcag ccagntgttc tgctgtggt                             399
```

<210> SEQ ID NO 137
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 137

```
actggtgtgg tnggggtga tgctggtggt anaagttgan gtgacttcan gatggtgtgt       60
ggaggaagtg tgtgaacgta gggatgtaga ngttttggcc gtgctaaatg agcttcggga     120
ttggctggtc ccactggtgg tcactgtcat tggtggggtt cctgt                    165
```

<210> SEQ ID NO 138
<211> LENGTH: 338
<212> TYPE: DNA
<213> ORGANISM: Homo sapien
<220> FEATURE:
<221> NAME/KEY: misc_feature
<222> LOCATION: (1)...(338)
<223> OTHER INFORMATION: n = A,T,C or G

<400> SEQUENCE: 138

```
actcactgga atgccacatt cacaacagaa tcagaggtct gtgaaaacat taatggctcc       60
ttaacttctc cagtaagaat cagggacttg aaatggaaac gttaacagcc acatgcccaa     120
tgctgggcag tctcccatgc cttccacagt gaaagggctt gagaaaatc acatccaatg      180 tcatgtgttt ccagccacac caaaaggtgc ttggggtgga gggctggggg catanangg t    240 cangcctcag gaagcctcaa gttccattca gctttgccac tgtacattcc ccatntttaa     300
aaaaactgat gcctttttttt ttttttttg taaaattc                             338
```

<210> SEQ ID NO 139
<211> LENGTH: 382
<212> TYPE: DNA
<213> ORGANISM: Homo sapien

<400> SEQUENCE: 139

```
gggaatcttg gttttttggca tctggttttgc ctatagccga ggccactttg acagaacaaa     60
gaaagggact tcgagtaaga aggtgattta cagccagcct agtgcccgaa gtgaaggaga     120
attcaaacag acctcgtcat tcctggtgtg agcctggtcg gctcaccgcc tatcatctgc     180
atttgcctta ctcaggtgct accggactct ggcccctgat gtctgtagtt tcacaggatg     240
ccttatttgt cttctacacc ccacagggcc cctacttct tcggatgtgt ttttaataat      300
gtcagctatg tgccccatcc tccttcatgc cctccctccc tttcctacca ctgctgagtg     360
gcctggaact tgtttaaagt gt                                              382
```

<210> SEQ ID NO 140

```
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 140 accaaancttt ctttctgttg tgttngattt tactataggg gtttngcttn ttctaaanat    60
acttttcatt taacancttt tgttaagtgt caggctgcac tttgctccat anaattattg   120
ttttcacatt tcaacttgta tgtgtttgtc tcttanagca ttggtgaaat cacatatttt   180
atattcagca taaaggagaa                                               200

<210> SEQ ID NO 141
<211> LENGTH: 335
<212> TYPE: DNA
<213> ORGANISM: Homo sapien
<220> FEATURE:
<221> NAME/KEY: misc_feature
<222> LOCATION: (1)...(335)
<223> OTHER INFORMATION: n = A,T,C or G

<400> SEQUENCE: 141
actttatttt caaaacactc atatgttgca aaaaacacat agaaaaataa agtttggtgg    60
gggtgctgac taaacttcaa gtcacagact tttatgtgac agattggagc agggtttgtt   120
atgcatgtag agaacccaaa ctaatttatt aaacaggata gaaacaggct gtctgggtga   180
aatggttctg agaaccatcc aattcacctg tcagatgctg atanactagc tcttcagatg   240
tttttctacc agttcagaga tnggttaatg actanttcca atggggaaaa agcaagatgg   300
attcacaaac caagtaattt taaacaaaga cactt                              335

<210> SEQ ID NO 142
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 142
accaggttaa tattgccaca tatatccttt ccaattgcgg gctaaacaga cgtgtattta    60
gggttgttta agacaaccc agcttaatat caagagaaat tgtgaccttt catggagtat   120
ctgatggaga aaacactgag ttttgacaaa tcttatttta ttcagatagc agtctgatca   180
cacatggtcc aacaacactc aaataataaa tcaaatatna tcagatgtta aagattggtc   240
ttcaaacatc atagccaatg atgccccgct tgcctataat ctctccgaca taaaaccaca   300
tcaacacctc agtggccacc aaaccattca gcacagcttc cttaactgtg agctgtttga   360
agctaccagt ctgagcacta ttgactatnt ttttcangct ctgaatagct ctagggatct   420
cagcangggt gggaggaacc agctcaacct tggcgtant                         459

<210> SEQ ID NO 143
<211> LENGTH: 140
<212> TYPE: DNA
<213> ORGANISM: Homo sapien

<400> SEQUENCE: 143
acatttcctt ccaccaagtc aggactcctg gcttctgtgg gagttcttat cacctgaggg    60
```
aaatccaaac agtctctcct agaaaggaat agtgtcacca accccaccca tctccctgag    120
accatccgac ttccctgtgt    140

<210> SEQ ID NO 144
<211> LENGTH: 164
<212> TYPE: DNA
<213> ORGANISM: Homo sapien
<220> FEATURE:
<221> NAME/KEY: misc_feature
<222> LOCATION: (1)...(164)
<223> OTHER INFORMATION: n = A,T,C or G

<400> SEQUENCE: 144
acttcagtaa caacatacaa taacaacatt aagtgtatat tgccatcttt gtcattttct    60
atctatacca ctctcccttc tgaaaacaan atcactanc caatcactta tacaaatttg    120
aggcaattaa tccatatttg ttttcaataa ggaaaaaaag atgt    164

<210> SEQ ID NO 145
<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 145
acgtagacca tccaactttg tatttgtaat ggcaaacatc cagnagcaat tcctaaacaa    60
actggagggt atttataccc aattatccca ttcattaaca tgccctcctc ctcaggctat    120
gcaggacagc tatcataagt cggcccaggc atccagatac taccatttgt ataaacttca    180 gtagggagt ccatccaagt gacaggtcta atcaaaggag gaaatggaac ataagcccag    240
tagtaaaatn ttgcttagct gaaacagcca caaaagactt accgccgtgg tgattaccat    300
caa    303

<210> SEQ ID NO 146
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 146
actgcagctc aattagaagt ggtctctgac tttcatcanc ttctccctgg gctccatgac    60
actggcctgg agtgactcat tgctctggtt ggttgagaga gctcctttgc caacaggcct    120
ccaagtcagg gctgggattt gtttcctttc cacattctag caacaatatg ctggccactt    180
cctgaacagg gagggtggga ggagccagca tggaacaagc tgccactttc taaagtagcc    240
agacttgccc ctgggcctgt cacacctact gatgaccttc tgtgcctgca ggatggaatg    300 tagggtgag ctgtgtgact ctatggt    327

<210> SEQ ID NO 147
<211> LENGTH: 173
<212> TYPE: DNA
<213> ORGANISM: Homo sapien
<220> FEATURE:
<221> NAME/KEY: misc_feature
<222> LOCATION: (1)...(173)

<223> OTHER INFORMATION: n = A,T,C or G

<400> SEQUENCE: 147

| acattgtttt tttgagataa agcattgana gagctctcct taacgtgaca caatggaagg | 60 |
|---|---|
| actggaacac atacccacat ctttgttctg agggataatt ttctgataaa gtcttgctgt | 120 |
| atattcaagc acatatgtta tatattattc agttccatgt ttatagccta gtt | 173 |

<210> SEQ ID NO 148
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 148

| acaaccactt tatctcatcg aattttaac ccaaactcac tcactgtgcc tttctatcct | 60 |
|---|---|
| atgggatata ttatttgatg ctccatttca tcacacatat atgaataata cactcatact | 120 |
| gccctactac ctgctgcaat aatcacattc ccttcctgtc ctgaccctga agccattggg | 180 |
| gtggtcctag tggccatcag tccangcctg caccttgagc ccttgagctc cattgctcac | 240 |
| nccancccac ctcaccgacc ccatcctctt acacagctac ctccttgctc tctaaccccc | 300 |
| tagattatnt ccaaattcag tcaattaagt tactattaac actctacccg acatgtccag | 360 |
| caccactggt aagccttctc cagccaacac acacacacac acacncacac acacacatat | 420 |
| ccaggcacag gctacctcat cttcacaatc acccctttaa ttaccatgct atggtgg | 477 |

<210> SEQ ID NO 149
<211> LENGTH: 207
<212> TYPE: DNA
<213> ORGANISM: Homo sapien

<400> SEQUENCE: 149

| acagttgtat tataatatca agaaataaac ttgcaatgag agcatttaag agggaagaac | 60 |
|---|---|
| taacgtatttt tagagagcca aggaaggttt ctgtggggag tgggatgtaa ggtggggcct | 120 |
| gatgataaat aagagtcagc caggtaagtg ggtggtgtgg tatgggcaca gtgaagaaca | 180 |
| tttcaggcag agggaacagc agtgaaa | 207 |

<210> SEQ ID NO 150
<211> LENGTH: 111
<212> TYPE: DNA
<213> ORGANISM: Homo sapien
<220> FEATURE:
<221> NAME/KEY: misc_feature
<222> LOCATION: (1)...(111)
<223> OTHER INFORMATION: n = A,T,C or G

<400> SEQUENCE: 150

| accttgattt cattgctgct ctgatggaaa cccaactatc taatttagct aaaacatggg | 60 |
|---|---|
| cacttaaatg tggtcagtgt ttggacttgt taactantgg catctttggg t | 111 |

<210> SEQ ID NO 151
<211> LENGTH: 196
<212> TYPE: DNA
<213> ORGANISM: Homo sapien

<400> SEQUENCE: 151

| agcgcggcag gtcatattga acattccaga tacctatcat tactcgatgc tgttgataac | 60 |

-continued

```
agcaagatgg ctttgaactc agggtcacca ccagctattg gaccttacta tgaaaaccat    120
ggataccaac cggaaaaccc ctatcccgca cagcccactg tggtcccac tgtctacgag     180 gtgcatccgg ctcagt                                                    196

<210> SEQ ID NO 152
<211> LENGTH: 132
<212> TYPE: DNA
<213> ORGANISM: Homo sapien

<400> SEQUENCE: 152
acagcacttt cacatgtaag aagggagaaa ttcctaaatg taggagaaag ataacagaac    60
cttccccttt tcatctagtg gtggaaacct gatgctttat gttgacagga atagaaccag    120
gagggagttt gt                                                       132

<210> SEQ ID NO 153
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 153
acaanaccca nganaggcca ctggccgtgg tgtcatggcc tccaaacatg aaagtgtcag    60
cttctgctct tatgtcctca tctgacaact ctttaccatt tttatcctcg ctcagcagga   120
gcacatcaat aaagtccaaa gtcttggact tggccttggc ttggaggaag tcatcaacac   180
cctggctagt gagggtgcgg cgccgctcct ggatgacggc atctgtgaag tcgtgcacca   240
gtctgcaggc cctgtggaag cgccgtccac acggagtnag gaatt                   285

<210> SEQ ID NO 154
<211> LENGTH: 333
<212> TYPE: DNA
<213> ORGANISM: Homo sapien

<400> SEQUENCE: 154
accacagtcc tgttgggcca gggcttcatg acccttctg tgaaaagcca tattatcacc    60
accccaaatt tttccttaaa tatctttaac tgaaggggtc agcctcttga ctgcaaagac   120
cctaagccgg ttacacagct aactcccact ggccctgatt tgtgaaattg ctgctgcctg   180
attggcacag gagtcgaagg tgttcagctc ccctcctccg tggaacgaga ctctgatttg   240
agtttcacaa attctcgggc cacctcgtca ttgctcctct gaaataaaat ccggagaatg   300
gtcaggcctg tctcatccat atggatcttc cgg                                333

<210> SEQ ID NO 155
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 155
actgaaaata ataaaaccca catcacagtg ttgtgtcaaa gatcatcagg gcatggatgg    60
gaaagtgctt tgggaactgt aaagtgccta acacatgatc gatgattttt gttataatat   120
```

| | |
|---|---|
| ttgaatcacg gtgcatacaa actctcctgc ctgctcctcc tgggcccag ccccagcccc | 180 |
| atcacagctc actgctctgt tcatccaggc ccagcatgta gtggctgatt cttcttggct | 240 |
| gcttttagcc tccanaagtt tctctgaagc caaccaaacc tctangtgta aggcatgctg | 300 |
| gccctggt | 308 |

<210> SEQ ID NO 156
<211> LENGTH: 295
<212> TYPE: DNA
<213> ORGANISM: Homo sapien

<400> SEQUENCE: 156

| | |
|---|---|
| accttgctcg gtgcttggaa catattagga actcaaaata tgagatgata acagtgccta | 60 |
| ttattgatta ctgagagaac tgttagacat ttagttgaag attttctaca caggaactga | 120 |
| gaataggaga ttatgtttgg ccctcatatt ctctcctatc ctccttgcct cattctatgt | 180 |
| ctaatatatt ctcaatcaaa taaggttagc ataatcagga aatcgaccaa ataccaatat | 240 |
| aaaaccagat gtctatcctt aagattttca aatagaaaac aaattaacag actat | 295 |

<210> SEQ ID NO 157
<211> LENGTH: 126
<212> TYPE: DNA
<213> ORGANISM: Homo sapien

<400> SEQUENCE: 157

| | |
|---|---|
| acaagtttaa atagtgctgt cactgtgcat gtgctgaaat gtgaaatcca ccacatttct | 60 |
| gaagagcaaa acaaattctg tcatgtaatc tctatcttgg gtcgtgggta tatctgtccc | 120 |
| cttagt | 126 |

<210> SEQ ID NO 158
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 158

| | |
|---|---|
| acccactggt cttggaaaca cccatcctta atacgatgat ttttctgtcg tgtgaaaatg | 60 |
| aanccagcag gctgcccta gtcagtcctt ccttccagag aaaagagat ttgagaaagt | 120 |
| gcctgggtaa ttcaccatta atttcctccc ccaaactctc tgagtcttcc cttaatattt | 180 |
| ctggtggttc tgaccaaagc aggtcatggt ttgttgagca tttgggatcc cagtgaagta | 240 |
| natgtttgta gccttgcata cttagccctt cccacgcaca aacggagtgg cagagtggtg | 300 |
| ccaaccctgt tttcccagtc cacgtagaca gattcacagt gcggaattct ggaagctgga | 360 |
| nacagacggg ctctttgcag agccgggact ctgagangga catgagggcc tctgcctctg | 420 |
| tgttcattct ctgatgtcct gt | 442 |

<210> SEQ ID NO 159
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 159

```
acttccaggt aacgttgttg tttccgttga gcctgaactg atgggtgacg ttgtaggttc    60
tccaacaaga actgaggttg cagagcgggt agggaagagt gctgttccag ttgcacctgg   120
gctgctgtgg actgttgttg attcctcact acggcccaag gttgtggaac tggcanaaag   180
gtgtgttgtt gganttgagc tcgggcggct gtggtaggtt gtgggctctt caacaggggc   240
tgctgtggtg ccgggangtg aangtgttgt gtcacttgag cttggccagc tctggaaagt   300
antanattct tcctgaaggc cagcgcttgt ggagctggca ngggtcantg ttgtgtgtaa   360
cgaaccagtg ctgctgtggg tgggtgtana tcctccacaa agcctgaagt tatggtgtcn   420
tcaggtaana atgtggtttc agtgtccctg ggcngctgtg aaggttgta nattgtcacc    480 aagggaataa gctgtggt                                                 498

<210> SEQ ID NO 160
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 160
acctgcatcc agcttccctg ccaaactcac aaggagacat caacctctag acagggaaac    60
agcttcagga tacttccagg agacagagcc accagcagca aaacaaatat tcccatgcct   120
ggagcatggc atagaggaag ctganaaatg tggggtctga ggaagccatt tgagtctggc   180
cactagacat ctcatcagcc acttgtgtga agagatgccc catgacccca gatgcctctc   240
ccacccttac ctccatctca cacacttgag cttcccactc tgtataattc taacatcctg   300
gagaaaaatg gcagtttgac cgaacctgtt cacaacggta gaggctgatt tctaacgaaa   360
cttgtagaat gaagcctgga                                               380

<210> SEQ ID NO 161
<211> LENGTH: 114
<212> TYPE: DNA
<213> ORGANISM: Homo sapien

<400> SEQUENCE: 161
actccacatc ccctctgagc aggcggttgt cgttcaaggt gtatttggcc ttgcctgtca    60
cactgtccac tggccccta tccacttggt gcttaatccc tcgaaagagc atgt          114

<210> SEQ ID NO 162
<211> LENGTH: 177
<212> TYPE: DNA
<213> ORGANISM: Homo sapien

<400> SEQUENCE: 162
actttctgaa tcgaatcaaa tgatacttag tgtagtttta atatcctcat atatatcaaa    60
gttttactac tctgataatt ttgtaaacca ggtaaccaga acatccagtc atacagcttt   120
tggtgatata taacttggca ataacccagt ctggtgatac ataaaactac tcactgt      177

<210> SEQ ID NO 163
<211> LENGTH: 137
<212> TYPE: DNA
<213> ORGANISM: Homo sapien
<220> FEATURE:
<221> NAME/KEY: misc_feature
<222> LOCATION: (1)...(137)
```

<223> OTHER INFORMATION: n = A,T,C or G

<400> SEQUENCE: 163

```
catttataca gacaggcgtg aagacattca cgacaaaaac gcgaaattct atcccgtgac    60
canagaaggc agctacggct actcctacat cctggcgtgg gtggccttcg cctgcacctt   120
catcagcggc atgatgt                                                  137
```

<210> SEQ ID NO 164
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 164

```
cttatcacaa tgaatgttct cctgggcagc gttgtgatct ttgccacctt cgtgactta    60
tgcaatgcat catgctattt catacctaat gagggagttc caggagattc aaccaggaaa   120
tgcatggatc tcaaaggaaa caaacaccca ataaactcgg agtggcagac tgacaactgt   180
gagacatgca cttgctacga aacagaaatt tcatgttgca cccttgtttc tacacctgtg   240
ggttatgaca agacaactg ccaaagaatc ttcaagaagg aggactgcaa gtatatcgtg   300
gtggagaaga aggacccaa aaagacctgt tctgtcagtg aatggataat ctaatgtgct   360
tctagtaggc acagggctcc caggccaggc ctcattctcc tctggcctct aatagtcaat   420
gattgtgtag ccatgcctat cagtaaaaag atntttgagc aaacacttt                469
```

<210> SEQ ID NO 165
<211> LENGTH: 195
<212> TYPE: DNA
<213> ORGANISM: Homo sapien
<220> FEATURE:
<221> NAME/KEY: misc_feature
<222> LOCATION: (1)...(195)
<223> OTHER INFORMATION: n = A,T,C or G

<400> SEQUENCE: 165

```
acagtttttt atanatatcg acattgccgg cacttgtgtt cagtttcata aagctggtgg    60
atccgctgtc atccactatt ccttggctag agtaaaaatt attcttatag cccatgtccc   120
tgcaggccgc ccgcccgtag ttctcgttcc agtcgtcttg gcacacaggg tgccaggact   180
tcctctgaga tgagt                                                    195
```

<210> SEQ ID NO 166
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 166

```
acatcttagt agtgtggcac atcagggggc catcagggtc acagtcactc atagcctcgc    60
cgaggtcgga gtccacacca ccggtgtagg tgtgctcaat cttgggcttg gcgcccacct   120
ttggagaagg gatatgctgc acacacatgt ccacaaagcc tgtgaactcg ccaaagaatt   180
tttgcagacc agcctgagca aggggcggat gttcagcttc agctcctcct tcgtcaggtg   240
gatgccaacc tcgtctangg tccgtgggaa gctggtgtcc acntcaccta caacctgggc   300
```

```
gangatctta taaagaggct ccnagataaa ctccacgaaa cttctctggg agctgctagt      360
nggggccttt ttggtgaact ttc                                             383
```

<210> SEQ ID NO 167
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 167

```
acagagccag accttggcca taaatgaanc agagattaag actaaacccc aagtcganat      60
tggagcagaa actggagcaa gaagtgggcc tggggctgaa gtagagacca aggccactgc     120
tatanccata cacagagcca actctcaggc caaggcnatg gttggggcag anccagagac    180
tcaatctgan tccaaagtgg tggctggaac actggtcatg acanaggcag tgactctgac    240 tgangtc                                                              247
```

<210> SEQ ID NO 168
<211> LENGTH: 273
<212> TYPE: DNA
<213> ORGANISM: Homo sapien
<220> FEATURE:
<221> NAME/KEY: misc_feature
<222> LOCATION: (1)...(273)
<223> OTHER INFORMATION: n = A,T,C or G

<400> SEQUENCE: 168

```
acttctaagt tttctagaag tggaaggatt gtantcatcc tgaaaatggg tttacttcaa      60
aatccctcan ccttgttctt cacnactgtc tatactgana gtgtcatgtt tccacaaagg     120
gctgacacct gagcctgnat tttcactcat ccctgagaag ccctttccag tagggtgggc    180
aattcccaac ttccttgcca caagcttccc aggctttctc ccctggaaaa ctccagcttg    240
agtcccagat acactcatgg gctgccctgg gca                                  273
```

<210> SEQ ID NO 169
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 169

```
acagccttgg cttccccaaa ctccacagtc tcagtgcaga aagatcatct tccagcagtc      60
agctcagacc agggtcaaag gatgtgacat caacagtttc tggtttcaga acaggttcta     120
ctactgtcaa atgaccccc atacttcctc aaaggctgtg gtaagttttg cacaggtgag    180
ggcagcagaa aggggtant tactgatgga caccatcttc tctgtatact ccacactgac    240
cttgccatgg gcaaaggccc ctaccacaaa acaatagga tcactgctgg gcaccagctc    300
acgcacatca ctgacaaccg ggatggaaaa agaantgcca actttcatac atccaactgg    360
aaagtgatct gatactggat tcttaattac cttcaaaagc ttctggggc catcagctgc    420 tcgaacactg a                                                         431
```

<210> SEQ ID NO 170

<211> LENGTH: 266
<212> TYPE: DNA
<213> ORGANISM: Homo sapien
<220> FEATURE:
<221> NAME/KEY: misc_feature
<222> LOCATION: (1)...(266)
<223> OTHER INFORMATION: n = A,T,C or G

<400> SEQUENCE: 170

| | | | | | |
|---|---|---|---|---|---|
| acctgtgggc | tgggctgtta | tgcctgtgcc | ggctgctgaa | agggagttca | gaggtggagc | 60 |
| tcaaggagct | ctgcaggcat | tttgccaanc | ctctccanag | canagggagc | aacctacact | 120 |
| ccccgctaga | aagacaccag | attggagtcc | tgggaggggg | agttggggtg | ggcatttgat | 180 |
| gtatacttgt | cacctgaatg | aangagccag | agaggaanga | gacgaanatg | anattggcct | 240 |
| tcaaagctag | gggtctggca | ggtgga | | | | 266 |

<210> SEQ ID NO 171
<211> LENGTH: 1248
<212> TYPE: DNA
<213> ORGANISM: Homo sapien
<220> FEATURE:
<221> NAME/KEY: misc_feature
<222> LOCATION: (1)...(1248)
<223> OTHER INFORMATION: n = A,T,C or G

<400> SEQUENCE: 171

| | | | | | |
|---|---|---|---|---|---|
| ggcagccaaa | tcataaacgg | cgaggactgc | agcccgcact | cgcagccctg | gcaggcggca | 60 |
| ctggtcatgg | aaaacgaatt | gttctgctcg | ggcgtcctgg | tgcatccgca | gtgggtgctg | 120 |
| tcagccgcac | actgtttcca | gaagtgagtg | cagagctcct | acaccatcgg | gctgggcctg | 180 |
| cacagtcttg | aggccgacca | agagccaggg | agccagatgt | ggaggccag | cctctccgta | 240 |
| cggcacccag | agtacaacag | acccttgctc | gctaacgacc | tcatgctcat | caagttggac | 300 |
| gaatccgtgt | ccgagtctga | caccatccgg | agcatcagca | ttgcttcgca | gtgccctacc | 360 |
| gcggggaact | cttgcctcgt | ttctggctgg | ggtctgctgg | cgaacggcag | aatgcctacc | 420 |
| gtgctgcagt | gcgtgaacgt | gtcggtggtg | tctgaggagg | tctgcagtaa | gctctatgac | 480 |
| ccgctgtacc | accccagcat | gttctgcgcc | ggcggagggc | aagaccagaa | ggactcctgc | 540 |
| aacggtgact | ctgggggggcc | cctgatctgc | aacgggtact | gcagggcct | tgtgtctttc | 600 |
| ggaaaagccc | cgtgtggcca | agttggcgtg | ccaggtgtct | acaccaacct | ctgcaaattc | 660 |
| actgagtgga | tagagaaaac | cgtccaggcc | agttaactct | ggggactggg | aacccatgaa | 720 |
| attgaccccc | aaatacatcc | tgcggaagga | attcaggaat | atctgttccc | agcccctcct | 780 |
| ccctcaggcc | caggagtcca | ggcccccagc | ccctcctccc | tcaaaccaag | ggtacagatc | 840 |
| cccagcccct | cctccctcag | acccaggagt | ccagaccccc | cagcccctcc | tccctcagac | 900 |
| ccaggagtcc | agcccctcct | ccctcagacc | caggagtcca | gacccccag | ccctcctcc | 960 |
| ctcagaccca | ggggtccagg | ccccaaccc | ctcctccctc | agactcagag | gtccaagccc | 1020 |
| ccaacccntc | attccccaga | cccagaggtc | caggtcccag | ccctcntcc | ctcagaccca | 1080 |
| gcggtccaat | gccacctaga | ctntccctgt | acacagtgcc | cccttgtggc | acgttgaccc | 1140 |
| aaccttacca | gttggttttt | catttttngt | cccttttcccc | tagatccaga | aataaagttt | 1200 |
| aagagaagng | caaaaaaaaa | aaaaaaaaa | aaaaaaaaaa | aaaaaaaa | | 1248 |

<210> SEQ ID NO 172
<211> LENGTH: 159
<212> TYPE: PRT
<213> ORGANISM: Homo sapien

```
<220> FEATURE:
<221> NAME/KEY: VARIANT
<222> LOCATION: (1)...(159)
<223> OTHER INFORMATION: Xaa = Any Amino Acid

<400> SEQUENCE: 172

Met Val Glu Ala Ser Leu Ser Val Arg His Pro Glu Tyr Asn Arg Pro
 1               5                  10                  15
Leu Leu Ala Asn Asp Leu Met Leu Ile Lys Leu Asp Glu Ser Val Ser
            20                  25                  30
Glu Ser Asp Thr Ile Arg Ser Ile Ser Ile Ala Ser Gln Cys Pro Thr
        35                  40                  45
Ala Gly Asn Ser Cys Leu Val Ser Gly Trp Gly Leu Leu Ala Asn Gly
    50                  55                  60
Arg Met Pro Thr Val Leu Gln Cys Val Asn Val Ser Val Val Ser Glu
65                  70                  75                  80
Glu Val Cys Ser Lys Leu Tyr Asp Pro Leu Tyr His Pro Ser Met Phe
                85                  90                  95
Cys Ala Gly Gly Gly Gln Xaa Gln Xaa Asp Ser Cys Asn Gly Asp Ser
            100                 105                 110
Gly Gly Pro Leu Ile Cys Asn Gly Tyr Leu Gln Gly Leu Val Ser Phe
        115                 120                 125
Gly Lys Ala Pro Cys Gly Gln Val Gly Val Pro Gly Val Tyr Thr Asn
    130                 135                 140
Leu Cys Lys Phe Thr Glu Trp Ile Glu Lys Thr Val Gln Ala Ser
145                 150                 155

<210> SEQ ID NO 173
<211> LENGTH: 1265
<212> TYPE: DNA
<213> ORGANISM: Homo sapien
<220> FEATURE:
<221> NAME/KEY: misc_feature
<222> LOCATION: (1)...(1265)
<223> OTHER INFORMATION: n = A,T,C or G

<400> SEQUENCE: 173
ggcagcccgc actcgcagcc ctggcaggcg gcactggtca tggaaaacga attgttctgc      60
tcgggcgtcc tggtgcatcc gcagtgggtg ctgtcagccg cacactgttt ccagaactcc     120
tacaccatcg ggctgggcct gcacagtctt gaggccgacc aagagccagg gagccagatg     180
gtggaggcca gcctctccgt acggcaccca gagtacaaca gacccttgct cgctaacgac     240
ctcatgctca tcaagttgga cgaatccgtg tccgagtctg acaccatccg gagcatcagc     300
attgcttcgc agtgccctac cgcggggaac tcttgcctcg tttctggctg gggtctgctg     360
gcgaacggtg agctcacggg tgtgtgtctg ccctcttcaa ggaggtcctc tgcccagtcg     420
cgggggctga cccagagctc tgcgtcccag gcagaatgcc taccgtgctg cagtgcgtga     480
acgtgtcggt ggtgtctgag gaggtctgca gtaagctcta tgacccgctg taccacccca     540
gcatgttctg cgccggcgga gggcaagacc agaaggactc tgcaacggt  gactctgggg     600
ggccccctgat ctgcaacggg tacttgcagg gccttgtgtc tttcggaaaa gccccgtgtg    660
gccaagttgg cgtgccaggt gtctacacca acctctgcaa attcactgag tggatagaga    720
aaaccgtcca ggccagttaa ctctggggac tgggaaccca tgaaattgac ccccaaatac    780
atcctgcgga aggaattcag gaatatctgt tcccagcccc cctccctca ggcccaggag     840
tccaggcccc cagcccctcc tccctcaaac caagggtaca gatccccagc cctcctccc     900
```

-continued

| | | |
|---|---|---|
| tcagacccag gagtccagac cccccagccc ctcctccctc agacccagga gtccagcccc | 960 | |
| tcctccntca gacccaggag tccagacccc ccagcccctc ctccctcaga cccaggggtt | 1020 | |
| gaggccccca acccctcctc cttcagagtc agaggtccaa gccccaacc cctcgttccc | 1080 | |
| cagacccaga ggtnnaggtc ccagcccctc ttccntcaga cccagnggtc caatgccacc | 1140 | |
| tagattttcc ctgnacacag tgcccccttg tggnangttg acccaaccct accagttggt | 1200 | |
| ttttcatttt tngtcccttt ccctagatc cagaaataaa gtttaagaga ngngcaaaaa | 1260 | |
| aaaaa | 1265 | |

<210> SEQ ID NO 174
<211> LENGTH: 1459
<212> TYPE: DNA
<213> ORGANISM: Homo sapien
<220> FEATURE:
<221> NAME/KEY: misc_feature
<222> LOCATION: (1)...(1459)
<223> OTHER INFORMATION: n = A,T,C or G

<400> SEQUENCE: 174

| | | |
|---|---|---|
| ggtcagccgc acactgtttc cagaagtgag tgcagagctc ctacaccatc gggctgggcc | 60 | |
| tgcacagtct tgaggccgac caagagccag ggagccagat ggtggaggcc agcctctccg | 120 | |
| tacggcaccc agagtacaac agacccttgc tcgctaacga cctcatgctc atcaagttgg | 180 | |
| acgaatccgt gtccgagtct gacaccatcc ggagcatcag cattgcttcg cagtgcccta | 240 | |
| ccgcggggaa ctcttgcctc gtttctggct ggggtctgct ggcgaacggt gagctcacgg | 300 | |
| gtgtgtgtct gccctcttca aggaggtcct ctgcccagtc gcggggctg acccagagct | 360 | |
| ctgcgtccca ggcagaatgc ctaccgtgct gcagtgcgtg aacgtgtcgg tggtgtctga | 420 | |
| ngaggtctgc antaagctct atgacccgct gtaccacccc ancatgttct gcgccggcgg | 480 | |
| agggcaagac cagaaggact cctgcaacgt gagagagggg aaaggggagg gcaggcgact | 540 | |
| cagggaaggg tggagaaggg ggagacagag acacacaggg ccgcatggcg agatgcagag | 600 | |
| atggagagac acagggag acagtgacaa ctagagagag aaactgagag aaacagagaa | 660 | |
| ataaacacag gaataaagag aagcaaagga agagagaaac agaaacagac atgggagggc | 720 | |
| agaaacacac acacatagaa atgcagttga ccttccaaca gcatggggcc tgagggcggt | 780 | |
| gacctccacc caatagaaaa tcctcttata acttttgact ccccaaaaac ctgactagaa | 840 | |
| atagcctact gttgacgggg agccttacca ataacataaa tagtcgattt atgcatacgt | 900 | |
| tttatgcatt catgatatac ctttgttgga attttttgat atttctaagc tacacagttc | 960 | |
| gtctgtgaat ttttttaaat tgttgcaact ctcctaaaat ttttctgatg tgtttattga | 1020 | |
| aaaatccaa gtataagtgg acttgtgcat tcaaaccagg gttgttcaag ggtcaactgt | 1080 | |
| gtacccagag ggaaacagtg acacagattc atagaggtga aacacgaaga gaaacaggaa | 1140 | |
| aaatcaagac tctacaaaga ggctgggcag ggtggctcat gcctgtaatc ccagcacttt | 1200 | |
| gggaggcgag gcaggcagat cacttgaggt aaggagttca agaccagcct ggccaaaatg | 1260 | |
| gtgaaatcct gtctgtacta aaaatacaaa agttagctgg atatggtggc aggcgcctgt | 1320 | |
| aatcccagct acttgggagg ctgaggcagg agaattgctt gaatatggga ggcagaggtt | 1380 | |
| gaagtgagtt gagatcacac cactatactc cagctgggc aacagagtaa gactctgtct | 1440 | |
| caaaaaaaaa aaaaaaaa | 1459 | |

<210> SEQ ID NO 175
<211> LENGTH: 1167

```
<212> TYPE: DNA
<213> ORGANISM: Homo sapien
<220> FEATURE:
<221> NAME/KEY: misc_feature
<222> LOCATION: (1)...(1167)
<223> OTHER INFORMATION: n = A,T,C or G

<400> SEQUENCE: 175
gcgcagccct ggcaggcggc actggtcatg gaaaacgaat tgttctgctc gggcgtcctg     60
gtgcatccgc agtgggtgct gtcagccgca cactgtttcc agaactccta caccatcggg    120
ctgggcctgc acagtcttga ggccgaccaa gagccaggga gccagatggt ggaggccagc    180
ctctccgtac ggcacccaga gtacaacaga ctcttgctcg ctaacgacct catgctcatc    240
aagttggacg aatccgtgtc cgagtctgac accatccgga gcatcagcat tgcttcgcag    300
tgccctaccg cggggaactc ttgcctcgtn tctggctggg gtctgctggc gaacggcaga    360
atgcctaccg tgctgcactg cgtgaacgtg tcggtggtgt ctgaggangt ctgcagtaag    420
ctctatgacc cgctgtacca ccccagcatg ttctgcgccg gcggagggca agaccagaag    480
gactcctgca acggtgactc tgggggggccc ctgatctgca acgggtactt gcagggcctt    540
gtgtctttcg gaaaagcccc gtgtggccaa cttggcgtgc aggtgtctca caccaacctc    600
tgcaaattca ctgagtggat agagaaaacc gtccagncca gttaactctg gggactggga    660
acccatgaaa ttgaccccca aatacatcct gcggaangaa ttcaggaata tctgttccca    720
gcccctcctc cctcaggccc aggagtccag gcccccagcc cctcctccct caaaccaagg    780
gtacagatcc ccagcccctc ctccctcaga cccaggagtc cagacccccc agcccctcnt    840
ccntcagacc caggagtcca gcccctcctc cntcagacgc aggagtccag accccccagc    900
ccntcntccg tcagacccag gggtgcaggc ccccaacccc tcntccntca gagtcagagg    960
tccaagcccc caaccctcg ttccccgac ccagaggtnc aggtcccagc ccctcctccc     1020
tcagacccag cggtccaatg ccacctagan tntccctgta cacagtgccc ccttgtggca    1080
ngttgaccca accttaccag ttggttttc atttttgtc cctttcccct agatccagaa      1140
ataaagtnta agagaagcgc aaaaaaa                                         1167

<210> SEQ ID NO 176
<211> LENGTH: 205
<212> TYPE: PRT
<213> ORGANISM: Homo sapien
<220> FEATURE:
<221> NAME/KEY: VARIANT
<222> LOCATION: (1)...(205)
<223> OTHER INFORMATION: Xaa = Any Amino Acid

<400> SEQUENCE: 176

Met Glu Asn Glu Leu Phe Cys Ser Gly Val Leu Val His Pro Gln Trp
  1               5                  10                  15

Val Leu Ser Ala Ala His Cys Phe Gln Asn Ser Tyr Thr Ile Gly Leu
                 20                  25                  30

Gly Leu His Ser Leu Glu Ala Asp Gln Glu Pro Gly Ser Gln Met Val
             35                  40                  45

Glu Ala Ser Leu Ser Val Arg His Pro Glu Tyr Asn Arg Leu Leu Leu
         50                  55                  60

Ala Asn Asp Leu Met Leu Ile Lys Leu Asp Glu Ser Val Ser Glu Ser
 65                  70                  75                  80

Asp Thr Ile Arg Ser Ile Ser Ile Ala Ser Gln Cys Pro Thr Ala Gly
                 85                  90                  95
```

```
Asn Ser Cys Leu Val Ser Gly Trp Gly Leu Leu Ala Asn Gly Arg Met
            100                 105                 110
Pro Thr Val Leu His Cys Val Asn Val Ser Val Ser Glu Xaa Val
            115                 120                 125
Cys Ser Lys Leu Tyr Asp Pro Leu Tyr His Pro Ser Met Phe Cys Ala
130             135                 140
Gly Gly Gly Gln Asp Gln Lys Asp Ser Cys Asn Gly Asp Ser Gly Gly
145                 150                 155                 160
Pro Leu Ile Cys Asn Gly Tyr Leu Gln Gly Leu Val Ser Phe Gly Lys
                165                 170                 175
Ala Pro Cys Gly Gln Leu Gly Val Pro Gly Val Tyr Thr Asn Leu Cys
            180                 185                 190
Lys Phe Thr Glu Trp Ile Glu Lys Thr Val Gln Xaa Ser
            195                 200                 205
```

```
<210> SEQ ID NO 177
<211> LENGTH: 1119
<212> TYPE: DNA
<213> ORGANISM: Homo sapien

<400> SEQUENCE: 177
gcgcactcgc agccctggca ggcggcactg gtcatggaaa acgaattgtt ctgctcgggc      60
gtcctggtgc atccgcagtg ggtgctgtca gccgcacact gtttccagaa ctcctacacc     120
atcgggctgg gcctgcacag tcttgaggcc gaccaagagc cagggagcca gatggtggag     180
gccagcctct ccgtacggca cccagagtac aacagaccct gctcgctaa cgacctcatg      240
ctcatcaagt tggacgaatc cgtgtccgag tctgacacca tccggagcat cagcattgct     300
tcgcagtgcc ctaccgcggg gaactcttgc ctcgtttctg gctgggtct gctggcgaac      360
gatgctgtga ttgccatcca gtcccagact gtgggaggct gggagtgtga aagcttccc      420
caaccctggc agggttgtac catttcggca acttccagtg caaggacgtc ctgctgcatc     480
ctcactgggt gctcactact gctcactgca tcacccggaa cactgtgatc aactagccag     540
caccatagtt ctccgaagtc agactatcat gattactgtg ttgactgtgc tgtctattgt     600
actaaccatg ccgatgttta ggtgaaatta gcgtcacttg gcctcaacca tcttggtatc     660
cagttatcct cactgaattg agatttcctg cttcagtgtc agccattccc acataatttc     720
tgacctacag aggtgaggga tcatatagct cttcaaggat gctggtactc ccctcacaaa     780
ttcatttctc ctgttgtagt gaaaggtgcg ccctctggag cctcccaggg tgggtgtgca     840
ggtcacaatg atgaatgtat gatcgtgttc ccattaccca aagcctttaa atccctcatg     900
ctcagtacac cagggcaggt ctagcatttc ttcatttagt gtatgctgtc cattcatgca     960
accacctcag gactcctgga ttctctgcct agttgagctc ctgcatgctg cctccttggg    1020
gaggtgaggg agagggccca tggttcaatg ggatctgtgc agttgtaaca cattaggtgc    1080
ttaataaaca gaagctgtga tgttaaaaaa aaaaaaaa                            1119

<210> SEQ ID NO 178
<211> LENGTH: 164
<212> TYPE: PRT
<213> ORGANISM: Homo sapien
<220> FEATURE:
<221> NAME/KEY: VARIANT
<222> LOCATION: (1)...(164)
<223> OTHER INFORMATION: Xaa = Any Amino Acid

<400> SEQUENCE: 178
```

```
Met Glu Asn Glu Leu Phe Cys Ser Gly Val Leu Val His Pro Gln Trp
 1               5                  10                  15
Val Leu Ser Ala Ala His Cys Phe Gln Asn Ser Tyr Thr Ile Gly Leu
             20                  25                  30
Gly Leu His Ser Leu Glu Ala Asp Gln Glu Pro Gly Ser Gln Met Val
         35                  40                  45
Glu Ala Ser Leu Ser Val Arg His Pro Glu Tyr Asn Arg Pro Leu Leu
     50                  55                  60
Ala Asn Asp Leu Met Leu Ile Lys Leu Asp Glu Ser Val Ser Glu Ser
65                  70                  75                  80
Asp Thr Ile Arg Ser Ile Ser Ile Ala Ser Gln Cys Pro Thr Ala Gly
                 85                  90                  95
Asn Ser Cys Leu Val Ser Gly Trp Gly Leu Leu Ala Asn Asp Ala Val
             100                 105                 110
Ile Ala Ile Gln Ser Xaa Thr Val Gly Gly Trp Glu Cys Glu Lys Leu
         115                 120                 125
Ser Gln Pro Trp Gln Gly Cys Thr Ile Ser Ala Thr Ser Ser Ala Arg
    130                 135                 140
Thr Ser Cys Cys Ile Leu Thr Gly Cys Ser Leu Leu Leu Thr Ala Ser
145                 150                 155                 160
Pro Gly Thr Leu
```

<210> SEQ ID NO 179
<211> LENGTH: 250
<212> TYPE: DNA
<213> ORGANISM: Homo sapien

<400> SEQUENCE: 179

```
ctggagtgcc ttggtgtttc aagcccctgc aggaagcaga atgcaccttc tgaggcacct      60
ccagctgccc ccggccgggg gatgcgaggc tcggagcacc cttgcccggc tgtgattgct     120
gccaggcact gttcatctca gcttttctgt cccttctcc ccggcaagcg cttctgctga     180
aagttcatat ctggagcctg atgtcttaac gaataaaggt cccatgctcc acccgaaaaa     240
aaaaaaaaaa                                                            250
```

<210> SEQ ID NO 180
<211> LENGTH: 202
<212> TYPE: DNA
<213> ORGANISM: Homo sapien

<400> SEQUENCE: 180

```
actagtccag tgtggtggaa ttccattgtg ttgggcccaa cacaatggct acctttaaca      60
tcacccagac cccgcccctg cccgtgcccc acgctgctgc taacgacagt atgatgctta     120
ctctgctact cggaaactat ttttatgtaa ttaatgtatg ctttcttgtt tataaatgcc     180
tgatttaaaa aaaaaaaaaa aa                                              202
```

<210> SEQ ID NO 181
<211> LENGTH: 558
<212> TYPE: DNA
<213> ORGANISM: Homo sapien
<220> FEATURE:
<221> NAME/KEY: misc_feature
<222> LOCATION: (1)...(558)
<223> OTHER INFORMATION: n = A,T,C or G

<400> SEQUENCE: 181

```
tccytttgkt naggttttkkg agacamcccck agacctwaan ctgtgtcaca gacttcyngg      60
```

```
aatgtttagg cagtgctagt aatttcytcg taatgattct gttattactt tcctnattct    120
ttattcctct ttcttctgaa gattaatgaa gttgaaaatt gaggtggata aatacaaaaa    180
ggtagtgtga tagtataagt atctaagtgc agatgaaagt gtgttatata tatccattca    240
aaattatgca agttagtaat tactcaggot taactaaatt actttaatat gctgttgaac    300
ctactctgtt ccttggctag aaaaaattat aaacaggact ttgttagttt gggaagccaa    360
attgataata ttctatgttc taaaagttgg gctatacata aattattaag aaatatggaw    420
ttttattccc aggaatatgg kgttcatttt atgaatatta cscrggatag awgtwtgagt    480
aaaaycagtt ttggtwaata ygtwaatatg tcmtaaataa acaakgcttt gacttatttc    540
caaaaaaaaa aaaaaaaa                                                  558
```

<210> SEQ ID NO 182
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 182

```
acagggwttk grggatgcta agsccccrga rwtygtttga tccaaccctg gcttwttttc     60 agagggaaa atgggccta gaagttacag mscatytagy tggtgcgmtg gcaccoctgg     120 cstcacacag astcccgagt agctgggact acaggcacac agtcactgaa gcaggccctg    180
ttwgcaattc acgttgccac ctccaactta aacattcttc atatgtgatg tccttagtca    240
ctaaggttaa actttcccac ccagaaaagg caacttagat aaaatcttag agtactttca    300
tactmttcta agtcctcttc cagcctcact kkgagtcctm cytgggggtt gataggaant    360
ntctcttggc tttctcaata aartctctat ycatctcatg tttaatttgg tacgcatara    420
awtgstgara aaattaaaat gttctggtty mactttaaaa araaaaaaaa aaaaaaaa     479
```

<210> SEQ ID NO 183
<211> LENGTH: 384
<212> TYPE: DNA
<213> ORGANISM: Homo sapien

<400> SEQUENCE: 183

```
aggcgggagc agaagctaaa gccaaagccc aagaagagtg gcagtgccag cactggtgcc     60
agtaccagta ccaataacag tgccagtgcc agtgccagca ccagtggtgg cttcagtgct    120
ggtgccagcc tgaccgccac tctcacattt gggctcttcg ctggccttgg tggagctggt    180
gccagcacca gtggcagctc tggtgcctgt ggtttctcct acaagtgaga ttttagatat    240
tgttaatcct gccagtcttt ctcttcaagc cagggtgcat cctcagaaac ctactcaaca    300
cagcactcta ggcagccact atcaatcaat tgaagttgac actctgcatt aratctatt     360 gccatttcaa aaaaaaaaaa aaaa                                           384
```

<210> SEQ ID NO 184
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 184

```
accgaattgg gaccgctggc ttataagcga tcatgtyynt ccrgtatkac ctcaacgagc     60
agggagatcg agtctatacg ctgaagaaat ttgacccgat gggacaacag acctgctcag   120
cccatcctgc tcggttctcc ccagatgaca aatactctsg acaccgaatc accatcaaga   180
aacgcttcaa ggtgctcatg acccagcaac cgcgccctgt cctctgaggg tcccttaaac   240
tgatgtcttt tctgccacct gttacccctc ggagactccg taaccaaact cttcggactg   300
tgagccctga tgccttttg ccagccatac tctttggcat ccagtctctc gtggcgattg    360
attatgcttg tgtgaggcaa tcatggtggc atcacccata aagggaacac atttgacttt   420
tttttctcat attttaaatt actacmagaw tattwmagaw waaatgawtt gaaaaactst   480
taaaaaaaaa aaaaaa                                                   496
```

<210> SEQ ID NO 185
<211> LENGTH: 384
<212> TYPE: DNA
<213> ORGANISM: Homo sapien

<400> SEQUENCE: 185

```
gctggtagcc tatggcgkgg cccacggagg ggctcctgag gccacggrac agtgacttcc     60
caagtatcyt gcgcsgcgtc ttctaccgtc cctacctgca gatcttcggg cagattcccc   120
aggaggacat ggacgtggcc ctcatggagc acagcaactg ytcgtcggag cccggcttct   180
gggcacaccc tcctggggcc caggcgggca cctgcgtctc ccagtatgcc aactggctgg   240
tggtgctgct cctcgtcatc ttcctgctcg tggccaacat cctgctggtc aacttgctca   300
ttgccatgtt cagttacaca ttcggcaaag tacagggcaa cagcgatctc tactgggaag   360
gcgcagcgtt accgcctcat ccgg                                           384
```

<210> SEQ ID NO 186
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 186

```
gagttagctc ctccacaacc ttgatgaggt cgtctgcagt ggcctctcgc ttcataccgc     60
tnccatcgtc atactgtagg tttgccacca cytcctggca tcttggggcg gcntaatatt   120
ccaggaaact ctcaatcaag tcaccgtcga tgaaacctgt gggctggttc tgtcttccgc   180
tcggtgtgaa aggatctccc agaaggagtg ctcgatcttc cccacacttt tgatgacttt   240
attgagtcga ttctgcatgt ccagcaggag gttgtaccag ctctctgaca gtgaggtcac   300
cagccctatc atgccgttga mcgtgccgaa garcaccgag ccttgtgtgg gggkkgaagt   360
ctcacccaga ttctgcatta ccagagagcc gtggcaaaag acattgacaa actcgcccag   420
gtggaaaaag amcamctcct ggargtgctn gccgctcctc gtcmgttggt ggcagcgctw   480
tccttttgac acacaaacaa gttaaaggca ttttcagccc cagaaantt gtcatcatcc    540
aagatntcgc acagcactna tccagttggg attaaat                             577
```

<210> SEQ ID NO 187
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 187

| | | | | | |
|---|---|---|---|---|---|
| aacatcttcc | tgtataatgc | tgtgtaatat | cgatccgatn | ttgtctgstg | agaatycatw | 60 |
| actkggaaaa | gmaacattaa | agcctggaca | ctggtattaa | aattcacaat | atgcaacact | 120 |
| ttaaacagtg | tgtcaatctg | ctcccyynac | tttgtcatca | ccagtctggg | aakaagggta | 180 |
| tgccctattc | acacctgtta | aagggcgct | aagcattttt | gattcaacat | cttttttttt | 240 |
| gacacaagtc | cgaaaaaagc | aaagtaaac | agttatyaat | ttgttagcca | attcactttc | 300 |
| ttcatgggac | agagccatyt | gatttaaaaa | gcaaattgca | taatattgag | cttygggagc | 360 |
| tgatatttga | gcggaagagt | agcctttcta | cttcaccaga | cacaactccc | tttcatattg | 420 |
| ggatgttnac | naaagtwatg | tctctwacag | atgggatgct | tttgtggcaa | ttctgttctg | 480 |
| aggatctccc | agtttattta | ccacttgcac | aagaaggcgt | tttcttcctc | aggc | 534 |

<210> SEQ ID NO 188
<211> LENGTH: 761
<212> TYPE: DNA
<213> ORGANISM: Homo sapien
<220> FEATURE:
<221> NAME/KEY: misc_feature
<222> LOCATION: (1)...(761)
<223> OTHER INFORMATION: n = A,T,C or G

<400> SEQUENCE: 188

| | | | | | |
|---|---|---|---|---|---|
| agaaaccagt | atctctnaaa | acaacctctc | ataccttgtg | gacctaattt | tgtgtgcgtg | 60 |
| tgtgtgtgcg | cgcatattat | atagacaggc | acatcttttt | tactttttgta | aaagcttatg | 120 |
| cctctttggt | atctatatct | gtgaaagttt | taatgatctg | ccataatgtc | ttggggacct | 180 |
| ttgtcttctg | tgtaaatggt | actagagaaa | acacctatnt | tatgagtcaa | tctagttngt | 240 |
| tttattcgac | atgaaggaaa | tttccagatn | acaaacactna | caaactctcc | ctkgackarg | 300 |
| ggggacaaag | aaaagcaaaa | ctgamcataa | raaacaatwa | cctggtgaga | arttgcataa | 360 |
| acagaaatwr | ggtagtatat | tgaarnacag | catcattaaa | rmgttwtktt | wttctcccctt | 420 |
| gcaaaaaaca | tgtacngact | tcccgttgag | taatgccaag | ttgttttttt | tatnataaaa | 480 |
| cttgcccttc | attacatgtt | tnaaagtggt | gtggtgggcc | aaaatattga | aatgatggaa | 540 |
| ctgactgata | aagctgtaca | aataagcagt | gtgcctaaca | agcaacacag | taatgttgac | 600 |
| atgcttaatt | cacaaatgct | aatttcatta | taaatgtttg | ctaaaataca | ctttgaacta | 660 |
| tttttctgtn | ttcccagagc | tgagatntta | gattttatgt | agtataaagt | gaaaantac | 720 |
| gaaataata | acattgaaga | aaaananaaa | aaanaaaaaa | a | | 761 |

<210> SEQ ID NO 189
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 189

| | | | | | |
|---|---|---|---|---|---|
| tttttttttt | tttgccgatn | ctactatttt | attgcaggan | gtgggggtgt | atgcaccgca | 60 |
| caccggggct | atnagaagca | agaaggaagg | agggagggca | cagccccttg | ctgagcaaca | 120 |

| aagccgcctg ctgccttctc tgtctgtctc ctggtgcagg cacatgggga gaccttcccc | 180 |
| aaggcagggg ccaccagtcc aggggtggga atacagggg tgggangtgt gcataagaag | 240 |
| tgataggcac aggccacccg gtacagaccc ctcggctcct gacaggtnga tttcgaccag | 300 |
| gtcattgtgc cctgcccagg cacagcgtan atctggaaaa gacagaatgc tttccttttc | 360 |
| aaatttggct ngtcatngaa ngggcanttt tccaanttng gctnggtctt ggtacncttg | 420 |
| gttcggccca gctccncgtc caaaaantat tcaccnnct ccnaattgct tgcnggnccc | 480 |
| cc | 482 |

<210> SEQ ID NO 190
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 190

| tttttttttt ttttaaaaca gtttttcaca acaaaattta ttagaagaat agtggttttg | 60 |
| aaaactctcg catccagtga gaactaccat acaccacatt acagctngga atgtnctcca | 120 |
| aatgtctggt caaatgatac aatggaacca ttcaatctta cacatgcacg aaagaacaag | 180 |
| cgcttttgac atacaatgca caaaaaaaaa aggggggggg gaccacatgg attaaaattt | 240 |
| taagtactca tcacatacat taagacacag ttctagtcca gtcnaaaatc agaactgcnt | 300 |
| tgaaaaattt catgtatgca atccaaccaa agaacttnat tggtgatcat gantnctcta | 360 |
| ctacatcnac cttgatcatt gccaggaacn aaaagttnaa ancacncgt acaaaaanaa | 420 |
| tctgtaattn anttcaacct ccgtacngaa aaatnttnnt tatacactcc c | 471 |

<210> SEQ ID NO 191
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 191

| gagggattga aggtctgttc tastgtcggm ctgttcagcc accaactcta acaagttgct | 60 |
| gtcttccact cactgtctgt aagctttta acccagacwg tatcttcata aatagaacaa | 120 |
| attcttcacc agtcacatct tctaggacct ttttggattc agttagtata agctcttcca | 180 |
| cttcctttgt taagacttca tctggtaaag tcttaagttt tgtagaaagg aattyaattg | 240 |
| ctcgttctct aacaatgtcc tctccttgaa gtatttggct gaacaaccca cctaaagtcc | 300 |
| ctttgtgcat ccattttaaa tatacttaat agggcattgk tncactaggt taaattctgc | 360 |
| aagagtcatc tgtctgcaaa agttgcgtta gtatatctgc ca | 402 |

<210> SEQ ID NO 192
<211> LENGTH: 601
<212> TYPE: DNA
<213> ORGANISM: Homo sapien
<220> FEATURE:
<221> NAME/KEY: misc_feature
<222> LOCATION: (1)...(601)
<223> OTHER INFORMATION: n = A,T,C or G

<400> SEQUENCE: 192

```
gagctcggat ccaataatct tgtctgagg gcagcacaca tatncagtgc catggnaact      60
ggtctacccc acatgggagc agcatgccgt agntatataa ggtcattccc tgagtcagac    120
atgcytyttt gaytaccgtg tgccaagtgc tggtgattct yaacacacyt ccatcccgyt    180
cttttgtgga aaaactggca cttktctgga actagcarga catcacttac aaattccccc    240
acgagacact tgaaaggtgt aacaaagcga ytcttgcatt gcttttttgtc cctccggcac   300 cagttgtcaa tactaacccg ctggtttgcc tccatcacat ttgtgatctg tagctctgga    360
tacatctcct gacagtactg aagaacttct tcttttgttt caaaagcarc tcttggtgcc    420
tgttggatca ggttcccatt tcccagtcyg aatgttcaca tggcatattt wacttcccac    480
aaaacattgc gatttgaggc tcagcaacag caaatcctgt tccggcattg gctgcaagag    540
cctcgatgta gccggccagc gccaaggcag gcgccgtgag ccccaccagc agcagaagca    600
g                                                                   601
```

<210> SEQ ID NO 193
<211> LENGTH: 608
<212> TYPE: DNA
<213> ORGANISM: Homo sapien
<220> FEATURE:
<221> NAME/KEY: misc_feature
<222> LOCATION: (1)...(608)
<223> OTHER INFORMATION: n = A,T,C or G

<400> SEQUENCE: 193

```
atacagccca natcccacca cgaagatgcg cttgttgact gagaacctga tgcggtcact    60
ggtcccgctg tagccccagc gactctccac ctgctggaag cggttgatgc tgcactcytt   120
cccaacgcag gcagmagcgg gsccggtcaa tgaactccay tcgtggcttg gggtkgacgg   180
tkaagtgcag gaagaggctg accacctcgc ggtccaccag gatgcccgac tgtgcgggac   240
ctgcagcgaa actcctcgat ggtcatgagc gggaagcgaa tgaggcccag ggccttgccc   300
agaaccttcc gcctgttctc tggcgtcacc tgcagctgct gccgctgaca ctcggcctcg   360
gaccagcgga caaacggcrt tgaacagccg cacctcacgg atgcccagtg tgtcgcgctc   420
caggammgsc accagcgtgt ccaggtcaat gtcggtgaag ccctccgcgg gtratggcgt   480
ctgcagtgtt tttgtcgatg ttctccaggc acaggctggc cagctgcggt tcatcgaaga   540
gtcgcgcctg cgtgagcagc atgaaggcgt tgtcggctcg cagttcttct tcaggaactc   600
cacgcaat                                                           608
```

<210> SEQ ID NO 194
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 194

```
gaacggctgg accttgcctc gcattgtgct tgctggcagg gaataccttg gcaagcagyt    60
ccagtccgag cagccccaga ccgctgccgc ccgaagctaa gcctgcctct ggccttcccc   120
tccgcctcaa tgcagaacca gtagtgggag cactgtgttt agagttaaga gtgaacactg   180
tttgatttta cttgggaatt tcctctgtta tatagctttt cccaatgcta atttccaaac   240
aacaacaaca aataacatg tttgcctgtt aagttgtata aagtaggtg attctgtatt    300
```

| | |
|---|---|
| taaagaaaat attactgtta catatactgc ttgcaatttc tgtatttatt gktnctstgg | 360 |
| aaataaatat agttattaaa ggttgtcant cc | 392 |

<210> SEQ ID NO 195
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 195

| | |
|---|---|
| ccsttkgagg ggtkaggkyc cagttyccga gtggaagaaa caggccagga gaagtgcgtg | 60 |
| ccgagctgag gcagatgttc ccacagtgac ccccagagcc stgggstata gtytctgacc | 120 |
| cctcncaagg aaagaccacs ttctggggac atgggctgga gggcaggacc tagaggcacc | 180 |
| aagggaaggc cccattccgg ggstgttccc cgaggaggaa gggaagggc tctgtgtgcc | 240 |
| ccccasgagg aagaggccct gagtcctggg atcagacacc ccttcacgtg tatccccaca | 300 |
| caaatgcaag ctcaccaagg tcccctctca gtccccttcc stacaccctg amcgccact | 360 |
| gscscacacc cacccagagc acgccacccg ccatggggar tgtgctcaag gartcgcngg | 420 |
| gcarcgtgga catctngtcc cagaaggggg cagaatctcc aatagangga ctgarcmstt | 480 |
| gctnanaaaa aaaaanaaaa aa | 502 |

<210> SEQ ID NO 196
<211> LENGTH: 665
<212> TYPE: DNA
<213> ORGANISM: Homo sapien
<220> FEATURE:
<221> NAME/KEY: misc_feature
<222> LOCATION: (1)...(665)
<223> OTHER INFORMATION: n = A,T,C or G

<400> SEQUENCE: 196

| | |
|---|---|
| ggttacttgg tttcattgcc accacttagt ggatgtcatt tagaaccatt ttgtctgctc | 60 |
| cctctggaag ccttgcgcag agcggactt gtaattgttg gagaataact gctgaatttt | 120 |
| wagctgtttk gagttgatts gcaccactgc acccacaact tcaatatgaa aacyawttga | 180 |
| actwatttat tatcttgtga aaagtataac aatgaaaatt ttgttcatac tgtattkatc | 240 |
| aagtatgatg aaaagcaawa gatatatatt cttttattat gttaaattat gattgccatt | 300 |
| attaatcggc aaaatgtgga gtgtatgttc ttttcacagt aatatatgcc ttttgtaact | 360 |
| tcacttggtt atttttattgt aaatgartta caaaattctt aatttaagar aatggtatgt | 420 |
| watatttatt tcattaattt ctttcctkgt ttacgtwaat tttgaaaaga wtgcatgatt | 480 |
| tcttgacaga aatcgatctt gatgctgtgg aagtagtttg acccacatcc ctatgagttt | 540 |
| ttcttagaat gtataaaggt tgtagcccat cnaacttcaa agaaaaaaat gaccacatac | 600 |
| tttgcaatca ggctgaaatg tggcatgctn ttctaattcc aactttataa actagcaaan | 660 |
| aagtg | 665 |

<210> SEQ ID NO 197
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 197

```
ttttnttttt tttttttttgc aggaaggatt ccatttattg tggatgcatt ttcacaatat      60
atgtttattg gagcgatcca ttatcagtga aaagtatcaa gtgtttataa nattttaggg     120
aaggcagatt cacagaacat gctngtcngc ttgcagtttt acctcgtana gatnacagag     180
aattatagtc naaccagtaa acnaggaatt tacttttcaa aagattaaat ccaaactgaa     240
caaaattcta ccctgaaact tactccatcc aaatattgga ataanagtca gcagtgatac     300
attctcttct gaactttaga ttttctagaa aaatatgtaa tagtgatcag gaaagagctct    360
tgttcaaaag tacaacnaag caatgttccc ttaccatagg ccttaattca aactttgatc     420
catttcactc ccatcacggg agtcaatgct acctgggaca cttgtatttt gttcatnctg     480
ancntggctt aa                                                         492
```

<210> SEQ ID NO 198
<211> LENGTH: 478
<212> TYPE: DNA
<213> ORGANISM: Homo sapien
<220> FEATURE:
<221> NAME/KEY: misc_feature
<222> LOCATION: (1)...(478)
<223> OTHER INFORMATION: n = A,T,C or G

<400> SEQUENCE: 198

```
tttnttttgn atttcantct gtannaanta ttttcattat gtttattana aaaatatnaa      60
tgtntccacn acaaatcatn ttacntnagt aagaggccan ctacattgta caacatacac     120
tgagtatatt ttgaaaagga caagtttaaa gtanacncat attgccganc atancacatt     180
tatacatggc ttgattgata tttagcacag canaaactga gtgagttacc agaaanaaat     240
natatatgtc aatcngattt aagatacaaa acagatccta tggtacatan catcngtag      300
gagttgtggc tttatgttta ctgaaagtca atgcagttcc tgtacaaaga gatggccgta     360
agcattctag tacctctact ccatggttaa gaatcgtaca cttatgttta catatgtnca     420
gggtaagaat tgtgttaagt naanttatgg agaggtccan gagaaaaatt tgatncaa       478
```

<210> SEQ ID NO 199
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 199

```
agtgacttgt cctccaacaa aacccccttga tcaagtttgt ggcactgaca atcagaccta     60
tgctagttcc tgtcatctat tcgctactaa atgcagactg gaggggacca aaaagggggca    120
tcaactccag ctggattatt ttggagcctg caaatctatt cctacttgta cggactttga    180
agtgattcag tttcctctac ggatgagaga ctggctcaag aatatcctca tgcagcttta    240
tgaagccnac tctgaacacg ctggttatct nagatgagaa ncagagaaat aaagtcnaga    300
aaatttacct ggangaaaag aggctttngg ctggggacca tcccattgaa ccttctctta    360
anggacttta agaanaaact accacatgtn tgtngtatcc tggtgccngg ccgtttantg    420
aacntngacn ncacccttnt ggaatananat cttgacngcn tcctgaactt gctcctctgc    480
ga                                                                    482
```

<210> SEQ ID NO 200
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 200

| | | | | |
|---|---|---|---|---|
| cggccgcaag tgcaactcca | gctggggccg | tgcggacgaa | gattctgcca | gcagttggtc | 60 |
| cgactgcgac gacggcggcg | gcgacagtcg | caggtgcagc | gcgggcgcct | ggggtcttgc | 120 |
| aaggctgagc tgacgccgca | gaggtcgtgt | cacgtccac | gaccttgacg | ccgtcgggga | 180 |
| cagccggaac agagcccggt | gaangcggga | ggcctcgggg | agccctcgg | gaagggcggc | 240 |
| ccgagagata cgcaggtgca | ggtggccgcc | | | | 270 |

<210> SEQ ID NO 201
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 201

| | | | | | |
|---|---|---|---|---|---|
| tttttttttt ttttggaatc | tactgcgagc | acagcaggtc | agcaacaagt | ttattttgca | 60 |
| gctagcaagg taacagggta | gggcatggtt | acatgttcag | gtcaacttcc | tttgtcgtgg | 120 |
| ttgattggtt tgtctttatg | ggggcggggt | ggggtagggg | aaancgaagc | anaantaaca | 180 |
| tggagtgggt gcaccctccc | tgtagaacct | ggttacnaaa | gcttggggca | gttcacctgg | 240 |
| tctgtgaccg tcattttctt | gacatcaatg | ttattagaag | tcaggatatc | ttttagagag | 300 |
| tccactgtnt ctggagggag | attagggttt | cttgccaana | tccaancaaa | atccacntga | 360 |
| aaaagttgga tgatncangt | acngaatacc | ganggcatan | ttctcatant | cggtggcca | 419 |

<210> SEQ ID NO 202
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 202

| | | | | | |
|---|---|---|---|---|---|
| tttnttttt ttttttttt | tttttttttt | tttttttttt | tttttttttt | tttttttttt | 60 |
| tggcacttaa tccatttta | tttcaaaatg | tctacaaant | ttnaatncnc | cattatacng | 120 |
| gtnattttnc aaaatctaaa | nnttattcaa | atntnagcca | aantccttac | ncaaatnnaa | 180 |
| tacncncaaa aatcaaaaat | atacntntct | ttcagcaaac | ttngttacat | aaattaaaaa | 240 |
| aatatatacg gctggtgttt | tcaaagtaca | attatcttaa | cactgcaaac | atntttnnaa | 300 |
| ggaactaaaa taaaaaaaaa | cactnccgca | aaggttaaag | ggaacaacaa | attcntttta | 360 |
| caacancnnc nattataaaa | atcatatctc | aaatcttagg | ggaatatata | cttcacacng | 420 |
| ggatcttaac ttttactnca | ctttgtttat | tttttanaa | ccattgtntt | gggcccaaca | 480 |
| caatggnaat nccnccncnc | tggactagt | | | | 509 |

```
<210> SEQ ID NO 203
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 203 ttttttttttt tttttttga ccccctctt ataaaaaaca agttaccatt ttattttact      60
tacacatatt tattttataa ttggtattag atattcaaaa ggcagttttt aaaatcaaac    120
taaatggaaa ctgccttaga tacataattc ttaggaatta gcttaaaatc tgcctaaagt    180
gaaaatcttc tctagctctt ttgactgtaa attttgact cttgtaaaac atccaaattc    240 attttcttg tctttaaaat tatctaatct ttccatttttt tccctattcc aagtcaattt    300
gcttctctag cctcatttcc tagctcttat ctactattag taagtggctt ttttcctaaa    360
agggaaaaca ggaagagana atggcacaca aaacaaacat tttatattca tatttctacc    420
tacgttaata aaatagcatt ttgtgaagcc agctcaaaag aaggcttaga tcctttttatg   480 tccatttttag tcactaaacg atatcnaaag tgccagaatg caaaaggttt gtgaacattt    540
attcaaaagc taatataaga tatttcacat actcatcttt ctg                      583

<210> SEQ ID NO 204
<211> LENGTH: 589
<212> TYPE: DNA
<213> ORGANISM: Homo sapien
<220> FEATURE:
<221> NAME/KEY: misc_feature
<222> LOCATION: (1)...(589)
<223> OTHER INFORMATION: n = A,T,C or G

<400> SEQUENCE: 204 tttttttttnt tttttttttt tttttttnctc ttctttttttt ttganaatga ggatcgagtt    60
tttcactctc tagatagggc atgaagaaaa ctcatctttc cagctttaaa ataacaatca    120
aatctcttat gctatatcat attttaagtt aaactaatga gtcactggct tatcttctcc    180
tgaaggaaat ctgttcattc ttctcattca tatagttata tcaagtacta ccttgcatat    240
tgagaggttt ttcttctcta tttacacata tatttccatg tgaatttgta tcaaaccttt    300
attttcatgc aaactagaaa ataatgtntt cttttgcata agagaagaga acaatatnag    360
cattacaaaa ctgctcaaat tgtttgttaa gnttatccat tataattagt tnggcaggag    420
ctaatacaaa tcacatttac ngacnagcaa taataaaact gaagtaccag ttaaatatcc    480
aaaataatta aaggaacatt tttagcctgg gtataattag ctaattcact ttacaagcat    540
ttattnagaa tgaattcaca tgttattatt ccntagccca acacaatgg                589

<210> SEQ ID NO 205
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 205
tttttntttt tttttcagt aataatcaga acaatattta ttttatatt taaaattcat       60 agaaaagtgc cttacattta ataaaagttt gtttctcaaa gtgatcagag gaattagata    120
```

```
tngtcttgaa caccaatatt aatttgagga aaatacacca aaatacatta agtaaattat      180
ttaagatcat agagcttgta agtgaaaaga taaaatttga cctcagaaac tctgagcatt      240
aaaaatccac tattagcaaa taaattacta tggacttctt gctttaattt tgtgatgaat      300
atggggtgtc actggtaaac caacacattc tgaaggatac attacttagt gatagattct      360
tatgtacttt gctanatnac gtggatatga gttgacaagt ttctctttct tcaatctttt      420
aaggggcnga ngaaatgagg aagaaaagaa aaggattacg catactgttc tttctatngg      480
aaggattaga tatgtttcct ttgccaatat taaaaaaata ataatgttta ctactagtga      540
aaccc                                                                  545

<210> SEQ ID NO 206
<211> LENGTH: 487
<212> TYPE: DNA
<213> ORGANISM: Homo sapien
<220> FEATURE:
<221> NAME/KEY: misc_feature
<222> LOCATION: (1)...(487)
<223> OTHER INFORMATION: n = A,T,C or G

<400> SEQUENCE: 206 ttttttttt tttttagtc aagtttctna tttttattat aattaaagtc ttggtcattt       60
catttattag ctctgcaact tacatattta aattaaagaa acgttnttag acaactgtna    120
caatttataa atgtaaggtg ccattattga gtanatatat tcctccaaga gtggatgtgt    180
cccttctccc accaactaat gaancagcaa cattagttta attttattag tagatnatac    240
actgctgcaa acgctaattc tcttctccat ccccatgtng atattgtgta tatgtgtgag    300
ttggtnagaa tgcatcanca atctnacaat caacagcaag atgaagctag gcntgggctt    360
tcggtgaaaa tagactgtgt ctgtctgaat caaatgatct gacctatcct cggtggcaag    420
aactcttcga accgcttcct caaaggcngc tgccacattt gtggcntctn ttgcacttgt    480
ttcaaaa                                                              487

<210> SEQ ID NO 207
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 207
tgaattggct aaaagactgc attttttanaa ctagcaactc ttatttcttt cctttaaaaa     60
tacatagcat taaatcccaa atcctattta aagacctgac agcttgagaa ggtcactact    120
gcatttatag gaccttctgg tggttctgct gttacntttg aantctgaca atccttgana    180
atctttgcat gcagaggagg taaaaggtat tggattttca cagaggaana acacagcgca    240
gaaatgaagg ggccaggctt actgagcttg tccactggag ggctcatggg tgggacatgg    300
aaaagaaggc agcctaggcc ctggggagcc ca                                  332

<210> SEQ ID NO 208
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G
```

<400> SEQUENCE: 208

```
agggcgtggt gcggagggcg ttactgtttt gtctcagtaa caataaatac aaaaagactg      60
gttgtgttcc ggccccatcc aaccacgaag ttgatttctc ttgtgtgcag agtgactgat     120
tttaaaggac atggagcttg tcacaatgtc acaatgtcac agtgtgaagg gcacactcac     180
tcccgcgtga ttcacattta gcaaccaaca atagctcatg agtccatact tgtaaatact     240
tttggcagaa tacttnttga aacttgcaga tgataactaa gatccaagat atttcccaaa     300
gtaaatagaa gtgggtcata atattaatta cctgttcaca tcagcttcca tttacaagtc     360
atgagcccag acactgacat caaactaagc ccacttagac tcctcaccac cagtctgtcc     420
tgtcatcaga caggaggctg tcaccttgac caaattctca ccagtcaatc atctatccaa     480
aaaccattac ctgatccact tccggtaatg caccaccttg gtga                     524
```

<210> SEQ ID NO 209
<211> LENGTH: 159
<212> TYPE: DNA
<213> ORGANISM: Homo sapien

<400> SEQUENCE: 209

```
gggtgaggaa atccagagtt gccatggaga aaattccagt gtcagcattc ttgctccttg      60
tggccctctc ctacactctg gccagagata ccacagtcaa acctggagcc aaaaaggaca     120
caaaggactc tcgacccaaa ctgccccaga ccctctcca                            159
```

<210> SEQ ID NO 210
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 210

```
actccctggc agacaaaggc agaggagaga gctctgttag ttctgtgttg ttgaactgcc      60
actgaatttc tttccacttg gactattaca tgccanttga gggactaatg gaaaaacgta     120
tgggagatt ttanccaatt tangtntgta aatgggggaga ctggggcagg cgggagagat     180
ttgcagggtg naaatgggan ggctggtttg ttanatgaac agggacatag gaggtaggca     240
ccaggatgct aaatca                                                     256
```

<210> SEQ ID NO 211
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 211

```
acattgtttt tttgagataa agcattgaga gagctctcct taacgtgaca caatggaagg      60
actggaacac atacccacat ctttgttctg agggataatt ttctgataaa gtcttgctgt     120
atattcaagc acatatgtta tatattattc agttccatgt ttatagccta gttaaggaga     180
ggggagatac attcngaaag aggactgaaa gaaatactca agtnggaaaa cagaaaaaga     240
aaaaaggag caaatgagaa gcct                                             264
```

<210> SEQ ID NO 212
<211> LENGTH: 328
<212> TYPE: DNA
<213> ORGANISM: Homo sapien
<220> FEATURE:
<221> NAME/KEY: misc_feature
<222> LOCATION: (1)...(328)
<223> OTHER INFORMATION: n = A,T,C or G

<400> SEQUENCE: 212

```
acccaaaaat ccaatgctga atatttggct tcattattcc canattctttt gattgtcaaa      60
ggatttaatg ttgtctcagc ttgggcactt cagttaggac ctaaggatgc cagccggcag     120
gtttatatat gcagcaacaa tattcaagcg cgacaacagg ttattgaact tgcccgccag     180
ttnaatttca ttcccattga cttgggatcc ttatcatcag ccagagagat tgaaaattta     240
ccccctacnac tctttactct ctgganaggg ccagtggtgg tagctataag cttggccaca     300
tttttttttc ctttattcct ttgtcaga                                         328
```

<210> SEQ ID NO 213
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 213

```
acttatgagc agagcgacat atccnagtgt agactgaata aaactgaatt ctctccagtt       60
taaagcattg ctcactgaag ggatagaagt gactgccagg agggaaagta agccaaggct     120
cattatgcca agganatat acatttcaat tctccaaact tcttcctcat tccaagagtt      180
ttcaatattt gcatgaacct gctgataanc catgttaana aacaaatatc tctctnacct     240
tctcatcggt                                                             250
```

<210> SEQ ID NO 214
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 214

```
acccagaatc caatgctgaa tatttggctt cattattccc agattctttg attgtcaaag      60
gatttaatgt tgtctcagct tgggcacttc agttaggacc taaggatgcc agccggcagg     120
tttatatatg cagcaacaat attcaagcgc gacaacaggt tattgaactt gcccgccagt     180
tgaatttcat tcccattgac ttgggatcct tatcatcagc canagagatt gaaaatttac     240
ccctacgact ctttactctc tggagagggc cagtggtggt agctataagc ttggccacat     300
tttttttttcc tttattcctt tgtcagagat gcgattcatc catatgctan aaaccaacag     360
agtgactttt acaaaattcc tataganatt gtgaataaaa ccttacctat agttgccatt     420
actttgctct ccctaatata cctc                                             444
```

<210> SEQ ID NO 215
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 215

| | | |
|---|---|---|
| acttatgagc agagcgacat atccaagtgt anactgaata aaactgaatt ctctccagtt | 60 |
| taaagcattg ctcactgaag ggatagaagt gactgccagg agggaaagta agccaaggct | 120 |
| cattatgcca aagganatat acatttcaat tctccaaact tcttcctcat tccaagagtt | 180 |
| ttcaatattt gcatgaacct gctgataagc catgttgaga aacaaatatc tctctgacct | 240 |
| tctcatcggt aagcagaggc tgtaggcaac atggaccata gcgaanaaaa aacttagtaa | 300 |
| tccaagctgt tttctacact gtaaccaggt ttccaaccaa ggtggaaatc tcctatactt | 360 |
| ggtgcc | 366 |

<210> SEQ ID NO 216
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

<400> SEQUENCE: 216

| | | |
|---|---|---|
| ctgtataaac agaactccac tgcangaggg agggccgggc caggagaatc tccgcttgtc | 60 |
| caagacaggg gcctaaggag ggtctccaca ctgctnntaa gggctnttnc atttttttat | 120 |
| taataaaaag tnnaaaaggc ctcttctcaa cttttttccc ttnggctgga aaatttaaaa | 180 |
| atcaaaaatt tcctnaagtt ntcaagctat catatatact ntatcctgaa aaagcaacat | 240 |
| aattcttcct tccctccttt | 260 |

<210> SEQ ID NO 217
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 217

| | | |
|---|---|---|
| acctacgtgg gtaagtttan aaatgttata atttcaggaa naggaacgca tataattgta | 60 |
| tcttgcctat aattttctat tttaataagg aaatagcaaa ttggggtggg gggaatgtag | 120 |
| ggcattctac agtttgagca aaatgcaatt aaatgtggaa ggacagcact gaaaaatttt | 180 |
| atgaataatc tgtatgatta tatgtctcta gagtagattt ataattagcc acttacccta | 240 |
| atatccttca tgcttgtaaa gt | 262 |

<210> SEQ ID NO 218
<211> LENGTH: 205
<212> TYPE: DNA
<213> ORGANISM: Homo sapien
<220> FEATURE:
<221> NAME/KEY: misc_feature
<222> LOCATION: (1)...(205)
<223> OTHER INFORMATION: n = A,T,C or G

<400> SEQUENCE: 218

| | | |
|---|---|---|
| accaaggtgg tgcattaccg gaantggatc aangacacca tcgtggccaa cccctgagca | 60 |

-continued

```
cccctatcaa ctcccttttg tagtaaactt ggaaccttgg aaatgaccag gccaagactc      120
aggcctcccc agttctactg acctttgtcc ttangtntna ngtccagggt tgctaggaaa      180
anaaatcagc agacacaggt gtaaa                                            205
```

<210> SEQ ID NO 219
<211> LENGTH: 114
<212> TYPE: DNA
<213> ORGANISM: Homo sapien

<400> SEQUENCE: 219

```
tactgttttg tctcagtaac aataaataca aaagactgg ttgtgttccg gccccatcca       60
accacgaagt tgatttctct tgtgtgcaga gtgactgatt ttaaaggaca tgga            114
```

<210> SEQ ID NO 220
<211> LENGTH: 93
<212> TYPE: DNA
<213> ORGANISM: Homo sapien

<400> SEQUENCE: 220

```
actagccagc acaaaaggca gggtagcctg aattgctttc tgctctttac atttctttta     60
aaataagcat ttagtgctca gtccctactg agt                                   93
```

<210> SEQ ID NO 221
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 221

```
actangtgca ggtgcgcaca aatatttgtc gatattccct tcatcttgga ttccatgagg     60
tcttttgccc agcctgtggc tctactgtag taagtttctg ctgatgagga gccagnatgc    120
cccccactac cttccctgac gctccccana aatcacccaa cctctgt                   167
```

<210> SEQ ID NO 222
<211> LENGTH: 351
<212> TYPE: DNA
<213> ORGANISM: Homo sapien

<400> SEQUENCE: 222

```
agggcgtggt gcggagggcg gtactgacct cattagtagg aggatgcatt ctggcacccc     60
gttcttcacc tgtcccccaa tccttaaaag gccatactgc ataaagtcaa caacagataa    120
atgtttgctg aattaaagga tggatgaaaa aaattaataa tgaattttg cataatccaa     180 ttttctcttt tatatttcta gaagaagttt ctttgagcct attagatccc gggaatcttt    240
taggtgagca tgattagaga gcttgtaggt tgcttttaca tatatctggc atatttgagt    300
ctcgtatcaa acaatagat tggtaaaggt ggtattattg tattgataag t               351
```

<210> SEQ ID NO 223
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 223

```
aaaacaaaca aacaaaaaaa acaattcttc attcagaaaa attatcttag ggactgatat      60
tggtaattat ggtcaattta atwrtrttkt ggggcatttc cttacattgt cttgacaaga     120
ttaaaatgtc tgtgccaaaa ttttgtattt tatttggaga cttcttatca aaagtaatgc     180
tgccaaagga agtctaagga attagtagtg ttcccmtcac ttgtttggag tgtgctattc     240
taaaagattt tgatttcctg gaatgacaat tatattttaa ctttggtggg ggaaanagtt     300
ataggaccac agtcttcact tctgatactt gtaaattaat cttttattgc acttgttttg     360
accattaagc tatatgttta aaa                                              383

<210> SEQ ID NO 224
<211> LENGTH: 320
<212> TYPE: DNA
<213> ORGANISM: Homo sapien

<400> SEQUENCE: 224
cccctgaagg cttcttgtta gaaatagta cagttacaac caataggaac aacaaaaaga      60 aaagtttgt gacattgtag tagggagtgt gtacccctta ctccccatca aaaaaaaaat     120
ggatacatgg ttaaaggata raagggcaat attttatcat atgttctaaa agagaaggaa    180
gagaaaatac tactttctcr aaatggaagc ccttaaaggt gctttgatac tgaaggacac    240
aaatgtggcc gtccatcctc ctttaragtt gcatgacttg gacacggtaa ctgttgcagt    300
tttaractcm gcattgtgac                                                 320

<210> SEQ ID NO 225
<211> LENGTH: 1214
<212> TYPE: DNA
<213> ORGANISM: Homo sapien

<400> SEQUENCE: 225
gaggactgca gcccgcactc gcagccctgg caggcggcac tggtcatgga aaacgaattg      60
ttctgctcgg gcgtcctggt gcatccgcag tgggtgctgt cagccgcaca ctgtttccag     120
aactcctaca ccatcgggct gggcctgcac agtcttgagg ccgaccaaga gccagggagc     180
cagatggtgg aggccagcct ctccgtacga cacccagagt acaacagacc cttgctcgct     240
aacgacctca tgctcatcaa gttggacgaa tccgtgtccg agtctgacac catccggagc     300
atcagcattg cttcgcagtg ccctaccgcg gggaactctt gcctcgtttc tggctggggt     360
ctgctggcga acggcagaat gcctaccgtg ctgcagtgcg tgaacgtgtc ggtggtgtct     420
gaggaggtct gcagtaagct ctatgacccg ctgtaccacc ccagcatgtt ctgcgccggc    480
ggagggcaag accagaagga ctcctgcaac ggtgactctg ggggccccct gatctgcaac     540
gggtacttgc agggccttgt gtctttcgga aaagcccgt gtggccaagt tggcgtgcca      600
ggtgtctaca ccaacctctg caaattcact gagtggatag agaaaaccgt ccaggccagt    660
taactctggg gactgggaac ccatgaaatt gacccccaaa tacatcctgc ggaaggaatt    720
caggaatatc tgttcccagc ccctcctccc tcaggcccag gagtccaggc ccccagcccc    780
tcctccctca aaccaagggt acagatcccc agcccctcct ccctcagacc caggagtcca    840
gaccccccag cccctcctcc ctcagaccca ggagtccagc cctcctcccc tcagacccag    900
gagtccagac cccccagccc ctcctccctc agacccaggg gtccaggccc caacccctc     960 ctccctcaga ctcagaggtc caagccccca acccctcctt cccagacccc agaggtccag    1020
gtcccagccc ctcctccctc agacccagcg gtccaatgcc acctagactc tccctgtaca    1080
```

-continued

```
cagtgccccc ttgtggcacg ttgacccaac cttaccagtt ggttttttcat tttttgtccc    1140 tttcccctag atccagaaat aaagtctaag agaagcgcaa aaaaaaaaaa aaaaaaaaaa    1200
aaaaaaaaaa aaaa                                                      1214
```

<210> SEQ ID NO 226
<211> LENGTH: 119
<212> TYPE: DNA
<213> ORGANISM: Homo sapien

<400> SEQUENCE: 226

```
acccagtatg tgcagggaga cggaaccccca tgtgacagcc cactccacca gggttcccaa      60
agaacctggc ccagtcataa tcattcatcc tgacagtggc aataatcacg ataaccagt      119
```

<210> SEQ ID NO 227
<211> LENGTH: 818
<212> TYPE: DNA
<213> ORGANISM: Homo sapien

<400> SEQUENCE: 227

```
acaattcata gggacgacca atgaggacag ggaatgaacc cggctctccc ccagccctga       60
tttttgctac atatggggtc ccttttcatt ctttgcaaaa acactgggtt ttctgagaac     120
acggacggtt cttagcacaa tttgtgaaat ctgtgtaraa ccgggctttg cagggagat      180 aattttcctc ctctggagga aaggtggtga ttgacaggca gggagacagt gacaaggcta     240
gagaaagcca cgctcggcct tctctgaacc aggatgaac ggcagacccc tgaaaacgaa      300
gcttgtcccc ttccaatcag ccacttctga gaacccccat ctaacttcct actggaaaag    360
agggcctcct caggagcagt ccaagagttt tcaaagataa cgtgacaact accatctaga    420
ggaaagggtg caccctcagc agagaagccg agagcttaac tctggtcgtt tccagagaca     480
acctgctggc tgtcttggga tgcgcccagc ctttgagagg ccactacccc atgaacttct    540
gccatccact ggacatgaag ctgaggacac tgggcttcaa cactgagttg tcatgagagg    600
gacaggctct gccctcaagc cggctgaggg cagcaaccac tctcctcccc tttctcacgc     660
aaagccattc ccacaaatcc agaccatacc atgaagcaac gagacccaaa cagtttggct    720
caagaggata tgaggactgt ctcagcctgg ctttgggctg acaccatgca cacacacaag    780
gtccacttct aggttttcag cctagatggg agtcgtgt                             818
```

<210> SEQ ID NO 228
<211> LENGTH: 744
<212> TYPE: DNA
<213> ORGANISM: Homo sapien

<400> SEQUENCE: 228

```
actggagaca ctgttgaact tgatcaagac ccagaccacc ccaggtctcc ttcgtgggat      60
gtcatgacgt ttgacatacc tttggaacga gcctcctcct tggaagatgg aagaccgtgt    120
tcgtggccga cctggcctct cctggcctgt ttcttaagat gcggagtcac atttcaatgg    180
taggaaaagt ggcttcgtaa aatagaagag cagtcactgt ggaactacca aatggcgaga    240
tgctcggtgc acattgggt gctttgggat aaaagattta tgagccaact attctctggc    300
accagattct aggccagttt gttccactga agcttttccc acagcagtcc acctctgcag    360
gctggcagct gaatgcttg ccggtggctc tgtggcaaga tcacactgag atcgatgggt    420
gagaaggcta ggatgcttgt ctagtgttct tagctgtcac gttggctcct tccaggttgg    480
ccagacggtg ttggccactc ccttctaaaa cacaggcgcc ctcctggtga cagtgacccg    540
```

```
ccgtggtatg ccttggccca ttccagcagt cccagttatg catttcaagt ttggggtttg    600
ttcttttcgt taatgttcct ctgtgttgtc agctgtcttc atttcctggg ctaagcagca    660
ttgggagatg tggaccagag atccactcct taagaaccag tggcgaaaga cactttcttt    720
cttcactctg aagtagctgg tggt                                            744
```

<210> SEQ ID NO 229
<211> LENGTH: 300
<212> TYPE: DNA
<213> ORGANISM: Homo sapien

<400> SEQUENCE: 229

```
cgagtctggg ttttgtctat aaagtttgat ccctcctttt ctcatccaaa tcatgtgaac     60
cattacacat cgaaataaaa gaaggtggc agacttgccc aacgccaggc tgacatgtgc    120 tgcaggttg ttgttttta attattattg ttagaaacgt cacccacagt ccctgttaat    180
ttgtatgtga cagccaactc tgagaaggtc ctattttttcc acctgcagag gatccagtct    240
cactaggctc ctccttgccc tcacactgga gtctccgcca gtgtgggtgc ccactgacat    300
```

<210> SEQ ID NO 230
<211> LENGTH: 301
<212> TYPE: DNA
<213> ORGANISM: Homo sapien

<400> SEQUENCE: 230

```
cagcagaaca aatacaaata tgaagagtgc aaagatctca taaaatctat gctgaggaat     60
gagcgacagt tcaaggagga gaagcttgca gagcagctca agcaagctga ggagctcagg    120
caatataaag tcctggttca cactcaggaa cgagagctga cccagttaag ggagaagttg    180
cgggaaggga gagatgcctc cctctcattg aatgagcatc tccaggccct cctcactccg    240
gatgaaccgg acaagtccca ggggcaggac ctccaagaaa cagacctcgg ccgcgaccac    300
g                                                                     301
```

<210> SEQ ID NO 231
<211> LENGTH: 301
<212> TYPE: DNA
<213> ORGANISM: Homo sapien

<400> SEQUENCE: 231

```
gcaagcacgc tggcaaatct ctgtcaggtc agctccagag aagccattag tcattttagc     60
caggaactcc aagtccacat ccttggcaac tggggacttg cgcaggttag ccttgaggat    120
ggcaacacgg gacttctcat caggaagtgg gatgtagatg agctgatcaa gacggccagg    180
tctgaggatg gcaggatcaa tgatgtcagg ccggttggta ccgccaatga tgaacacatt    240 ttttttgtg gacatgccat ccatttctgt caggatctgg ttgatgactc ggtcagcagc    300
c                                                                     301
```

<210> SEQ ID NO 232
<211> LENGTH: 301
<212> TYPE: DNA
<213> ORGANISM: Homo sapien

<400> SEQUENCE: 232

```
agtaggtatt tcgtgagaag ttcaacacca aaactggaac atagttctcc ttcaagtgtt     60
ggcgacagcg gggcttcctg attctggaat ataactttgt gtaaattaac agccacctat    120
```

| | |
|---|---|
| agaagagtcc atctgctgtg aaggagagac agagaactct gggttccgtc gtcctgtcca | 180 |
| cgtgctgtac caagtgctgg tgccagcctg ttacctgttc tcactgaaaa tctggctaat | 240 |
| gctcttgtgt atcacttctg attctgacaa tcaatcaatc aatggcctag agcactgact | 300 |
| g | 301 |

<210> SEQ ID NO 233
<211> LENGTH: 301
<212> TYPE: DNA
<213> ORGANISM: Homo sapien

<400> SEQUENCE: 233

| | |
|---|---|
| atgactgact tcccagtaag gctctctaag gggtaagtag gaggatccac aggatttgag | 60 |
| atgctaaggc cccagagatc gtttgatcca accctcttat tttcagaggg gaaaatgggg | 120 |
| cctagaagtt acagagcatc tagctggtgc gctggcaccc ctggcctcac acagactccc | 180 |
| gagtagctgg gactacaggc acacagtcac tgaagcaggc cctgttagca attctatgcg | 240 |
| tacaaattaa catgagatga gtagagactt tattgagaaa gcaagagaaa atcctatcaa | 300 |
| c | 301 |

<210> SEQ ID NO 234
<211> LENGTH: 301
<212> TYPE: DNA
<213> ORGANISM: Homo sapien

<400> SEQUENCE: 234

| | |
|---|---|
| aggtcctaca catcgagact catccatgat tgatatgaat ttaaaaatta caagcaaaga | 60 |
| cattttattc atcatgatgc tttcttttgt ttcttctttt cgttttcttc tttttctttt | 120 |
| tcaatttcag caacatactt ctcaatttct tcaggattta aaatcttgag ggattgatct | 180 |
| cgcctcatga cagcaagttc aatgttttg ccacctgact gaaccacttc caggagtgcc | 240 |
| ttgatcacca gcttaatggt cagatcatct gcttcaatgg cttcgtcagt atagttcttc | 300 |
| t | 301 |

<210> SEQ ID NO 235
<211> LENGTH: 283
<212> TYPE: DNA
<213> ORGANISM: Homo sapien

<400> SEQUENCE: 235

| | |
|---|---|
| tggggctgtg catcaggcgg gtttgagaaa tattcaattc tcagcagaag ccagaatttg | 60 |
| aattccctca tcttttaggg aatcatttac caggtttgga gaggattcag acagctcagg | 120 |
| tgctttcact aatgtctctg aacttctgtc cctctttgtt catggatagt ccaataaata | 180 |
| atgttatctt tgaactgatg ctcataggag agaatataag aactctgagt gatatcaaca | 240 |
| ttagggattc aaagaaatat tagatttaag ctcacactgg tca | 283 |

<210> SEQ ID NO 236
<211> LENGTH: 301
<212> TYPE: DNA
<213> ORGANISM: Homo sapien

<400> SEQUENCE: 236

| | |
|---|---|
| aggtcctcca ccaactgcct gaagcacggt taaaattggg aagaagtata gtgcagcata | 60 |
| aatacttta aatcgatcag atttccctaa cccacatgca atcttcttca ccagaagagg | 120 |
| tcggagcagc atcattaata ccaagcagaa tgcgtaatag ataaatacaa tggtatatag | 180 |

```
tgggtagacg gcttcatgag tacagtgtac tgtggtatcg taatctggac ttgggttgta      240
aagcatcgtg taccagtcag aaagcatcaa tactcgacat gaacgaatat aaagaacacc      300
a                                                                      301
```

```
<210> SEQ ID NO 237
<211> LENGTH: 301
<212> TYPE: DNA
<213> ORGANISM: Homo sapien

<400> SEQUENCE: 237
cagtggtagt ggtggtggac gtggcgttgg tcgtggtgcc ttttttggtg cccgtcacaa       60
actcaatttt tgttcgctcc tttttggcct tttccaattt gtccatctca attttctggg      120
ccttggctaa tgcctcatag taggagtcct cagaccagcc atgggatca aacatatcct       180 ttgggtagtt ggtgccaagc tcgtcaatgg cacagaatgg atcagcttct cgtaaatcta      240
gggttccgaa attctttctt cctttggata atgtagttca tatccattcc ctcctttatc      300
t                                                                      301
```

```
<210> SEQ ID NO 238
<211> LENGTH: 301
<212> TYPE: DNA
<213> ORGANISM: Homo sapien

<400> SEQUENCE: 238
gggcaggttt ttttttttttt tttttgatg gtgcagaccc ttgctttatt tgtctgactt       60
gttcacagtt cagcccctg ctcagaaaac caacgggcca gctaaggaga ggaggaggca      120
ccttgagact tccggagtcg aggctctcca gggttcccca gcccatcaat catttctgc      180 accccctgcc tgggaagcag ctccctgggg ggtgggaatg ggtgactaga agggatttca     240
gtgtgggacc cagggtctgt tcttcacagt aggaggtgga agggatgact aatttcttta      300
t                                                                      301
```

```
<210> SEQ ID NO 239
<211> LENGTH: 239
<212> TYPE: DNA
<213> ORGANISM: Homo sapien

<400> SEQUENCE: 239
ataagcagct agggaattct ttatttagta atgtcctaac ataaagttc acataactgc        60 ttctgtcaaa ccatgatact gagctttgtg acaacccaga aataactaag agaaggcaaa     120 cataataacct tagagatcaa gaaacattta cacagttcaa ctgttaaaaa atagctcaac    180
attcagccag tgagtagagt gtgaatgcca gcatacacag tatacaggtc cttcaggga      239
```

```
<210> SEQ ID NO 240
<211> LENGTH: 300
<212> TYPE: DNA
<213> ORGANISM: Homo sapien

<400> SEQUENCE: 240
ggtcctaatg aagcagcagc ttccacattt taacgcaggt ttacggtgat actgtccttt       60
gggatctgcc ctccagtgga acctttaag gaagaagtgg gcccaagcta agttccacat      120
gctgggtgag ccagatgact tctgttccct ggtcactttc ttcaatgggg cgaatggggg     180
ctgccaggtt tttaaaatca tgcttcatct tgaagcacac ggtcacttca ccctcctcac      240
```

-continued gctgtgggtg tactttgatg aaaatacccc ctttgttggc ctttctgaag ctataatgtc      300

<210> SEQ ID NO 241
<211> LENGTH: 301
<212> TYPE: DNA
<213> ORGANISM: Homo sapien

<400> SEQUENCE: 241
gaggtctggt gctgaggtct ctgggctagg aagaggagtt ctgtggagct ggaagccaga      60
cctctttgga ggaaactcca gcagctatgt tggtgtctct gagggaatgc aacaaggctg      120
ctcctccatg tattggaaaa ctgcaaactg gactcaactg gaaggaagtg ctgctgccag      180
tgtgaagaac cagcctgagg tgacagaaac ggaagcaaac aggaacagcc agtcttttct      240
tcctcctcct gtcatacggt ctctctcaag catcctttgt tgtcaggggc ctaaaaggga      300
g                                                                     301

<210> SEQ ID NO 242
<211> LENGTH: 301
<212> TYPE: DNA
<213> ORGANISM: Homo sapien

<400> SEQUENCE: 242
ccgaggtcct gggatgcaac caatcactct gtttcacgtg acttttatca ccatacaatt      60
tgtggcattt cctcattttc tacattgtag aatcaagagt gtaaataaat gtatatcgat      120
gtcttcaaga atatatcatt ccttttttcac tagaacccat tcaaaatata agtcaagaat      180
cttaatatca acaaatatat caagcaaact ggaaggcaga ataactacca taatttagta      240
taagtaccca aagttttata aatcaaaagc cctaatgata accattttta gaattcaatc      300
a                                                                     301

<210> SEQ ID NO 243
<211> LENGTH: 301
<212> TYPE: DNA
<213> ORGANISM: Homo sapien

<400> SEQUENCE: 243
aggtaagtcc cagtttgaag ctcaaaagat ctggtatgag cataggctca tcgacgacat      60
ggtggcccaa gctatgaaat cagagggagg cttcatctgg gcctgtaaaa actatgatgg      120
tgacgtgcag tcggactctg tggcccaagg gtatggctct ctcggcatga tgaccagcgt      180
gctggtttgt ccagatggca agacagtaga agcagaggct gcccacggga ctgtaacccg      240
tcactaccgc atgttccaga aggacagga gacgtccacc aatcccattg cttccatttt      300
t                                                                     301

<210> SEQ ID NO 244
<211> LENGTH: 300
<212> TYPE: DNA
<213> ORGANISM: Homo sapien

<400> SEQUENCE: 244
gctggtttgc aagaatgaaa tgaatgattc tacagctagg acttaacctt gaaatggaaa      60
gtcatgcaat cccatttgca ggatctgtct gtgcacatgc ctctgtagag agcagcattc      120
ccagggacct tggaaacagt tgacactgta aggtgcttgc tccccaagac acatcctaaa      180
aggtgttgta atggtgaaaa cgtcttcctt ctttattgcc ccttcttatt tatgtgaaca      240
actgtttgtc ttttgtgtat ctttttttaaa ctgtaaagtt caattgtgaa aatgaatatc      300

<210> SEQ ID NO 245
<211> LENGTH: 301
<212> TYPE: DNA
<213> ORGANISM: Homo sapien

<400> SEQUENCE: 245

```
gtctgagtat ttaaaatgtt attgaaatta tccccaacca atgttagaaa agaaagaggt      60
tatatactta gataaaaaat gaggtgaatt actatccatt gaaatcatgc tcttagaatt     120
aaggccagga gatattgtca ttaatgtara cttcaggaca ctagagtata gcagccctat     180
gttttcaaag agcagagatg caattaaata ttgtttagca tcaaaaggc cactcaatac      240
agctaataaa atgaaagacc taatttctaa agcaattctt tataatttac aaagttttaa     300
g                                                                    301
```

<210> SEQ ID NO 246
<211> LENGTH: 301
<212> TYPE: DNA
<213> ORGANISM: Homo sapien

<400> SEQUENCE: 246

```
ggtctgtcct acaatgcctg cttcttgaaa gaagtcggca ctttctagaa tagctaaata      60
acctgggctt attttaaaga actatttgta gctcagattg gttttcctat ggctaaaata     120
agtgcttctt gtgaaaatta ataaaaacag ttaattcaaa gccttgatat atgttaccac     180
taacaatcat actaaatata ttttgaagta caaagtttga catgctctaa agtgacaacc     240
caaatgtgtc ttacaaaaca cgttcctaac aaggtatgct ttacactacc aatgcagaaa     300
c                                                                    301
```

<210> SEQ ID NO 247
<211> LENGTH: 301
<212> TYPE: DNA
<213> ORGANISM: Homo sapien

<400> SEQUENCE: 247

```
aggtcctttg gcagggctca tggatcagag ctcaaactgg agggaaaggc atttcgggta      60
gcctaagagg gcgactggcg gcagcacaac caaggaaggc aaggttgttt ccccacgct      120
gtgtcctgtg ttcaggtgcg acacacaatc ctcatgggaa caggatcacc catgcgctgc    180
ccttgatgat caaggttggg gcttaagtgg attaaggag gcaagttctg ggttccttgc    240
cttttcaaac catgaagtca ggctctgtat ccctcctttt cctaactgat attctaacta    300
a                                                                    301
```

<210> SEQ ID NO 248
<211> LENGTH: 301
<212> TYPE: DNA
<213> ORGANISM: Homo sapien

<400> SEQUENCE: 248

```
aggtccttgg agatgccatt tcagccgaag gactcttctw ttcggaagta caccctcact      60
attaggaaga ttcttagggg taattttct gaggaaggag aactagccaa cttaagaatt     120
acaggaagaa agtggtttgg aagacagcca agaaataaa agcagattaa attgtatcag     180
gtacattcca gcctgttggc aactccataa aaacatttca gattttaatc ccgaatttag    240
ctaatgagac tggattttg tttttatgt tgtgtgtcgc agagctaaaa actcagttcc      300
```

<210> SEQ ID NO 249
<211> LENGTH: 301
<212> TYPE: DNA
<213> ORGANISM: Homo sapien

<400> SEQUENCE: 249

| | | | | | |
|---|---|---|---|---|---|
| gtccagagga | agcacctggt | gctgaactag | gcttgccctg | ctgtgaactt | gcacttggag | 60 |
| ccctgacgct | gctgttctcc | ccgaaaaacc | cgaccgacct | ccgcgatctc | cgtcccgccc | 120 |
| ccagggagac | acagcagtga | ctcagagctg | gtcgcacact | gtgcctccct | cctcaccgcc | 180 |
| catcgtaatg | aattattttg | aaaattaatt | ccaccatcct | ttcagattct | ggatggaaag | 240 |
| actgaatctt | tgactcagaa | ttgtttgctg | aaaagaatga | tgtgactttc | ttagtcattt | 300 |
| a | | | | | | 301 |

<210> SEQ ID NO 250
<211> LENGTH: 301
<212> TYPE: DNA
<213> ORGANISM: Homo sapien

<400> SEQUENCE: 250

| | | | | | |
|---|---|---|---|---|---|
| ggtctgtgac | aaggacttgc | aggctgtggg | aggcaagtga | cccttaacac | tacacttctc | 60 |
| cttatcttta | ttggcttgat | aaacataatt | atttctaaca | ctagcttatt | tccagttgcc | 120 |
| cataagcaca | tcagtacttt | tctctggctg | gaatagtaaa | ctaaagtatg | gtacatctac | 180 |
| ctaaaagact | actatgtgga | ataatacata | ctaatgaagt | attacatgat | ttaaagacta | 240 |
| caataaaacc | aaacatgctt | ataacattaa | gaaaacaat | aagatacat | gattgaaacc | 300 |
| a | | | | | | 301 |

<210> SEQ ID NO 251
<211> LENGTH: 301
<212> TYPE: DNA
<213> ORGANISM: Homo sapien

<400> SEQUENCE: 251

| | | | | | |
|---|---|---|---|---|---|
| gccgaggtcc | tacatttggc | ccagtttccc | cctgcatcct | ctccagggcc | cctgcctcat | 60 |
| agacaacctc | atagagcata | ggagaactgg | ttgccctggg | ggcaggggga | ctgtctggat | 120 |
| ggcagggtc | ctcaaaaatg | ccactgtcac | tgccaggaaa | tgcttctgag | cagtacacct | 180 |
| cattgggatc | aatgaaaagc | ttcaagaaat | cttcaggctc | actctcttga | aggcccggaa | 240 |
| cctctggagg | ggggcagtgg | aatcccagct | ccaggacgga | tcctgtcgaa | aagatatcct | 300 |
| c | | | | | | 301 |

<210> SEQ ID NO 252
<211> LENGTH: 301
<212> TYPE: DNA
<213> ORGANISM: Homo sapien

<400> SEQUENCE: 252

| | | | | | |
|---|---|---|---|---|---|
| gcaaccaatc | actctgtttc | acgtgacttt | tatcaccata | caatttgtgg | catttcctca | 60 |
| ttttctacat | tgtagaatca | agagtgtaaa | taaatgtata | tcgatgtctt | caagaatata | 120 |
| tcattccttt | ttcactagga | acccattcaa | aatataagtc | aagaatctta | atatcaacaa | 180 |
| atatatcaag | caaactggaa | ggcagaataa | ctaccataat | ttagtataag | tacccaaagt | 240 |
| tttataaatc | aaaagcccta | atgataacca | ttttagaat | tcaatcatca | ctgtagaatc | 300 |

| | |
|---|---|
| a | 301 |

<210> SEQ ID NO 253
<211> LENGTH: 301
<212> TYPE: DNA
<213> ORGANISM: Homo sapien

<400> SEQUENCE: 253

| | |
|---|---|
| ttccctaaga agatgttatt ttgttgggtt ttgttcccccc tccatctcga ttctcgtacc | 60 |
| caactaaaaa aaaaaaataa agaaaaaatg tgctgcgttc tgaaaaataa ctccttagct | 120 |
| tggtctgatt gttttcagac cttaaaatat aaacttgttt cacaagcttt aatccatgtg | 180 |
| gatttttttt cttagagaac cacaaaacat aaaaggagca agtcggactg aatacctgtt | 240 |
| tccatagtgc ccacagggta ttcctcacat tttctccata ggaaaatgct ttttcccaag | 300 |
| g | 301 |

<210> SEQ ID NO 254
<211> LENGTH: 301
<212> TYPE: DNA
<213> ORGANISM: Homo sapien

<400> SEQUENCE: 254

| | |
|---|---|
| cgctgcgcct ttcccttggg ggaggggcaa ggccagaggg ggtccaagtg cagcacgagg | 60 |
| aacttgacca attcccttga agcgggtggg ttaaaccctg taaatgggaa caaaatcccc | 120 |
| ccaaatctct tcatcttacc ctggtggact cctgactgta gaatttttttg gttgaaacaa | 180 |
| gaaaaaaata aagctttgga cttttcaagg ttgcttaaca ggtactgaaa gactggcctc | 240 |
| acttaaactg agccaggaaa agctgcagat ttattaatgg gtgtgttagt gtgcagtgcc | 300 |
| t | 301 |

<210> SEQ ID NO 255
<211> LENGTH: 302
<212> TYPE: DNA
<213> ORGANISM: Homo sapien

<400> SEQUENCE: 255

| | |
|---|---|
| agcttttttt tttttttttt ttttttttttt ttcattaaaa aatagtgctc tttattataa | 60 |
| attactgaaa tgtttctttt ctgaatataa atataaatat gtgcaaagtt tgacttggat | 120 |
| tgggattttg ttgagttctt caagcatctc ctaatacccct caagggcctg agtaggggggg | 180 |
| aggaaaaagg actggaggtg gaatctttat aaaaaacaag agtgattgag gcagattgta | 240 |
| aacattatta aaaacaaga aacaaacaaa aaatagaga aaaaaaccac cccaacacac | 300 |
| aa | 302 |

<210> SEQ ID NO 256
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 256

| | |
|---|---|
| gttccagaaa acattgaagg tggcttccca aagtctaact agggataccc cctctagcct | 60 |
| aggaccctcc tccccacacc tcaatccacc aaaccatcca taatgcaccc agataggccc | 120 |

-continued

| | |
|---|---|
| accccccaaaa gcctggacac cttgagcaca cagttatgac caggacagac tcatctctat | 180 |
| aggcaaatag ctgctggcaa actggcatta cctggtttgt ggggatgggg gggcaagtgt | 240 |
| gtggcctctc ggcctggtta gcaagaacat tcagggtagg cctaagttan tcgtgttagt | 300 |
| t | 301 |

<210> SEQ ID NO 257
<211> LENGTH: 301
<212> TYPE: DNA
<213> ORGANISM: Homo sapien

<400> SEQUENCE: 257

| | |
|---|---|
| gttgtggagg aactctggct tgctcattaa gtcctactga ttttcactat ccctgaatt | 60 |
| tccccactta tttttgtctt tcactatcgc aggccttaga agaggtctac ctgcctccag | 120 |
| tcttacctag tccagtctac ccctggagt tagaatggcc atcctgaagt gaaaagtaat | 180 |
| gtcacattac tcccttcagt gatttcttgt agaagtgcca atccctgaat gccaccaaga | 240 |
| tcttaatctt cacatcttta atcttatctc tttgactcct ctttacaccg gagaaggctc | 300 |
| c | 301 |

<210> SEQ ID NO 258
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 258

| | |
|---|---|
| cagcagtagt agatgccgta tgccagcacg cccagcactc ccaggatcag caccagcacc | 60 |
| aggggcccag ccaccaggcg cagaagcaag ataaacagta ggctcaagac cagagccacc | 120 |
| cccagggcaa caagaatcca ataccaggac tgggcaaaat cttcaaagat cttaacactg | 180 |
| atgtctcggg cattgaggct gtcaataana cgctgatccc ctgctgtatg gtggtgtcat | 240 |
| tggtgatccc tgggagcgcc ggtggagtaa cgttggtcca tggaaagcag cgcccacaac | 300 |
| t | 301 |

<210> SEQ ID NO 259
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 259

| | |
|---|---|
| tcatatatgc aaacaaatgc agactangcc tcaggcagag actaaaggac atctcttggg | 60 |
| gtgtcctgaa gtgatttgga cccctgaggg cagacaccta gtaggaatc ccagtgggaa | 120 |
| gcaaagccat aaggaagccc aggattcctt gtgatcagga agtgggccag gaaggtctgt | 180 |
| tccagctcac atctcatctg catgcagcac ggaccggatg cgcccactgg gtcttggctt | 240 |
| ccctcccatc ttctcaagca gtgtccttgt tgagccattt gcatccttgg ctccaggtgg | 300 |
| c | 301 |

<210> SEQ ID NO 260
<211> LENGTH: 301

<212> TYPE: DNA
<213> ORGANISM: Homo sapien

<400> SEQUENCE: 260

```
ttttttttct ccctaaggaa aaagaaggaa caagtctcat aaaaccaaat aagcaatggt      60
aaggtgtctt aacttgaaaa agattaggag tcactggttt acaagttata attgaatgaa     120
agaactgtaa cagccacagt tggccatttc atgccaatgg cagcaaacaa caggattaac     180
tagggcaaaa taaataagtg tgtggaagcc ctgataagtg cttaataaac agactgattc     240
actgagacat cagtacctgc ccgggcggcc gctcgagccg aattctgcag atatccatca     300
c                                                                    301
```

<210> SEQ ID NO 261
<211> LENGTH: 301
<212> TYPE: DNA
<213> ORGANISM: Homo sapien

<400> SEQUENCE: 261

```
aaatattcga gcaaatcctg taactaatgt gtctccataa aaggctttga actcagtgaa      60
tctgcttcca tccacgattc tagcaatgac ctctcggaca tcaaagctcc tcttaaggtt     120
agcaccaact attccataca attcatcagc aggaaataaa ggctcttcag aaggttcaat     180
ggtgacatcc aatttcttct gataatttag attcctcaca accttcctag ttaagtgaag     240
ggcatgatga tcatccaaag cccagtggtc acttactcca gactttctgc aatgaagatc     300
a                                                                    301
```

<210> SEQ ID NO 262
<211> LENGTH: 301
<212> TYPE: DNA
<213> ORGANISM: Homo sapien

<400> SEQUENCE: 262

```
gaggagagcc tgttacagca tttgtaagca cagaatactc caggagtatt tgtaattgtc      60
tgtgagcttc ttgccgcaag tctctcagaa atttaaaaag atgcaaatcc ctgagtcacc     120
cctagacttc ctaaaccaga tcctctgggg ctggaacctg gcactctgca tttgtaatga     180
gggctttctg gtgcacacct aatttgtgc atctttgccc taaatcctgg attagtgccc      240
catcattacc cccacattat aatgggatag attcagagca gatactctcc agcaaagaat     300
c                                                                    301
```

<210> SEQ ID NO 263
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 263

```
tttagcttgt ggtaaatgac tcacaaaact gattttaaaa tcaagttaat gtgaattttg      60
aaaattacta cttaatccta attcacaata acaatggcat taaggtttga cttgagttgg     120
ttcttagtat tatttatggt aaataggctc ttaccacttg caaataactg gccacatcat     180
taatgactga cttcccagta aggctctcta aggggtaagt angaggatcc acaggatttg     240
agatgctaag gccccagaga tcgtttgatc caaccctctt attttcagag gggaaaatgg     300
```

<210> SEQ ID NO 264
<211> LENGTH: 301
<212> TYPE: DNA
<213> ORGANISM: Homo sapien

<400> SEQUENCE: 264

| aaagacgtta aaccactcta ctaccacttg tggaactctc aaagggtaaa tgacaaasc | 60 |
| aatgaatgac tctaaaaaca atatttacat ttaatggttt gtagacaata aaaaaacaa | 120 |
| gtggatagat ctagaattgt aacattttaa gaaaaccata scatttgaca gatgagaaa | 180 |
| ctcaattata gatgcaaagt tataactaaa ctactatagt agtaaagaaa tacatttca | 240 |
| acccttcata taaattcact atcttggctt gaggcactcc ataaaatgta tcacgtgca | 300 |
| a | 301 |

<210> SEQ ID NO 265
<211> LENGTH: 301
<212> TYPE: DNA
<213> ORGANISM: Homo sapien

<400> SEQUENCE: 265

| tgcccaagtt atgtgtaagt gtatccgcac ccagaggtaa aactacactg tcatctttgt | 60 |
| cttcttgtga cgcagtattt cttctctggg gagaagccgg gaagtcttct cctggctcta | 120 |
| catattcttg gaagtctcta atcaactttt gttccatttg tttcatttct tcaggaggga | 180 |
| ttttcagttt gtcaacatgt tctctaacaa cacttgccca tttctgtaaa gaatccaaag | 240 |
| cagtccaagg ctttgacatg tcaacaacca gcataactag agtatccttc agagatacgg | 300 |
| c | 301 |

<210> SEQ ID NO 266
<211> LENGTH: 301
<212> TYPE: DNA
<213> ORGANISM: Homo sapien

<400> SEQUENCE: 266

| taccgtctgc ccttcctccc atccaggcca tctgcgaatc tacatgggtc ctcctattcg | 60 |
| acaccagatc actctttcct ctacccacag gcttgctatg agcaagagac acaacctcct | 120 |
| ctcttctgtg ttccagcttc ttttcctgtt cttcccaccc cttaagttct attcctgggg | 180 |
| atagagacac caatacccat aacctctctc ctaagcctcc ttataaccca gggtgcacag | 240 |
| cacagactcc tgacaactgg taaggccaat gaactgggag ctcacagctg gctgtgcctg | 300 |
| a | 301 |

<210> SEQ ID NO 267
<211> LENGTH: 301
<212> TYPE: DNA
<213> ORGANISM: Homo sapien

<400> SEQUENCE: 267

| aaagagcaca ggccagctca gcctgccctg gccatctaga ctcagcctgg ctccatgggg | 60 |
| gttctcagtg ctgagtccat ccaggaaaag ctcacctaga ccttctgagg ctgaatcttc | 120 |
| atcctcacag gcagcttctg agagcctgat attcctagcc ttgatggtct ggagtaaagc | 180 |
| ctcattctga ttcctctcct tcttttcttt caagttggct ttcctcacat ccctctgttc | 240 |
| aattcgcttc agcttgtctg ctttagccct catttccaga agcttcttct ctttggcatc | 300 |

```
t                                                                301

<210> SEQ ID NO 268
<211> LENGTH: 301
<212> TYPE: DNA
<213> ORGANISM: Homo sapien

<400> SEQUENCE: 268
aatgtctcac tcaactactt cccagcctac cgtggcctaa ttctgggagt tttcttctta    60
gatcttggga gagctggttc ttctaaggag aaggaggaag acagatgta actttggatc    120 tcgaagagga agtctaatgg aagtaattag tcaacggtcc ttgtttagac tcttggaata   180
tgctgggtgg ctcagtgagc cctttggag aaagcaagta ttattcttaa ggagtaacca    240
cttcccattg ttctactttc taccatcatc aattgtatat tatgtattct ttggagaact   300
a                                                                301

<210> SEQ ID NO 269
<211> LENGTH: 301
<212> TYPE: DNA
<213> ORGANISM: Homo sapien

<400> SEQUENCE: 269
taacaatata cactagctat cttttaact gtccatcatt agcaccaatg aagattcaat     60
aaaattacct ttattcacac atctcaaaac aattctgcaa attcttagtg aagtttaact   120
atagtcacag accttaaata ttcacattgt tttctatgtc tactgaaaat aagttcacta   180
cttttctgga tattctttac aaaatcttat taaaattcct ggtattatca ccccaatta    240 tacagtagca caaccacctt atgtagtttt tacatgatag ctctgtagaa gtttcacatc   300
t                                                                301

<210> SEQ ID NO 270
<211> LENGTH: 301
<212> TYPE: DNA
<213> ORGANISM: Homo sapien

<400> SEQUENCE: 270
cattgaagag cttttgcgaa acatcagaac acaagtgctt ataaaattaa ttaagcctta    60
cacaagaata catattcctt ttatttctaa ggagttaaac atagatgtag ctgatgtgga   120
gagcttgctg gtgcagtgca tattggataa cactattcat ggccgaattg atcaagtcaa   180
ccaactcctt gaactggatc atcagaagaa gggtggtgca cgatatactg cactagataa   240
tggaccaacc aactaaattc tctcaccagg ctgtatcagt aaactggctt aacagaaaac   300
a                                                                301

<210> SEQ ID NO 271
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 271
aaaaggttct cataagatta acaatttaaa taaatatttg atagaacatt ctttctcatt    60
tttatagctc atctttaggg ttgatattca gttcatgctt cccttgctgt tcttgatcca   120
```

| | |
|---|---:|
| gaattgcaat cacttcatca gcctgtattc gctccaattc tctataaagt gggtccaagg | 180 |
| tgaaccacag agccacagca cacctctttc ccttggtgac tgccttcacc ccatganggt | 240 |
| tctctcctcc agatganaac tgatcatgcg cccacatttt gggttttata gaagcagtca | 300 |
| c | 301 |

<210> SEQ ID NO 272
<211> LENGTH: 301
<212> TYPE: DNA
<213> ORGANISM: Homo sapien

<400> SEQUENCE: 272

| | |
|---|---:|
| taaattgcta agccacagat aacaccaatc aaatggaaca aatcactgtc ttcaaatgtc | 60 |
| ttatcagaaa accaaatgag cctggaatct tcataatacc taaacatgcc gtatttagga | 120 |
| tccataatt ccctcatgat gagcaagaaa aattctttgc gcaccctcc tgcatccaca | 180 |
| gcatcttctc caacaaatat aaccttgagt ggcttcttgt aatctatgtt ctttgttttc | 240 |
| ctaaggactt ccattgcatc tcctacaata ttttctctac gcaccactag aattaagcag | 300 |
| g | 301 |

<210> SEQ ID NO 273
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 273

| | |
|---|---:|
| acatgtgtgt atgtgtatct ttgggaaaan aanaagacat cttgtttayt atttttttgg | 60 |
| agagangctg ggacatggat aatcacwtaa tttgctayta tyacttttaat ctgactygaa | 120 |
| gaaccgtcta aaaataaaat ttaccatgtc dtatattcct tatagtatgc ttatttcacc | 180 |
| ttytttctgt ccagagagag tatcagtgac ananatttma gggtgaamac atgmattggt | 240 |
| gggacttnty tttacngagm accctgcccg sgcgccctcg makcngantt ccgcsananc | 300 |
| t | 301 |

<210> SEQ ID NO 274
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 274

| | |
|---|---:|
| cttatatact ctttctcaga ggcaaaagag gagatgggta atgtagacaa ttctttgagg | 60 |
| aacagtaaat gattattaga gagaangaat ggaccaagga gacagaaatt aacttgtaaa | 120 |
| tgattctctt tggaatctga atgagatcaa gaggccagct ttagcttgtg gaaaagtcca | 180 |
| tctaggtatg gttgcattct cgtcttcttt tctgcagtag ataatgaggt aaccgaaggc | 240 |
| aattgtgctt cttttgataa gaagctttct tggtcatatc aggaaattcc aganaaagtc | 300 |
| c | 301 |

<210> SEQ ID NO 275
<211> LENGTH: 301

<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 275

| | |
|---|---|
| tcggtgtcag cagcacgtgg cattgaacat tgcaatgtgg agcccaaacc acagaaaatg | 60 |
| gggtgaaatt ggccaacttt ctattaactt atgttggcaa ttttgccacc aacagtaagc | 120 |
| tggcccttct aataaaagaa aattgaaagg tttctcacta aacggaatta agtagtggag | 180 |
| tcaagagact cccaggcctc agcgtacctg cccgggcggc cgctcgaagc cgaattctgc | 240 |
| agatatccat cacactggcg gncgctcgan catgcatcta gaaggnccaa ttcgccctat | 300 |
| a | 301 |

<210> SEQ ID NO 276
<211> LENGTH: 301
<212> TYPE: DNA
<213> ORGANISM: Homo sapien

<400> SEQUENCE: 276

| | |
|---|---|
| tgtacacata ctcaataaat aaatgactgc attgtggtat tattactata ctgattatat | 60 |
| ttatcatgtg acttctaatt agaaaatgta tccaaaagca aaacagcaga tatacaaaat | 120 |
| taaagagaca gaagatagac attaacagat aaggcaactt atacattgag aatccaaatc | 180 |
| caatacattt aaacatttgg gaatgagggg ggacaaatgg aagccagatc aaatttgtgt | 240 |
| aaaactattc agtatgtttc ccttgcttca tgtctgagaa ggctctcctt caatggggat | 300 |
| g | 301 |

<210> SEQ ID NO 277
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 277

| | |
|---|---|
| tttgttgatg tcagtatttt attacttgcg ttatgagtgc tcacctggga aattctaaag | 60 |
| atacagagga cttggaggaa gcagagcaac tgaatttaat ttaaaagaag gaaaacattg | 120 |
| gaatcatggc actcctgata ctttcccaaa tcaacactct caatgcccca ccctcgtcct | 180 |
| caccatagtg gggagactaa agtggccacg gatttgcctt angtgtgcag tgcgttctga | 240 |
| gttcnctgtc gattacatct gaccagtctc cttttccga agtccntccg ttcaatcttg | 300 |
| c | 301 |

<210> SEQ ID NO 278
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 278

| | |
|---|---|
| taccactaca ctccagcctg ggcaacagag caagacctgt ctcaaagcat aaaatggaat | 60 |

```
aacatatcaa atgaaacagg gaaaatgaag ctgacaattt atggaagcca gggcttgtca    120
cagtctctac tgttattatg cattacctgg gaatttatat aagcccttaa taataatgcc    180
aatgaacatc tcatgtgtgc tcacaatgtt ctggcactat tataagtgct tcacaggttt    240
tatgtgttct tcgtaacttt atggantagg tactcggccg cgaacacgct aagccgaatt    300
c                                                                    301
```

<210> SEQ ID NO 279
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 279

```
aaagcaggaa tgacaaagct tgcttttctg gtatgttcta ggtgtattgt gacttttact    60
gttatattaa ttgccaatat aagtaaatat agattatata tgtatagtgt ttcacaaagc   120
ttagaccttt accttccagc cacccccacag tgcttgatat ttcagagtca gtcattggtt   180
atacatgtgt agttccaaag cacataagct agaanaanaa atatttctag ggagcactac   240
catctgtttt cacatgaaat gccacacaca tagaactcca acatcaattt cattgcacag   300
a                                                                    301
```

<210> SEQ ID NO 280
<211> LENGTH: 301
<212> TYPE: DNA
<213> ORGANISM: Homo sapien

<400> SEQUENCE: 280

```
ggtactggag ttttcctccc ctgtgaaaac gtaactactg ttgggagtga attgaggatg    60
tagaaaggtg gtggaaccaa attgtggtca atggaaatag gagaatatgg ttctcactct   120
tgagaaaaaa acctaagatt agcccaggta gttgcctgta acttcagttt ttctgcctgg   180
gtttgatata gtttagggtt ggggttagat taagatctaa attacatcag gacaaagaga   240
cagactatta actccacagt taattaagga ggtatgttcc atgtttattt gttaaagcag   300
t                                                                    301
```

<210> SEQ ID NO 281
<211> LENGTH: 301
<212> TYPE: DNA
<213> ORGANISM: Homo sapien

<400> SEQUENCE: 281

```
aggtacaaga aggggaatgg gaaagagctg ctgctgtggc attgttcaac ttggatattc    60
gccgagcaat ccaaatcctg aatgaagggg catcttctga aaaggagat ctgaatctca   120 atgtggtagc aatggcttta tcgggttata cggatgagaa gaactccctt tggagagaaa   180
tgtgtagcac actgcgatta cagctaaata acccgtattt gtgtgtcatg tttgcatttc   240
tgacaagtga aacaggatct tacgatggag ttttgtatga aaacaaagtt gcagtacctc   300
g                                                                    301
```

<210> SEQ ID NO 282
<211> LENGTH: 301
<212> TYPE: DNA
<213> ORGANISM: Homo sapien

<400> SEQUENCE: 282

| caggtactac | agaattaaaa | tactgacaag | caagtagttt | cttggcgtgc | acgaattgca | 60 |
| tccagaaccc | aaaaattaag | aaattcaaaa | agacattttg | tgggcacctg | ctagcacaga | 120 |
| agcgcagaag | caaagcccag | gcagaaccat | gctaacctta | cagctcagcc | tgcacagaag | 180 |
| cgcagaagca | aagcccaggc | agaaccatgc | taaccttaca | gctcagcctg | cacagaagcg | 240 |
| cagaagcaaa | gcccaggcag | aacatgctaa | ccttacagct | cagcctgcac | agaagcacag | 300 |
| a | | | | | | 301 |

<210> SEQ ID NO 283
<211> LENGTH: 301
<212> TYPE: DNA
<213> ORGANISM: Homo sapien

<400> SEQUENCE: 283

| atctgtatac | ggcagacaaa | ctttatarag | tgtagagagg | tgagcgaaag | gatgcaaaag | 60 |
| cactttgagg | gctttataat | aatatgctgc | ttgaaaaaaa | aaatgtgtag | ttgatactca | 120 |
| gtgcatctcc | agacatagta | aggggttgct | ctgaccaatc | aggtgatcat | tttttctatc | 180 |
| acttcccagg | ttttatgcaa | aaattttgtt | aaattctata | atggtgatat | gcatctttta | 240 |
| ggaaacatat | acatttttaa | aaatctattt | tatgtaagaa | ctgacagacg | aatttgcttt | 300 |
| g | | | | | | 301 |

<210> SEQ ID NO 284
<211> LENGTH: 301
<212> TYPE: DNA
<213> ORGANISM: Homo sapien

<400> SEQUENCE: 284

| caggtacaaa | acgctattaa | gtggcttaga | atttgaacat | ttgtggtctt | tatttacttt | 60 |
| gcttcgtgtg | tgggcaaagc | aacatcttcc | ctaaatatat | attaccaaga | aaagcaagaa | 120 |
| gcagattagg | ttttttgacaa | aacaaacagg | ccaaaagggg | gctgacctgg | agcagagcat | 180 |
| ggtgagaggc | aaggcatgag | agggcaagtt | tgttgtggac | agatctgtgc | ctactttatt | 240 |
| actggagtaa | aagaaaacaa | agttcattga | tgtcgaagga | tatatacagt | gttagaaatt | 300 |
| a | | | | | | 301 |

<210> SEQ ID NO 285
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 285

| acatcaccat | gatcggatcc | cccacccatt | atacgttgta | tgtttacata | aatactcttc | 60 |
| aatgatcatt | agtgttttaa | aaaaaatact | gaaaactcct | tctgcatccc | aatctctaac | 120 |
| caggaaagca | aatgctattt | acagacctgc | aagccctccc | tcaaacnaaa | ctatttctgg | 180 |
| attaaatatg | tctgacttct | tttgaggtca | cacgactagg | caaatgctat | ttacgatctg | 240 |
| caaaagctgt | tgaagagtc | aaagccccca | tgtgaacacg | atttctggac | cctgtaacag | 300 |
| t | | | | | | 301 |

<210> SEQ ID NO 286
<211> LENGTH: 301
<212> TYPE: DNA
<213> ORGANISM: Homo sapien

<400> SEQUENCE: 286

| | | | | | |
|---|---|---|---|---|---|
| taccactgca | ttccagcctg | ggtgacagag | tgagactccg | tctccaaaaa | aaactttgct | 60 |
| tgtatattat | ttttgcctta | cagtggatca | ttctagtagg | aaaggacagt | aagatttttt | 120 |
| atcaaaatgt | gtcatgccag | taagagatgt | tatattctttt | tctcatttct | tccccaccca | 180 |
| aaaataagct | accatatagc | ttataagtct | caaattttttg | cctttttacta | aaatgtgatt | 240 |
| gtttctgttc | attgtgtatg | cttcatcacc | tatattaggc | aaattccatt | ttttcccttg | 300 |
| t | | | | | | 301 |

<210> SEQ ID NO 287
<211> LENGTH: 301
<212> TYPE: DNA
<213> ORGANISM: Homo sapien

<400> SEQUENCE: 287

| | | | | | |
|---|---|---|---|---|---|
| tacagatctg | ggaactaaat | attaaaaatg | agtgtggctg | gatatatgga | gaatgttggg | 60 |
| cccagaagga | acgtagagat | cagatattac | aacagctttg | ttttgagggt | tagaaatatg | 120 |
| aaatgatttg | gttatgaacg | cacagtttag | gcagcagggc | cagaatcctg | accctctgcc | 180 |
| ccgtggttat | ctcctcccca | gcttggctgc | ctcatgttat | cacagtattc | cattttgttt | 240 |
| gttgcatgtc | ttgtgaagcc | atcaagattt | tctcgtctgt | tttcctctca | ttggtaatgc | 300 |
| t | | | | | | 301 |

<210> SEQ ID NO 288
<211> LENGTH: 301
<212> TYPE: DNA
<213> ORGANISM: Homo sapien

<400> SEQUENCE: 288

| | | | | | |
|---|---|---|---|---|---|
| gtacacctaa | ctgcaaggac | agctgaggaa | tgtaatgggc | agccgctttt | aaagaagtag | 60 |
| agtcaatagg | aagacaaatt | ccagttccag | ctcagtctgg | gtatctgcaa | agctgcaaaa | 120 |
| gatcttttaaa | gacaatttca | agagaatatt | tccttaaagt | tggcaatttg | gagatcatac | 180 |
| aaaagcatct | gcttttgtga | tttaatttag | ctcatctggc | cactggaaga | atccaaacag | 240 |
| tctgccttaa | ttttggatga | atgcatgatg | gaaattcaat | aatttagaaa | gttaaaaaaa | 300 |
| a | | | | | | 301 |

<210> SEQ ID NO 289
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 289

| | | | | | |
|---|---|---|---|---|---|
| ggtacactgt | ttccatgtta | tgtttctaca | cattgctacc | tcagtgctcc | tggaaactta | 60 |
| gcttttgatg | tctccaagta | gtccaccttc | atttaactct | ttgaaactgt | atcatctttg | 120 |
| ccaagtaaga | gtggtggcct | atttcagctg | ctttgacaaa | atgactggct | cctgacttaa | 180 |
| cgttctataa | atgaatgtgc | tgaagcaaag | tgcccatggt | ggcggcgaan | aagagaaaga | 240 |

```
tgtgttttgt tttggactct ctgtggtccc ttccaatgct gtgggtttcc aaccagngga     300
a                                                                    301

<210> SEQ ID NO 290
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 290
acactgagct cttcttgata aatatacaga atgcttggca tatacaagat tctatactac     60
tgactgatct gttcatttct ctcacagctc ttaccccaa aagcttttcc accctaagtg    120
ttctgacctc cttttctaat cacagtaggg atagaggcag anccacctac aatgaacatg    180
gagttctatc aagaggcaga aacagcacag aatcccagtt ttaccattcg ctagcagtgc    240
tgccttgaac aaaaacattt ctccatgtct cattttcttc atgcctcaag taacagtgag    300
a                                                                    301

<210> SEQ ID NO 291
<211> LENGTH: 301
<212> TYPE: DNA
<213> ORGANISM: Homo sapien

<400> SEQUENCE: 291
caggtaccaa ttcttctat cctagaaaca tttcatttta tgttgttgaa acataacaac     60
tatatcagct agatttttt tctatgcttt acctgctatg gaaaatttga cacattctgc    120
tttactcttt tgtttatagg tgaatcacaa aatgtatttt tatgtattct gtagttcaat    180
agccatggct gtttacttca tttaatttat ttagcataaa gacattatga aaaggcctaa    240
acatgagctt cacttcccca ctaactaatt agcatctgtt atttcttaac cgtaatgcct    300
a                                                                    301

<210> SEQ ID NO 292
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 292 acctttagt agtaatgtct aataataaat aagaaatcaa ttttataagg tccatatagc     60
tgtattaaat aatttttaag tttaaaagat aaaataccat catttaaat gttggtattc    120 aaaaccaaag natataaccg aaaggaaaaa cagatgagac ataaaatgat ttgcnagatg    180
ggaaatatag tasttyatga atgttnatta aattccagtt ataatagtgg ctacacactc    240
tcactacaca cacagaccc acagtcctat atgccacaaa cacatttcca taacttgaaa    300
a                                                                    301

<210> SEQ ID NO 293
<211> LENGTH: 301
<212> TYPE: DNA
<213> ORGANISM: Homo sapien
```

<400> SEQUENCE: 293

```
ggtaccaagt gctggtgcca gcctgttacc tgttctcact gaaaagtctg gctaatgctc      60
ttgtgtagtc acttctgatt ctgacaatca atcaatcaat ggcctagagc actgactgtt     120
aacacaaacg tcactagcaa agtagcaaca gctttaagtc taaatacaaa gctgttctgt     180
gtgagaattt tttaaaaggc tacttgtata ataacccttg tcattttttaa tgtacctcgg    240
ccgcgaccac gctaagccga attctgcaga tatccatcac actggcggcc gctcgagcat    300
g                                                                     301
```

<210> SEQ ID NO 294
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 294

```
tgacccataa caatatacac tagctatctt tttaactgtc catcattagc accaatgaag      60
attcaataaa attacccttta ttcacacatc tcaaaacaat tctgcaaatt cttagtgaag   120
tttaactata gtcacaganc ttaaatattc acattgtttt ctatgtctac tgaaaataag    180
ttcactactt ttctgggata ttctttacaa aatcttatta aaattcctgg tattatcacc     240
cccaattata cagtagcaca accaccttat gtagttttta catgatagct ctgtagaggt     300
t                                                                     301
```

<210> SEQ ID NO 295
<211> LENGTH: 305
<212> TYPE: DNA
<213> ORGANISM: Homo sapien

<400> SEQUENCE: 295

```
gtactctttc tctcccctcc tctgaattta attctttcaa cttgcaattt gcaaggatta      60
cacatttcac tgtgatgtat attgtgttgc aaaaaaaaaa gtgtctttgt ttaaaattac    120
ttggtttgtg aatccatctt gcttttttccc cattggaact agtcattaac ccatctctga   180
actggtagaa aaacrtctga agagctagtc tatcagcatc tgacaggtga attggatggt    240
tctcagaacc atttcaccca gacagcctgt ttctatcctg tttaataaat tagtttgggt    300
tctct                                                                 305
```

<210> SEQ ID NO 296
<211> LENGTH: 301
<212> TYPE: DNA
<213> ORGANISM: Homo sapien

<400> SEQUENCE: 296

```
aggtactatg ggaagctgct aaaataatat ttgatagtaa agtatgtaa tgtgctatct       60
cacctagtag taaactaaaa ataaactgaa actttatgga atctgaagtt attttccttg    120
attaaataga attaataaac caatatgagg aaacatgaaa ccatgcaatc tactatcaac    180
tttgaaaaag tgattgaacg aaccacttag ctttcagatg atgaacactg ataagtcatt    240
tgtcattact ataaattttta aaatctgtta ataagatggc ctatagggag gaaaagggg    300
c                                                                     301
```

```
<210> SEQ ID NO 297
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 297
actgagtttt aactggacgc caagcaggca aggctggaag gttttgctct ctttgtgcta      60
aaggttttga aaaccttgaa ggagaatcat tttgacaaga agtacttaag agtctagaga    120
acaaagangt gaaccagctg aaagctctcg ggggaanctt acatgtgttg ttaggcctgt    180
tccatcattg ggagtgcact ggccatccct caaaatttgt ctgggctggc ctgagtggtc    240
accgcacctc ggccgcgacc acgctaagcc gaattctgca gatatccatc acactggcgg    300

<210> SEQ ID NO 298
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 298
tatggggttt gtcacccaaa agctgatgct gagaaaggcc tccctggggc ccctcccgcg      60
ggcatctgag agacctggtg ttccagtgtt tctggaaatg ggtcccagtg ccgccggctg    120
tgaagctctc agatcaatca cgggaagggc ctggcggtgg tggccacctg gaaccaccct    180
gtcctgtctg tttacatttc actaycaggt tttctctggg cattacnatt tgttccccta    240
caacagtgac ctgtgcattc tgctgtggcc tgctgtgtct gcaggtggct ctcagcgagg    300
t                                                                    301

<210> SEQ ID NO 299
<211> LENGTH: 301
<212> TYPE: DNA
<213> ORGANISM: Homo sapien

<400> SEQUENCE: 299
gttttgagac ggagtttcac tcttgttgcc cagactggac tgcaatggca gggtctctgc      60
tcactgcacc ctctgcctcc caggttcgag caattctcct gcctcagcct cccaggtagc    120
tgggattgca ggctcacgcc accataccca gctaatttt ttgtattttt agtagagacg    180
gagtttcgcc atgttggcca gctggtctca aactcctgac ctcaagcgac ctgcctgcct    240
cggcctccca aagtgctgga attataggca tgagtcaaca cgcccagcct aaagatattt    300
t                                                                    301

<210> SEQ ID NO 300
<211> LENGTH: 301
<212> TYPE: DNA
<213> ORGANISM: Homo sapien

<400> SEQUENCE: 300
attcagtttt atttgctgcc ccagtatctg taaccaggag tgccacaaaa tcttgccaga      60
tatgtcccac acccactggg aaaggctccc acctggctac ttcctctatc agctgggtca    120
gctgcattcc acaaggttct cagcctaatg agtttcacta cctgccagtc tcaaaactta    180
```

```
gtaaagcaag accatgacat tcccccacgg aaatcagagt ttgccccacc gtcttgttac    240
tataaagcct gcctctaaca gtccttgctt cttcacacca atcccgagcg catcccccat    300
g                                                                    301

<210> SEQ ID NO 301
<211> LENGTH: 301
<212> TYPE: DNA
<213> ORGANISM: Homo sapien

<400> SEQUENCE: 301 ttaaatttt gagaggataa aaggacaaa taatctagaa atgtgtcttc ttcagtctgc      60
agaggacccc aggtctccaa gcaaccacat ggtcaagggc atgaataatt aaaagttggt    120
gggaactcac aaagaccctc agagctgaga cacccacaac agtgggagct cacaaagacc    180
ctcagagctg agacacccac aacagtggga gctcacaaag accctcagag ctgagacacc    240
cacaacagca cctcgttcag ctgccacatg tgtgaataag gatgcaatgt ccagaagtgt    300
t                                                                    301

<210> SEQ ID NO 302
<211> LENGTH: 301
<212> TYPE: DNA
<213> ORGANISM: Homo sapien

<400> SEQUENCE: 302
aggtacacat ttagcttgtg gtaaatgact cacaaaactg attttaaaat caagttaatg    60
tgaattttga aaattactac ttaatcctaa ttcacaataa caatggcatt aaggtttgac    120
ttgagttggt tcttagtatt atttatggta ataggctct taccacttgc aaataactgg     180
ccacatcatt aatgactgac ttcccagtaa ggctctctaa ggggtaagta ggaggatcca    240
caggatttga gatgctaagg ccccagagat cgtttgatcc aaccctctta ttttcagagg    300
g                                                                    301

<210> SEQ ID NO 303
<211> LENGTH: 301
<212> TYPE: DNA
<213> ORGANISM: Homo sapien

<400> SEQUENCE: 303
aggtaccaac tgtggaaata ggtagaggat catttttct ttccatatca actaagttgt     60
atattgtttt ttgacagttt aacacatctt cttctgtcag agattctttc acaatagcac    120
tggctaatgg aactaccgct tgcatgttaa aaatggtggt ttgtgaaatg atcataggcc    180
agtaacgggt atgtttttct aactgatctt ttgctcgttc caaagggacc tcaagacttc    240
catcgatttt atatctgggg tctagaaaag gagttaatct gttttccctc ataaattcac    300
c                                                                    301

<210> SEQ ID NO 304
<211> LENGTH: 301
<212> TYPE: DNA
<213> ORGANISM: Homo sapien

<400> SEQUENCE: 304
acatggatgt tattttgcag actgtcaacc tgaatttgta tttgcttgac attgcctaat    60
tattagtttc agtttcagct tacccacttt ttgtctgcaa catgcaraas agacagtgcc    120 cttttttagtg tatcatatca ggaatcatct cacattggtt tgtgccatta ctggtgcagt    180
```

```
gactttcagc cacttgggta aggtggagtt ggccatatgt ctccactgca aaattactga      240
tttccttttt gtaattaata agtgtgtgtg tgaagattct ttgagatgag gtatatatct      300
c                                                                      301
```

<210> SEQ ID NO 305
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 305

```
gangtacagc gtggtcaagg taacaagaag aaaaaaatgt gagtggcatc ctgggatgag       60 caggggaca gacctggaca gacacgttgt catttgctgc tgtgggtagg aaaatgggcg       120 taaggagga gaaacagata caaaatctcc aactcagtat taaggtattc tcatgcctag      180
aatattggta gaaacaagaa tacattcata tggcaaataa ctaaccatgg tggaacaaaa     240
ttctgggatt taagttggat accaangaaa ttgtattaaa agagctgttc atggaataag    300
a                                                                      301
```

<210> SEQ ID NO 306
<211> LENGTH: 8
<212> TYPE: PRT
<213> ORGANISM: Homo sapien

<400> SEQUENCE: 306

```
Val Leu Gly Trp Val Ala Glu Leu
 1               5
```

COMPOUNDS FOR IMMUNOTHERAPY OF PROSTATE CANCER AND METHODS FOR THEIR USE

CROSS REFERENCE TO RELATED APPLICATIONS

This application is a continuation-in-part of U.S. patent application Ser. No. 09/115,453, filed Jul. 14, 1998, which is a continuation-in-part of U.S. patent application Ser. No. 09/030,607, filed Feb. 25, 1998, U.S. Pat. No. 6,262,245 which is a continuation-in-part of U.S. patent application Ser. No. 09/020,956, filed Feb. 9, 1998, U.S. Pat. No. 6,261,562 which is a continuation-in-part of U.S. patent application Ser. No. 08/904,804, filed Aug. 1, 1997, abandoned which is a continuation-in-part of U.S. patent application Ser. No. 08/806,099, filed Feb. 25, 1997 abandoned.

TECHNICAL FIELD

The present invention relates generally to compositions and methods for the treatment of prostate cancer. The invention is more particularly related to polypeptides comprising at least a portion of a prostate tumor protein and to DNA molecules encoding such polypeptides. Such polypeptides may be used in vaccines and pharmaceutical compositions for treatment of prostate cancer.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

Accordingly, there remains a need in the art for improved vaccines and treatment methods for prostate cancer. The present invention fulfills these needs and further provides other related advantages.

SUMMARY OF THE INVENTION

The present invention provides compounds and methods for immunotherapy of prostate cancer. In one aspect, isolated polypeptides are provided comprising at least an immunogenic portion of a prostate tumor protein or a variant thereof that differs only in one or more substitutions, deletions, additions and/or insertions, such that the ability of the variant to react with protein-specific antisera is not substantially diminished. Within certain embodiments, the prostate tumor protein comprises an amino acid sequence encoded by a polynucleotide sequence selected from the group consisting of SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227, 228, and 229 to 305, and complements of such polynucleotides.

In related aspects, isolated polynucleotides encoding the above polypeptides or portions thereof are provided. In specific embodiments, such polynucleotides may comprise a sequence provided in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227 or 228. The present invention further provides expression vectors comprising the above polynucleotides and host cells transformed or transfected with such expression vectors. In preferred embodiments, the host cells are selected from the group consisting of E. coli, yeast and mammalian cells.

In another aspect, the present invention provides fusion proteins comprising at least one polypeptide as described above, in combination with a second polypeptide as described above and/or a known prostate tumor antigen. Polynucleotides encoding such fusion proteins are further provided.

The present invention also provides pharmaceutical compositions comprising one or more of the above polypeptides, or a DNA molecule encoding such polypeptides, and a physiologically acceptable carrier, together with vaccines comprising one or more of such polypeptide or DNA molecules in combination with a non-specific immune response enhancer.

Within other aspects, the present invention provides pharmaceutical compositions comprising (a) an antibody that specifically binds to a prostate tumor protein that comprises an amino acid sequence that is encoded by a polynucleotide sequence selected from the group consisting of (i) nucleotide sequences recited in any one of SEQ ID NOS: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227, 228, or 229 to 305; and (ii) complements of the foregoing polynucleotide sequences; and (b) a physiologically acceptable carrier. Vaccines are also provided, comprising one or more such antibodies in combination with a non-specific immune response enhancer.

Within other aspects, the present invention provides pharmaceutical compositions comprising (a) a T cell that specifically reacts with a prostate tumor protein that comprises an amino acid sequence that is encoded by a polynucleotide sequence selected from the group consisting of (i) nucleotide sequences recited in any one of SEQ ID NOS: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227, 228, or 229 to 305; and (ii) complements of the foregoing polynucleotide sequences; and (b) a physiologically acceptable carrier. Vaccines are also provided, comprising one or more such T cells in combination with a non-specific immune response enhancer.

In yet another aspect, methods are provided for inhibiting the development of prostate cancer in a patient, comprising administering an effective amount of at least one of the above pharmaceutical compositions and/or vaccines.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

In FIG. 2A, data is presented for fibroblasts pulsed with the P2S-12 peptide, as compared to fibroblasts pulsed with a control E75 peptide. In FIG. 2B, data is presented for fibroblasts expressing P506, as compared to fibroblasts expressing HER-2/neu.

DETAILED DESCRIPTION OF THE INVENTION

Figure 1:
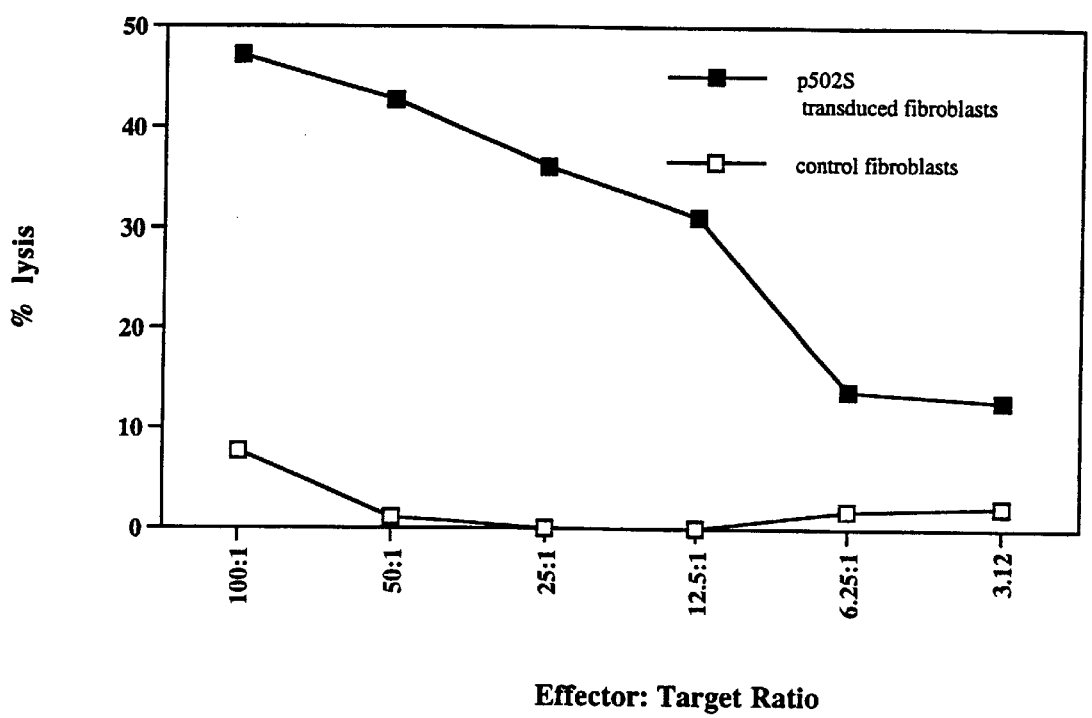
FIG. 1 is a graph illustrating the ability of T cells to kill fibroblasts expressing the representative prostate tumor polypeptide P502S, as compared to control fibroblasts. The % lysis is shown at a series of effector:target ratios, as indicated.

As noted above, the present invention is generally directed to compositions and methods for the therapy of cancer, such as prostate cancer. The compositions described herein may include one or more prostate tumor polypeptides, nucleic acid sequences encoding such polypeptides, binding agents such as antibodies that bind to a polypeptide and/or immune system cells (e.g., T cells). Prostate tumor polypeptides of the present invention generally comprise at least a portion of a prostate tumor protein or a variant thereof, such that the therapeutic, antigenic and/or immunogenic properties of the polypeptide are not substantially diminished relative to the native prostate tumor protein. A "prostate tumor protein" is a protein that is overexpressed (i.e., mRNA and/or protein is present at a level that is at least two fold higher) in prostate tumor tissue, relative to normal prostate tissue and/or relative to other tissues (e.g., brain, heart, kidney, liver, lung, pancreas, ovary, placenta, skeletal muscle, spleen and/or thymus). Nucleic acid sequences of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a portion of a polypeptide as described above. T cells that may be employed within such compositions are generally T cells that are specific for a polypeptide as described above.

The present invention is based on the discovery of previously unknown human prostate tumor proteins. Partial sequences of polynucleotides encoding specific prostate tumor proteins (or complementary to such coding sequences) are provided in SEQ ID NOs:2, 3, 8–29, 41–45, 47–52, 54–65, 70, 73–74, 79, 81, 87, 90, 92, 93, 97, 103, 104, 107, 109–111, 115–160, 181, 188, 191, 193, 194, 198, 203, 204, 207–228 and 229 to 305.

Prostate Tumor Polynucleotides

Any polynucleotide that encodes a prostate tumor protein or a portion or other variant thereof as described herein is encompassed by the present invention. Preferred polynucleotides comprise at least 15 consecutive nucleotides, and preferably at least 30 consecutive nucleotides, that encode a portion of a prostate tumor protein. More preferably, a polynucleotide encodes an immunogenic portion of a prostate tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a prostate tumor protein or a portion thereof) or may comprise a variant of such a sequence. Polynucleotide variants may contain one or more substitutions, additions, deletions and/or insertions such that the therapeutic, antigenic and/or immunogenic properties are not substantially diminished, relative to a native prostate tumor protein. Preferably, the antigenicity or immunogenicity of a polypeptide variant is not substantially diminished. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native prostate tumor protein or a portion thereof. The percent identity may be readily determined by comparing sequences using computer algorithms well known to those of ordinary skill in the art, such as Megalign, using default parameters. Certain variants are substantially homologous to a native gene, or a portion or complement thereof. Such polynucleotide variants are capable of hybridizing under moderately stringent conditions to a naturally occurring DNA sequence encoding a is native prostate tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

Polynucleotides may be prepared using any of a variety of techniques. For example, a polynucleotide may be identified, as described in more detail below, using a PCR-based subtraction protocol. Alternatively, polypeptides may be amplified via polymerase chain reaction (PCR) from cDNA prepared from prostate tumor cells. For this approach, sequence-specific primers may be designed based on the sequences provided herein, and may be purchased or synthesized.

An amplified portion may be used to isolate a full length gene from a suitable library (e.g., a prostate tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using techniques well known in the art (see, for example, Mullis et al., *Cold Spring Harbor Symp. Quant. Biol.* 51:263, 1987; Erlich ed., *PCR Technology*, Stockton Press, NY, 1989), and software well known in the art may also be employed. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of prostate tumor proteins are provided in SEQ ID NOS: 1–107, 109–111, 115–171, 173–175, 177, 179–228 and 229 to 305. The polynucleotides recited herein, as well as full length polynucleotides comprising such sequences, other portions of such full length polynucleotides, and sequences complementary to all or a portion of such full length molecules, are specifically encompassed by the present invention.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a prostate tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a prostate tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Prostate Tumor Polypeptides

Within the context of the present invention, polypeptides may comprise at least a portion of a prostate tumor protein or a variant thereof, as described herein. As noted above, a "prostate tumor protein" is a protein that is overexpressed by prostate tumor cells, relative to normal prostate cells and/or other tissues such as brain, heart, kidney, liver, lung, pancreas, ovary, placenta, skeletal muscle, spleen and/or thymus. Such polypeptides should comprise a portion of a prostate tumor protein such that the therapeutic, antigenic and/or immunogenic properties of the polypeptide are not substantially diminished, relative to the full length protein. Within certain preferred embodiments, a polypeptide comprises an immunogenic portion of a native prostate tumor protein (i.e., the immunogenic properties of the polypeptide are not substantially diminished). As used herein, the term "polypeptide" encompasses amino acid chains of any length, including full length proteins, wherein the amino acid residues are linked by covalent peptide bonds. In addition to a portion of a prostate tumor protein, additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a prostate tumor protein or a variant thereof. Immunogenic portions of prostate tumor proteins provided herein may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the antigen in an ELISA or other immunoassay, and do not react detectably with unrelated proteins). Such antisera and antibodies may be prepared as described herein, and using well known techniques. An immunogenic portion of a native prostate tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Alternatively, an immunogenic portion may react within such assays at a level that is diminished by less than 50%, and preferably less than 20%, relative to the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a polypeptide may comprise a variant of a native prostate tumor protein. A polypeptide "variant," as used herein, is a polypeptide that differs from a native prostate tumor protein in one or more substitutions, deletions, additions and/or insertions, such that the therapeutic, antigenic and/or immunogenic properties are not substantially diminished. Preferably, the immunogenic properties are not substantially diminished. In other words, the ability of a variant to react with antigen-specific antisera may be enhanced or unchanged, relative to the native antigen, or may be diminished by less than 50%, and preferably less than 20%, relative to the native antigen. Polypeptide variants preferably exhibit at least about 70%, more preferably at least about 90% and most preferably at least about 95% identity to polypeptides encoded by polynucleotides specifically recited herein. Identity may be determined by comparing sequences using computer algorithms well known to those of skill in the art, such as Megalign, using default parameters. For prostate tumor polypeptides with immunoreactive properties, variants may generally be identified by modifying one of the above polypeptide sequences and evaluating the reactivity of the modified polypeptide with antigen-specific antibodies or antisera as described herein. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants containing substitutions may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are E. coli, yeast or a mammalian cell line, such as CHO cells. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known prostate tumor antigen, or a variant of such an antigen. A fusion protein generally comprises at least one of the above immunogenic portions and one or more additional immunogenic prostate tumor sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

Fusion proteins may generally be prepared using standard techniques. For example, a fusion protein may be prepared recombinantly. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence may be incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a prostate tumor protein. As used herein, an agent is said to "specifically bind" to a prostate tumor protein if it reacts at a detectable level (within, for example, an ELISA) with a prostate tumor protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process within, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et at.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. U.S. Pat. No. 4,673,562, to Davison et al. discloses representative chelating compounds and their synthesis.

A variety of routes of administration for the antibodies and immunoconjugates may be used. Typically, administration is intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Pharmaceutical Compositions and Vaccines

Within certain aspects, polypeptides, polynucleotides and/or binding agents may be incorporated into pharmaceutical compositions or vaccines. Pharmaceutical compositions comprise one or more such compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration including, for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, to sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Cancer Therapy

In further aspects of the present invention, the pharmaceutical compositions and vaccines described herein may be used for immunotherapy of cancer, such as prostate cancer, in a patient. Polypeptides for use within such compositions and vaccines generally comprise an immunogenic portion of a prostate tumor protein, or a variant thereof. Such polypeptides may stimulate the patient's own immune response to prostate tumor cells. Alternatively, a pharmaceutical composition or vaccine may comprise one or more fusion proteins comprising one or more such polypeptides and/or DNA encoding such one or more such polypeptides. Monoclonal antibodies of the present invention may also be used as therapeutic reagents, to diminish or eliminate prostate tumors. The antibodies may be used on their own (for instance, to inhibit metastases) or coupled to one or more therapeutic agents, as described above.

Within such methods, pharmaceutical compositions and vaccines are typically administered to a patient. As used herein, a "patient" refers to any warm-blooded animal, preferably a human. A patient may be afflicted with a disease, or may be free of detectable disease. Accordingly, the above pharmaceutical compositions and vaccines may be used to prevent the development of prostate cancer or to treat a patient afflicted with prostate cancer. Prostate cancer may be diagnosed using criteria generally accepted in the art. Pharmaceutical compositions and vaccines may be administered either prior to or following surgical removal of primary tumors and/or treatment such as administration of radiotherapy or conventional chemotherapeutic drugs.

Routes and frequency of administration, as well as dosage, will vary from individual to individual, and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against prostate tumor cells in a treated patient. A suitable immune response is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 mL to about 5 mL. A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Polypeptides disclosed herein may also be employed in ex vivo treatment of prostate cancer. For example, cells of the immune system, such as T cells, may be isolated from the peripheral blood of a patient, using a commercially available cell separation system, such as CellPro Incorporated's (Bothell, Wash.) CEPRATE™ system (see U.S. Pat. Nos. 5,240,856; 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a prostate tumor protein generally correlate with an improved clinical outcome. Such immune responses may generally be evaluated using standard proliferation, cytotoxicity or cytokine assays, which may be performed using samples obtained from a patient before and after treatment.

The following Examples are offered by way of illustration and not by way of limitation.

EXAMPLES

Example 1

Isolation and Characterization of Prostate Tumor Polypeptides

This Example describes the isolation of certain prostate tumor polypeptides from a prostate tumor cDNA library.

A human prostate tumor cDNA expression library was constructed from prostate tumor poly $A^+$ RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly $A^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif.), the cDNA was ligated into the EcoRI/NotI site of pCDNA3.1 (Invitrogen) and transformed into ElectroMax E. coli DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained 1.64×10$^7$ independent colonies, with 70% of clones having an insert and the average insert size being 1745 base pairs. The normal pancreas cDNA library contained 3.3×10$^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood*, 84:189–199, 1994) with some modifications. Specifically, a prostate tumor-specific subtracted cDNA library was generated as follows. Normal pancreas cDNA library (70 μg) was digested with EcoRI, NotI, and SfuI, followed by a filling-in reaction with DNA polymerase Klenow fragment. After phenol-chloroform extraction and ethanol precipitation, the DNA was dissolved in 100 μl of H$_2$O, heat-denatured and mixed with 100 μl (100 μg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 μl) was added and the biotinylation reaction was repeated. After extraction with butanol five times, the DNA was ethanol-precipitated and dissolved in 23 μl H$_2$O to form the driver DNA.

To form the tracer DNA, 10 μg prostate tumor cDNA library was digested with BamHI and XhoI, phenol chloroform extracted and passed through Chroma spin-400 columns (Clontech). Following ethanol precipitation, the tracer DNA was dissolved in 5 μl H$_2$O. Tracer DNA was mixed with 15 μl driver DNA and 20 μl of 2×hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl H$_2$O, mixed with 8 μl driver DNA and 20 μl of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK$^+$ (Stratagene, La Jolla, Calif. 92037) and transformed into ElectroMax *E. coli* DH10B cells by electroporation to generate a prostate tumor specific subtracted cDNA library (prostate subtraction 1).

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 μg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID NOS: 8–9, 10–11, 12–13, 14–15, 16–17, 18–19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID NOS: 30–40, respectively. Comparison of these sequences with those in the gene bank as described above, revealed no significant homologies to three of the five most abundant DNA species, (J1-17, L1-12 and N1-1862; SEQ ID NOS: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to *R. norvegicus* mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27 respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114.

In a further experiment, four additional clones were identified by subtracting a prostate tumor cDNA library with normal prostate cDNA prepared from a pool of three normal prostate poly A+ RNA (prostate subtraction 2). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1-4736, 1G-4738, 1G-4741, 1G-4744, 1G-4734, 1H-4774, 1H-4781, 1-4785, 1H-4787, 1H-4796, 1I-4810, 1I-4811, 1J-4876, 1K-4884 and 1K-4896. The determined cDNA sequences for these clones are provided in SEQ ID NOS: 77–92, respectively. Comparison of these sequences with those in the gene bank as described above, revealed no significant homologies to 1G-4741, 1G-4734, 1I-4807, 1J-4876 and 1K-4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1J-4876, 1K-4884 and 1K-4896, provided in SEQ ID NOS: 179–188 and 191–193, respectively, and to the determination of additional partial cDNA sequences for 1I-4810 and 1I-4811, provided in SEQ ID NOS: 189 and 190, respectively.

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1-4278, 1 D-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two novel clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Example 2

Determination of Tissue Specificity of Prostate Tumor Polypeptides

Using gene specific primers, mRNA expression levels for the representative prostate tumor polypeptides F1-16, H1-1, J1-17, L1-12, F1-12 and N1-1862 were examined in a variety of normal and tumor tissues using RT-PCR.

Briefly, total RNA was extracted from a variety of normal and tumor tissues using Trizol reagent as described above. First strand synthesis was carried out using 1–2 $\mu$g of total RNA with SuperScript II reverse transcriptase (BRL Life Technologies) at 42° C. for one hour. The cDNA was then amplified by PCR with gene-specific primers. To ensure the semi-quantitative nature of the RT-PCR, $\beta$-actin was used as an internal control for each of the tissues examined. First, serial dilutions of the first strand cDNAs were prepared and RT-PCR assays were performed using $\beta$-actin specific primers. A dilution was then chosen that enabled the linear range amplification of the $\beta$-actin template and which was sensitive enough to reflect the differences in the initial copy numbers. Using these conditions, the $\beta$-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 and L1-12 appear to be specifically over-expressed in prostate, with both genes being expressed at high levels in prostate tumor and normal prostate but at low to undetectable levels in all the other tissues examined. N1-1862 was found to be over-expressed in 60% of prostate tumors and detectable in normal colon and kidney. The RT-PCR results thus indicate that F1-16, H1-1, J1-17, N1-1862 and L1-12 are either prostate specific or are expressed at significantly elevated levels in prostate.

Further RT-PCR studies showed that F1-12 is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 is over-expressed in prostate tumors and normal prostate, while being undetectable in other normal tissues tested. J1-17 was detected in two prostate tumors and not in the other tissues tested. N1-1862 was found to be over-expressed in three prostate tumors and to be expressed in normal prostate, colon and kidney, but not in other tissues tested. F1-12 was found to be highly expressed in two prostate tumors and to be undetectable in all other tissues tested.

The micro-array technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 was found to be over-expressed in normal prostate and prostate tumor, with some expression being detected in normal skeletal muscle. Both J1-12 and F1-12 were found to be over-expressed in prostate tumor, with expression being lower or undetectable in all other tissues tested. N1-1862 was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Example 3

Isolation and Characterization of Prostate Tumor Polypeptides by PCR-Based Subtraction A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRI' *E. coli* (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79 and P84. The determined cDNA sequences for these clones are provided in SEQ ID NO:41–45, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. An additional clone, referred to as P703, was found to have five splice variants. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The determined cDNA sequence for an extended spliced form of P703 is provided in SEQ ID NO: 225. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCR as described above. Expression was examined in one sample of each tissue type unless otherwise indicated.

P9 was found to be highly expressed in normal prostate and prostate tumor compared to all normal tissues tested except for normal colon which showed comparable expression. P20 was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies resulted in the isolation of twelve additional clones, hereinafter referred to as 10-d8, 10-h10, 11-c8, 7-g6, 8-b5, 8-b6, 8-d4, 8-d9, 8-g3, 8-h11, 9-f12 and 9-f3. The determined DNA sequences for 10-d8, 10-h10, 11-c8, 8-d4, 8-d9, 8-h11, 9-f12 and 9-f3 are provided in SEQ ID NO: 207, 208, 209, 216, 217, 220, 221 and 222, respectively. The determined forward and reverse DNA sequences for 7-g6, 8-b5, 8-b6 and 8-g3 are provided in SEQ ID NO: 210 and 211; 212 and 213; 214 and 215; and 218 and 219, respectively. Comparison of these sequences with those in the gene bank revealed no significant homologies to the sequence of 9-f3. The clones 10-d8, 11-c8 and 8-h11 were found to show some homology to previously isolated ESTs, while 10-h10, 8-b5, 8-b6, 8-d4, 8-d9, 8-g3 and 9-f12 were found to show some homology to previously identified genes. Further characterization of 7-G6 and 8-G3 showed identity to the known genes PAP and PSA, respectively.

mRNA expression levels for these clones were determined using the micro-array technology described above. The clones 7-G6, 8-G3, 8-B5, 8-B6, 8-D4, 8-D9, 9-F3, 9-F12, 9-H3, 10-A2, 10-A4, 11-C9 and 11-F2 were found to be over-expressed in prostate tumor and normal prostate, with expression in other tissues tested being low or undetectable. Increased expression of 8-F11 was seen in prostate tumor and normal prostate, bladder, skeletal muscle and colon. Increased expression of 10-H10 was seen in prostate tumor and normal prostate, bladder, lung, colon, brain and large intestine. Increased expression of 9-B1 was seen in prostate tumor, breast tumor, and normal prostate, salivary gland, large intestine and skin, with increased expression of 11-C8 being seen in prostate tumor, and normal prostate and large intestine.

An additional cDNA fragment derived from the PCR-based normal prostate subtraction, described above, was found to be prostate specific by both micro-array technology and RF-PCR. The determined cDNA sequence of this clone (referred to as 9-A11) is provided in SEQ ID NO: 226. Comparison of this sequence with those in the public databases revealed 99% identity to the known gene HOXB13.

Further studies led to the isolation of the clones 8-C6 and 8-H7. The determined cDNA sequences for these clones are provided in SEQ ID NO: 227 and 228, respectively. These sequences were found to show some homology to previously isolated ESTs.

Example 4

Synthesis of Polypeptides

Polypeptides may be synthesized on a Perkin Elmer/Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase FIPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 5

Further Isolation and Characterization of Prostate Tumor Polypeptides by PCR-Based Subtraction A cDNA library generated from prostate primary tumor mRNA as described above was subtracted with cDNA from normal prostate. The subtraction was performed using a PCR-based protocol (Clontech), which was modified to generate larger fragments. Within this protocol, tester and driver double stranded cDNA were separately digested with five restriction enzymes that recognize six-nucleotide restriction sites (MluI, MscI, PvuII, SalI and StuI). This digestion resulted in an average cDNA size of 600 bp, rather than the average size of 300 bp that results from digestion with RsaI according to the Clontech protocol. This modification did not affect the subtraction efficiency. Two tester populations were then created with different adapters, and the driver library remained without adapters.

The tester and driver libraries were then hybridized using excess driver cDNA. In the first hybridization step, driver was separately hybridized with each of the two tester cDNA populations. This resulted in populations of (a) unhybridized tester cNAs, (b) tester cDNAs hybridized to other tester cDNAs, (c) tester cDNAs hybridized to driver cDNAs and (d) unhybridized driver cDNAs. The two separate hybridization reactions were then combined, and rehybridized in the presence of additional denatured driver cDNA. Following this second hybridization. in addition to populations (a) through (d), a fifth population (e) was generated in which tester cDNA with one adapter hybridized to tester cDNA with the second adapter. Accordingly, the second hybridization step resulted in enrichment of differentially expressed sequences which could be used as templates for PCR amplification with adaptor-specific primers.

The ends were then filled in, and PCR amplification was performed using adaptor-specific primers. Only population (e), which contained tester cDNA that did not hybridize to driver cDNA, was amplified exponentially. A second PCR amplification step was then performed, to reduce background and further enrich differentially expressed sequences.

This PCR-based subtraction technique normalizes differentially expressed cDNAs so that rare transcripts that are overexpressed in prostate tumor tissue may be recoverable. Such transcripts would be difficult to recover by traditional subtraction methods.

In addition to genes known to be overexpressed in prostate tumor, seventy-seven novel clones were identified. Sequences of these partial cDNAs are provided in SEQ ID NOs:229 to 305. Most of these clones had no significant homology to database sequences. Exceptions were JPTPN23 (SEQ ID NO:231; similarity to pig valosin-containing protein), JPTPN30 (SEQ ID NO:234; similarity to rat mRNA for proteasome subunit), JPTPN45 (SEQ ID NO:243; similarity to rat norvegicus cytosolic NADP-dependent isocitrate dehydrogenase), JPTPN46 (SEQ ID NO:244; similarity to human subclone H8 4 d4 DNA sequence), JP1D6 (SEQ ID NO:265; similarity to G. gallus dynein light chain-A), JP8D6 (SEQ ID NO:288); similarity to human BAC clone RG016J04), JP8F5 (SEQ ID NO:289; similarity to human subclone H8 3 b5 DNA sequence) and JP8E9 (SEQ ID NO:299; similarity to human Alu sequence).

The novel clones identified were:

| | |
|---|---|
| JPTPN13 | SEQ ID NO:229 |
| JPTPN14 | SEQ ID NO:230 |
| JPTPN23 | SEQ ID NO:231 |
| JPTPN24 | SEQ ID NO:232 |
| JPTPN25 | SEQ ID NO:233 |
| JPTPN30 | SEQ ID NO:234 |
| JPTPN34 | SEQ ID NO:235 |
| JPTPN35 | SEQ ID NO:236 |
| JPTPN36 | SEQ ID NO:237 |
| JPTPN38 | SEQ ID NO:238 |
| JPTPN39 | SEQ ID NO:239 |
| JPTPN40 | SEQ ID NO:240 |
| JPTPN41 | SEQ ID NO:241 |
| JPTPN42 | SEQ ID NO:242 |
| JPTPN45 | SEQ ID NO:243 |
| JPTPN46 | SEQ ID NO:244 |
| JPTPN51 | SEQ ID NO:245 |
| JPTPN56 | SEQ ID NO:246 |
| JPTPN64 | SEQ ID NO:247 |
| JPTPN65 | SEQ ID NO:248 |
| JPTPN67 | SEQ ID NO:249 |
| JPTPN76 | SEQ ID NO:250 |
| JPTPN84 | SEQ ID NO:251 |
| JPTPN85 | SEQ ID NO:252 |
| JPTPN86 | SEQ ID NO:253 |
| JPTPN87 | SEQ ID NO:254 |
| JPTPN88 | SEQ ID NO:255 |
| JP1F1 | SEQ ID NO:256 |
| JP1F2 | SEQ ID NO:257 |
| JP1C2 | SEQ ID NO:258 |
| JP1B1 | SEQ ID NO:259 |
| JP1B2 | SEQ ID NO:260 |
| JP1D3 | SEQ ID NO:261 |
| JP1A4 | SEQ ID NO:262 |
| JP1F5 | SEQ ID NO:263 |
| JP1E6 | SEQ ID NO:264 |
| JP1D6 | SEQ ID NO:265 |
| JP1B5 | SEQ ID NO:266 |
| JP1A6 | SEQ ID NO:267 |
| JP1E8 | SEQ ID NO:268 |
| JP1D7 | SEQ ID NO:269 |
| JP1D9 | SEQ ID NO:270 |
| JP1C10 | SEQ ID NO:271 |
| JP1A9 | SEQ ID NO:272 |
| JP1F12 | SEQ ID NO:273 |
| JP1E12 | SEQ ID NO:274 |
| JP1D11 | SEQ ID NO:275 |
| JP1C11 | SEQ ID NO:276 |
| JP1C12 | SEQ ID NO:277 |
| JP1B12 | SEQ ID NO:278 |
| JP1A12 | SEQ ID NO:279 |
| JP8G2 | SEQ ID NO:280 |
| JP8H1 | SEQ ID NO:281 |
| JP8H2 | SEQ ID NO:282 |
| JP8A3 | SEQ ID NO:283 |
| JP8A4 | SEQ ID NO:284 |
| JP8C3 | SEQ ID NO:285 |
| JP8G4 | SEQ ID NO:286 |
| JP8B6 | SEQ ID NO:287 |
| JP8D6 | SEQ ID NO:288 |
| JP8F5 | SEQ ID NO:289 |
| JP8A8 | SEQ ID NO:290 |
| JP8C7 | SEQ ID NO:291 |
| JP8D7 | SEQ ID NO:292 |

-continued

| | |
|---|---|
| JP8D8 | SEQ ID NO:293 |
| JP8E7 | SEQ ID NO:294 |
| JP8F8 | SEQ ID NO:295 |
| JP8G8 | SEQ ID NO:296 |
| JP8B10 | SEQ ID NO:297 |
| JP8C10 | SEQ ID NO:298 |
| JP8E9 | SEQ ID NO:299 |
| JP8E10 | SEQ ID NO:300 |
| JP8F9 | SEQ ID NO:301 |
| JP8H9 | SEQ ID NO:302 |
| JP8C12 | SEQ ID NO:303 |
| JP8E11 | SEQ ID NO:304 |
| JP8E12 | SEQ ID NO:305 |

Example 6

Peptide Priming of Mice and Propagation of CTL Lines

This Example illustrates the preparation of a CTL cell line specific for cells expressing the P502S gene.

Mice expressing the transgene for human HLA A2.1 (provided by Dr L. Sherman, The Scripps Research Institute, La Jolla, Calif.) were immunized with P2S #12 peptide (VLGWVAEL; SEQ ID NO:306), which is derived from the P502S gene (also referred to herein as J1-17, SEQ ID NO:8), as described by Theobald et al., *Proc. Natl. Acad. Sci. USA* 92:11993–11997, 1995 with the following modifications. Mice were immunized with 100 μg of P2S #12 and 120 μg of an I-A$^b$ binding peptide derived from hepatitis B Virus protein emulsified in incomplete Freund's adjuvant. Three weeks later these mice were sacrificed and using a nylon mesh single cell suspensions prepared. Cells were then resuspended at 6×10$^6$ cells/ml in complete media (RPMI-1640 (Gibco BRL, Gaithersburg, Md.) containing 10% FCS, 2 mM Glutamine (Gibco BRL), sodium pyruvate (Gibco BRL), non-essential amino acids (Gibco BRL, 2×10$^{-5}$ M 2-mercaptoethanol, 50 U/ml penicillin and streptomycin) and cultured in the presence of irradiated (3000 rads) P2S#12 pulsed (5 mg/ml P2S #12 and 10 mg/ml β2-microglobulin) LPS blasts (A2 transgenic spleens cells cultured in the presence of 7 μg/ml dextran sulfate and 25 μg/ml LPS for 3 days). Six days later cells (5×10$^5$/ml) were restimulated with 2.5×10$^6$/ml peptide pulsed irradiated (20, 000 rads) EL4A2Kb cells (Sherman et al, *Science* 258:815–818, 1992) and 3×10$^6$/ml A2 transgenic spleen feeder cells. Cells were cultured in the presence of 20 U/ml IL-2. Cells were continued to be restimulated on a weekly basis as mentioned, in preparation for cloning the line.

P2S#12 line was cloned by limiting dilution analysis with peptide pulsed EL4 A2Kb tumor cells (1×10$^4$ cells/well) as stimulators and A2 transgenic spleen cells as feeders (5×10$^5$ cells/well) grown in the presence of 30 U/ml IL-2. On day 14, cells were restimulated as before. On day 21, clones that were growing were isolated and maintained in culture. Several of these clones demonstrated reactivity (lysis) against human fibroblasts (HLA A2.1 expressing) transduced with P502S gene significantly higher than control fibroblasts. An example is presented in FIG. 1.

This data indicates that P2S #12 represents a naturally processed epitope of the P502S protein that is expressed in the context of the human HLA A2.1 molecule.

Example 7

Ability of T Cells to Recognize Prostate Tumor Polypeptides

This Example illustrates the ability of T cells specific for a prostate tumor polypeptide to recognize human tumor.

Figure 2A:
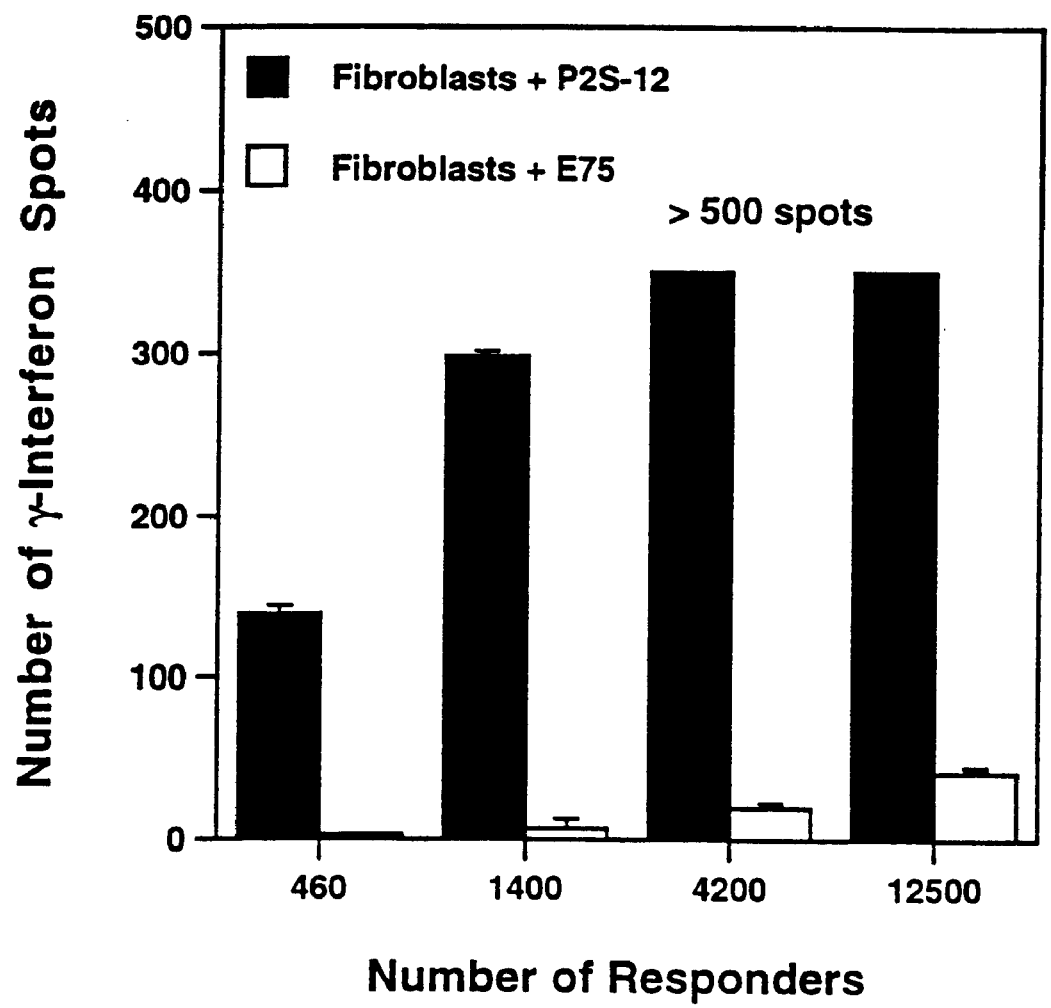
FIGS. 2A and 2B are graphs illustrating the ability of T cells to recognize cells expressing the representative prostate tumor polypeptide P502S. In each case, the number of γ-interferon spots is shown for different numbers of responders.
Figure 2B:
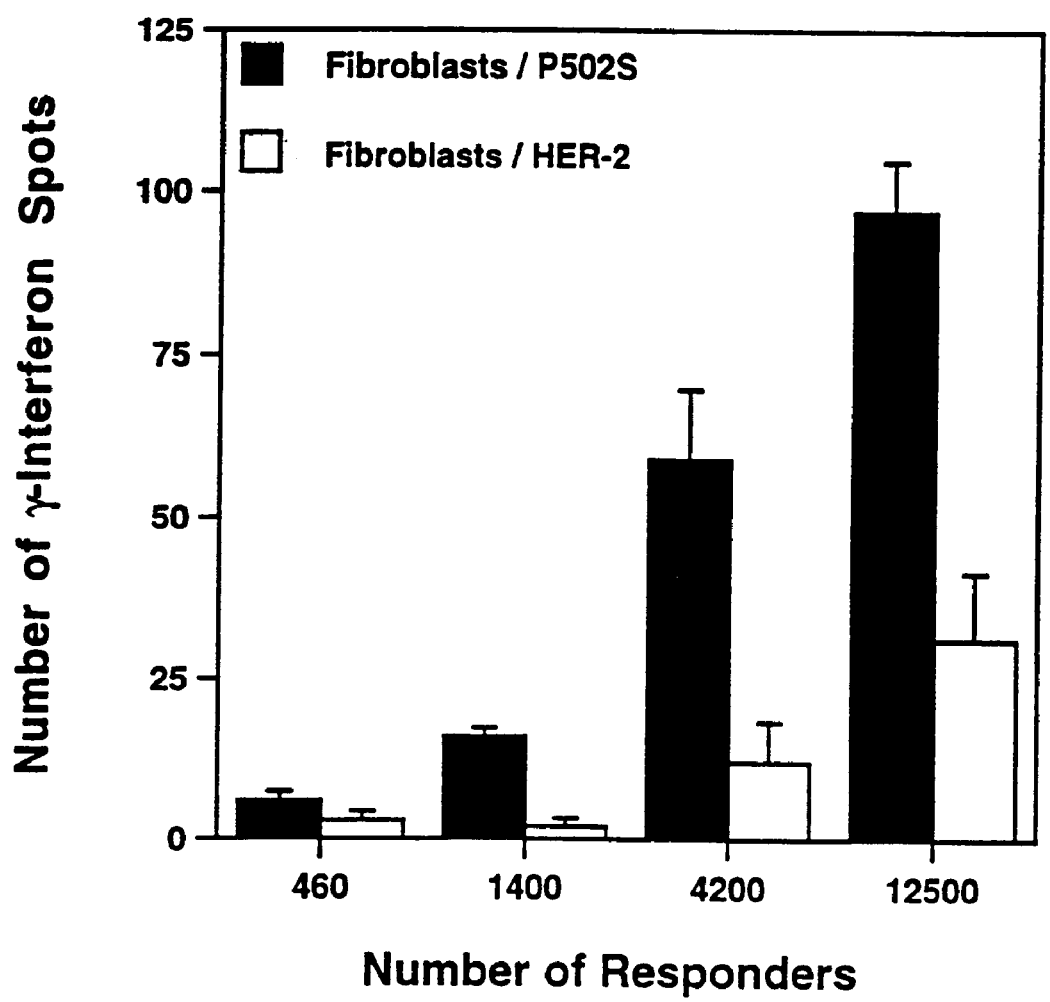

Human $CD8^{30}$ T cells were primed in vitro to the P2S-12 peptide (VLGWVAEL; SEQ ID NO:306) derived from the P502S (J1-17) gene using dendritic cells according to protocol set forth by Van Tsai et al., *Critical Reviews in Immunology* 18:65–75, 1998. The resulting $CD8^+$ T cell microcultures were tested for their ability to recognize the P2S-12 peptide presented by autologous fibroblasts or fibroblasts which were transduced to express the P502S gene in a γ-interferon ELISPOT assay (see Lalvani et al., *J. Experimental Medicine* 186:859–865, 1997). Briefly, titrating numbers of T cells were assayed in duplicate on $10^4$ fibroblasts in the presence of 3 μg/ml human $β_2$-microglobulin and 1 μg/ml P2S-12 peptide or control E75 peptide. In addition, T cells were simultaneously assayed on autologous fibroblasts transduced with the P502S gene or as a control, fibroblasts transduced with HER-2/neu. Prior to the assay, the fibroblasts were treated with 10 ng/ml γ-interferon for 48 hours to upregulate class I MHC expression. One of the microcultures (#5) demonstrated strong recognition of both peptide pulsed fibroblasts as well as transduced fibroblasts in a γ-interferon ELISPOT assay. FIG. 2A demonstrates that there was a strong increase in the number of γ-interferon spots with increasing numbers of T cells on fibroblasts pulsed with the P2S-12 peptide (solid bars) but not with the control E75 peptide (open bars). This shows the ability of these T cells to specifically recognize the P2S-12 peptide. In FIG. 2B, this microculture also demonstrated an increase in the number of γ-interferon spots with increasing numbers of T cells on fibroblasts transduced to express the P502S gene but not the HER-2/neu gene. These results provide additional confirmatory evidence that the P2S-12 peptide is a naturally processed epitope of the P502S protein. Furthermore, this also demonstrates that there exists in the human T cell repertoire, high affinity T cells which are capable of recognizing this epitope. These T cells should also be capable of recognizing human tumors which express the P502S gene.

From the foregoing, it will be appreciated that, although specific embodiments of the invention have been described herein for the purposes of illustration, various modifications may be made without deviating from the spirit and scope of the invention. Accordingly, the present invention is not limited except as by the appended claims.

What is claimed is:

1. An isolated polypeptide comprising SEQ ID NO:172.
2. An isolated polypeptide encoded by SEQ ID NO: 171.
3. A composition comprising a polypeptide according to any one of claims 1 and 2 and a physiologically acceptable carrier.
4. A method for stimulating an immune response in a patient, comprising administering a composition according to claim 3.
5. A composition comprising a polypeptide according to any one of claims 1 and 2 and a non-specific immune response enhancer.
6. A composition according to claim 5, wherein the non-specific immune response enhancer is an adjuvant.
7. A method for stimulating an immune response in a patient, comprising administering a composition according to claim 5.

* * * * *